(12) United States Patent
Forsell

(10) Patent No.: US 11,484,717 B2
(45) Date of Patent: Nov. 1, 2022

(54) METHOD FOR THE TREATMENT OF GALLSTONES

(71) Applicant: Peter Forsell, Bouveret (CH)

(72) Inventor: Peter Forsell, Bouveret (CH)

( * ) Notice: Subject to any disclaimer, the term of this patent is extended or adjusted under 35 U.S.C. 154(b) by 374 days.

(21) Appl. No.: 16/564,065

(22) Filed: Sep. 9, 2019

(65) Prior Publication Data

US 2020/0101296 A1 Apr. 2, 2020

Related U.S. Application Data

(63) Continuation of application No. 13/367,002, filed on Feb. 6, 2012, now Pat. No. 10,406,371, which is a continuation of application No. 12/285,810, filed on Oct. 14, 2008, now abandoned.

(60) Provisional application No. 60/960,716, filed on Oct. 11, 2007.

(51) Int. Cl.
| | |
|---|---|
| *A61N 1/365* | (2006.01) |
| *A61N 1/36* | (2006.01) |
| *A61F 7/12* | (2006.01) |
| *A61B 17/22* | (2006.01) |
| *A61B 17/12* | (2006.01) |
| *A61B 17/135* | (2006.01) |
| *A61M 60/148* | (2021.01) |
| *A61M 60/268* | (2021.01) |
| *A61N 1/40* | (2006.01) |
| *A61B 17/00* | (2006.01) |
| *A61M 60/40* | (2021.01) |
| *A61M 60/50* | (2021.01) |

(Continued)

(52) U.S. Cl.
CPC .... *A61N 1/36514* (2013.01); *A61B 17/12009* (2013.01); *A61B 17/1355* (2013.01); *A61B 17/22* (2013.01); *A61F 7/12* (2013.01); *A61M 60/148* (2021.01); *A61M 60/268* (2021.01); *A61N 1/3605* (2013.01); *A61B 2017/00163* (2013.01); *A61B 2017/00212* (2013.01); *A61B 2017/00221* (2013.01); *A61B 2017/00411* (2013.01); *A61B 2017/00982* (2013.01); *A61B 2017/00991* (2013.01); *A61F 2007/126* (2013.01); *A61M 60/122* (2021.01); *A61M 60/40* (2021.01); *A61M 60/50* (2021.01); *A61M 60/871* (2021.01); *A61M 2205/3334* (2013.01); *A61M 2205/8243* (2013.01); *A61N 1/36564* (2013.01); *A61N 1/36578* (2013.01); *A61N 1/403* (2013.01)

(58) Field of Classification Search
CPC .... A61N 1/36007; A61N 1/3606; A61N 1/00; A61N 1/02; A61N 1/36; A61N 1/05
See application file for complete search history.

(56) References Cited

U.S. PATENT DOCUMENTS 6,571,127 B1 * 5/2003 Ben-Haim ......... A61N 1/36007
607/40

* cited by examiner

*Primary Examiner* — Deborah L Malamud

(57) ABSTRACT

There is provided a method for controlling the movement of bile and/or gall stones in the biliary duct. The method comprises gently constricting (i.e., without substantially hampering the blood circulation in the tissue wall) at least one portion of the tissue wall to influence the movement of bile and/or gallstones in the biliary duct, and stimulating the constricted wall portion to cause contraction of the wall portion to further influence the movement of bile and/or gallstones in the biliary duct. The method can be used for restricting or stopping the movement of bile and/or gallstones in the biliary duct, or for actively moving the fluid in the biliary duct, with a low risk of injuring the biliary duct.

20 Claims, 36 Drawing Sheets

(51) Int. Cl.
*A61M 60/122* (2021.01)
*A61M 60/871* (2021.01)

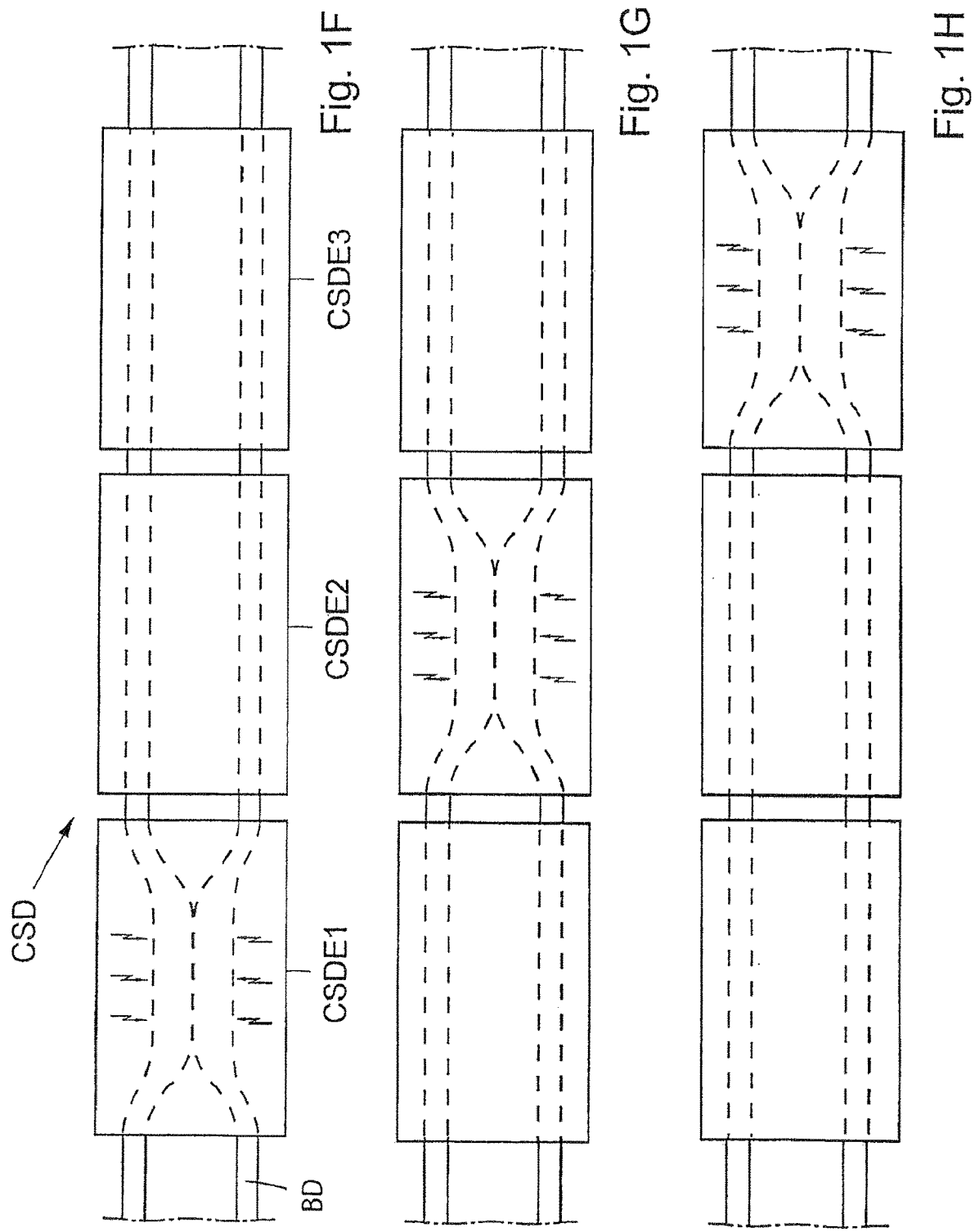

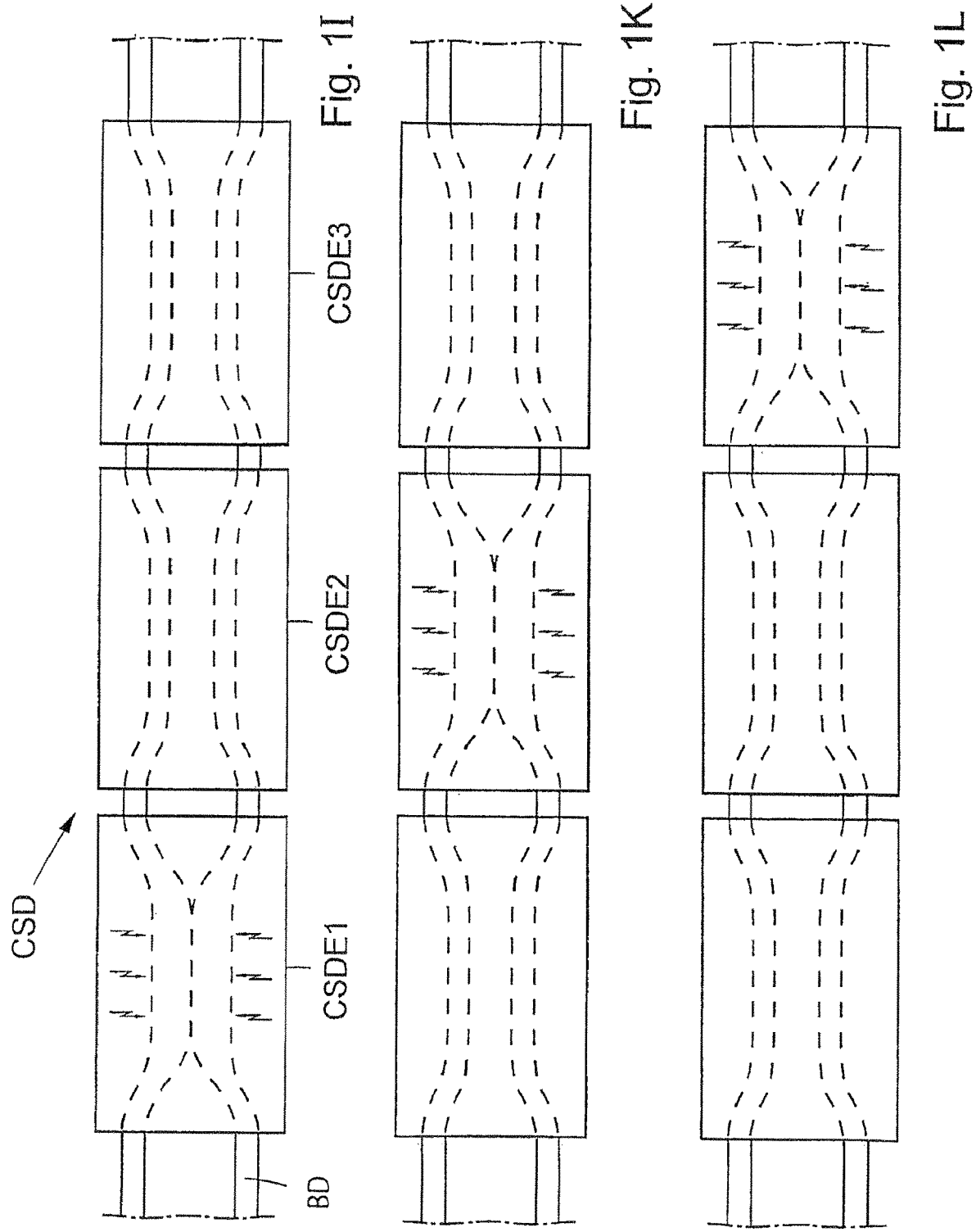

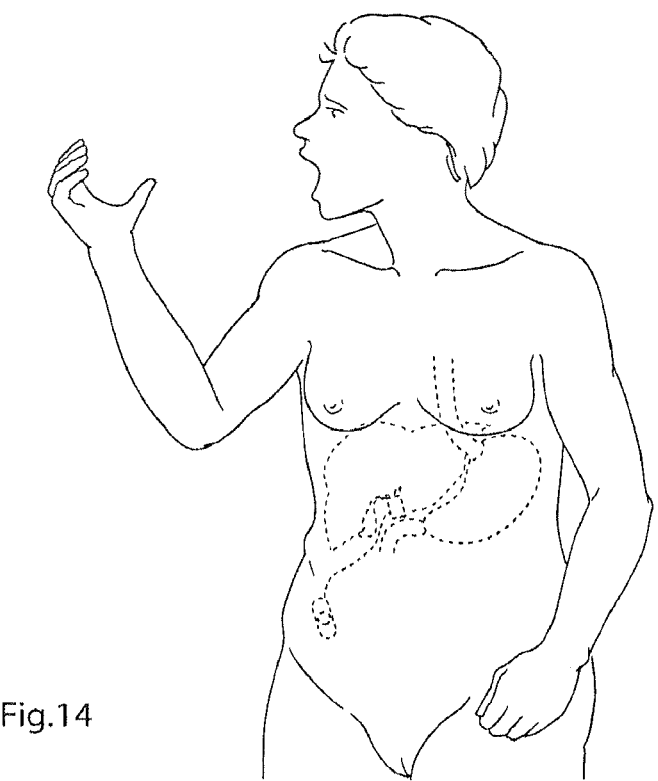
Fig.14
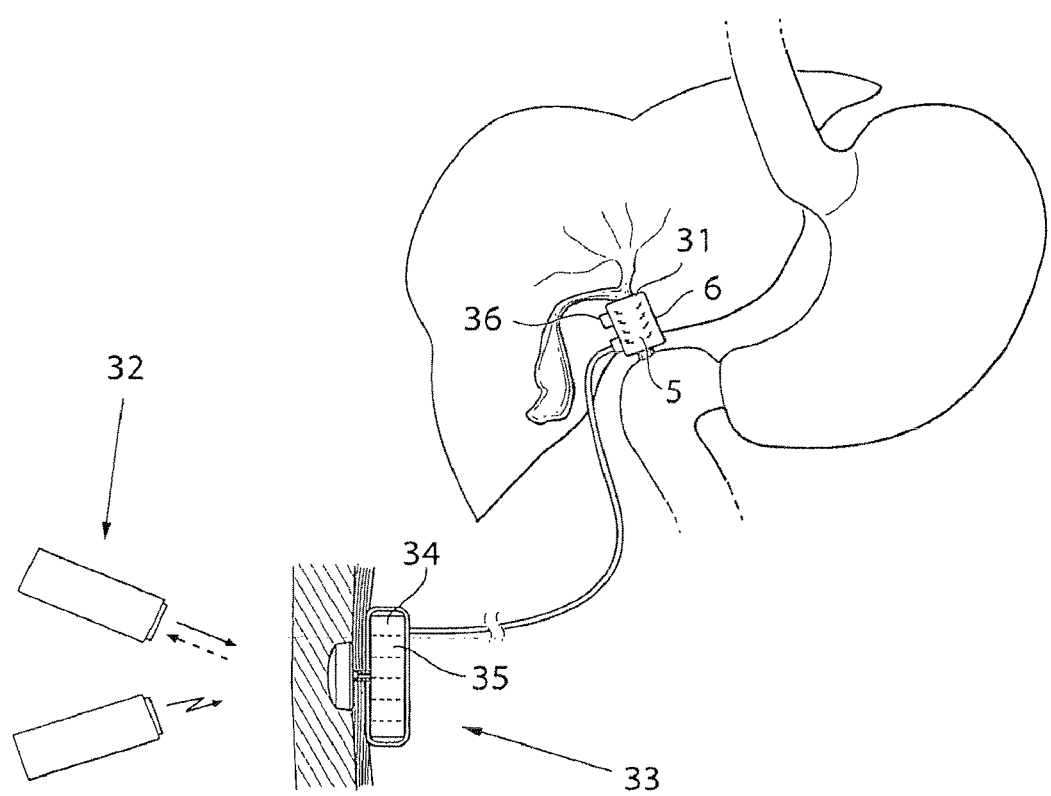

METHOD FOR THE TREATMENT OF GALLSTONES

CROSS-REFERENCE TO RELATED APPLICATION

This application is a continuation of U.S. application Ser. No. 13/367,002, filed 6 Feb. 2012, which is a continuation application of U.S. application Ser. No. 12/285,810, filed 14 Oct. 2008, which claims the benefit of provisional Application No. 60/960,716, filed 11 Oct. 2007, the entire contents of each of which are hereby incorporated by reference.

FIELD OF THE INVENTION

The present invention relates to the treatment of gallstones.

BACKGROUND OF THE INVENTION

Cholelithiasis (gallstones) is the presence or formation of gallstones in the biliary tract can cause intense pain and is potentially dangerous. It is a common medical problem, affecting 10 to 15 percent of the population. Bile is formed in the gallbladder and consists of water, cholesterol, fats, bile salts, proteins, and bilirubin. The main function is to secrete bile salts that emulsify dietary fats and to secrete bilirubin, which is a waste product. Bile is produced by hepatocytes of the liver and transported to the gall bladder were it is stored for release into the duodenum and is transported through a system of ducts. The ducts include the hepatic ducts, which carry bile out of the liver, the cystic duct, which takes bile to and from the gallbladder, and the common bile duct, which takes bile from the cystic and hepatic ducts to the small intestine. These three ducts together with the sphincters that control them, are referred to herein as the "biliary duct" or the "biliary ducts". Biliary ducts has smooth muscle tissue, that enables the ducts to contract.

Gallstones may form when cholesterol or bilirubin precipitates into hard aggregates. Gallstones can block the normal flow of bile if they move from the gallbladder and lodge in any of the ducts that carry bile from the liver to the small intestine. Symptoms of blocked bile ducts include intense pain and are often referred to as a gallbladder "attack" because they occur suddenly. If any of the biliary ducts remain blocked by gallstones for a significant period of time, severe damage or infection can occur in the gallbladder, liver, or pancreas. Left untreated, the condition can be fatal.

The most common treatment for gallstones is the complete removal of the gallbladder (cholecystectomy). Present data suggest that the gallbladder is a nonessential organ and that patient can live a normal life without the gallbladder, as bile can instead reach the intestines via direct flow from the liver through the hepatic ducts into the common bile duct and into the small intestine, instead of being stored in the gallbladder.

Removal of the call bladder is usually performed using laparascopical procedures. However, open surgery is necessary in about 5 percent of gallbladder operations. Recovery from open surgery usually requires 3 to 5 days in the hospital and several weeks at home.

A serious disadvantage with the current treatment is the risk for serious damage to the bile duct during surgery. This is a serious problem and requires additional surgery.

Another disadvantage is that a high percentage of patients suffer from diarrhea permanently or for a long time after removal of the gall bladder.

Another more serious disadvantage is that the element that constricts, clamps or restricts a bodily organ may injure the tissue wall of the organ. Thus, a consequence of the constricting action of the element on the organ is that the element might erode into the organ over time, and in a worst case, penetrate the constricted wall portion of the organ. In addition, blood circulation in the constricted tissue wall portion of the organ is eventually hampered by the pressure exerted by the element, so that poor blood circulation, or worse, no blood circulation results in deterioration of the constricted tissue.

One solution to prevent tissue deterioration due to poor blood circulation could be to apply two or more separately operating constricting elements along respective tissue wall portions of the organ and operate the elements sequentially, whereby each tissue wall portion would have time to recover, i.e., restore normal blood circulation while one of the other tissue wall portions is constricted. However, an apparatus devised in accordance with this solution would have several disadvantages. First, the apparatus would require a large amount of space, making it impractical to implant. Second, the operation of the apparatus in moving the constricting elements between constricting and non-constricting positions day and night would require a large power supply. Such a large power supply would necessitate the implantation of a very large, high capacity battery and/or a sophisticated system for continuous wireless transmission of energy from outside the patient's body for frequent charging of an implanted rechargeable battery. Thus, because of its large size and high power consumption, the apparatus would be impractical or even unrealistic. Third, a sophisticated control system would be necessary to control the moving elements. Finally, such a complicated apparatus of the type described above would significantly add to the costs of treating a malfunctioning sphincter. However, such embodiments may be of value in some combinations with the present invention.

Another solution to the problem of malfunctioning sphincters that has been previously used has been the electric stimulation of the sphincter, to restore its normal function, i.e., the contraction and closing of its associated lumen. This solution would work where the normal sphincteric function is somewhat reduced and has not completely ceased. European patent application 1004330 A1 discloses an example of such a solution, in which electric pulses are delivered to the lower esophageal sphincter of a patient suffering from reflux disease to minimize reflux. However, the esophageal sphincter has to be continuously stimulated with electric pulses to keep it closed, except when the patient eats, which may result in a decreased stimulation effect over time. An even more serious drawback to this solution is that the continuous stimulation over time might cause tissue deterioration due to poor blood circulation.

The use of electric stimula to restore the function of a malfunctioning sphincter is only possible if the sphincter responds sufficiently to the stimula, i.e., closes the lumen in question. In cases where the function of a sphincter has completely ceased, or the sphincter has been removed from the patient's body, electric stimulation cannot be employed.

BRIEF SUMMARY OF THE INVENTION

The object of the present invention is to provide a method for enhancing the movement of gallstones from the bile ducts to the duodenum, so as to at least substantially or even completely eliminate the blockage and pain associated with gallstones. One major purpose of the invention is to enable the transport of gallstones to the duodenum as this relieves the symptoms. Gallstones that reach the duodenum are secreted together with fasces.

In accordance with this object of the present invention, there is provided a method for enhancing the movement of gallstones in a patient suffering from gallstone trouble, the method comprising stimulating the constricted wall portion to cause contraction of the wall portion to influence the movement in the biliary duct.

Herein is also disclosed how flow in the biliary duct can be restricted by simultaneously using a restriction device and stimulation of the tissue of the wall of the biliary duct. It may be of great importance to be able to completely close the biliary duct. One such occasion is when surgery on the biliary duct is to be performed.

Furthermore, the restriction device will be of use when a gallstone is lodged and cannot move downstream. It is then possible.

to use the described restriction device in order to release the lodged gallstone.

In accordance with this object of the present invention, there is also provided a method for enhancing the movement of gallstones in a patient suffering from gallstone trouble, the method comprising:
a) gently constricting a portion of the wall to influence the movement in the biliary duct, and
b) stimulating the constricted wall portion to cause contraction of the wall portion to further influence the movement in the biliary duct.

The present invention provides an advantageous combination of the method steps (a) and (b), which results in a two-stage influence on the movement of bile and/or gallstones in the lumen of a biliary duct. Thus, applying a relatively weak force against the wall portion gently constricts the tissue wall and the constricted wall portion is stimulated to achieve the desired final influence on the movement of bile and/or gallstones in the biliary duct. The phrase "gently constricts a portion of the tissue wall" is to be understood as constricting the wall portion without substantially hampering the blood circulation in the tissue wall.

Preferably, step (b) is performed by intermittently and individually stimulating different areas of the wall portion. Such an intermittent and individual stimulation of different areas of the wall portion of the biliary duct allows tissue of the wall portion to maintain over time substantially normal blood circulation.

Alternatively the method comprising:
a) gently constricting at least one portion of the tissue wall to influence the flow in the lumen, or
b) stimulating at least one portion of the tissue wall to cause contraction of the wall portion to further influence the flow in the lumen.

It should be understood that any embodiment or part of embodiment disclosed below in this application for the constriction and stimulation devices combined in the constriction/stimulation unit could be used for the separate constriction device and separate stimulation device, where applicable.

The method of the present invention can be practiced anywhere along the biliary ducts, for example on the hepatic ducts, the common bile duct or the cystic ducts or any of the sphincters associated with these ducts. Preferably, the constriction step (a) and stimulation step (b) are performed independently of each other. Steps (a) and (b) may be performed simultaneously. Optionally, step (b) may or may not be performed while step (a) is performed.

Initially, the constriction of the wall portion can be calibrated by stimulating the wall portion while adjusting the constriction of the wall portion until the desired restriction of the movement of bile and/or gallstones in the biliary duct is obtained.

Flow Restriction

The method of the present invention is well suited for restricting the movement of bile and/or gallstones in the lumen of a biliary duct. Thus, in a principal embodiment of the invention, the wall portion is constricted, so that the movement of bile and/or gallstones in the biliary duct at least is restricted and the constricted wall portion is stimulated to at least further restrict the movement of bile and/or gallstones. Specifically, the wall portion is constricted to a constricted state, in which the blood circulation in the constricted wall portion is substantially unrestricted and the movement of bile and/or gallstones in the biliary duct is at least restricted, and the constricted wall portion is stimulated when it is in the constricted state to at least further restrict the movement of bile and/or gallstones in the biliary duct.

The constriction step (a) and stimulation step (b) are suitably performed to constrict and stimulate the wall portion to an extent that depends on the flow restriction that is desired to be achieved in a specific application of the method of the invention. Thus, in accordance with a first flow restriction option, step (a) is performed by constricting the wall portion, so that the movement of bile and/or gallstones in the biliary duct is restricted but not stopped, and step (b) is performed by stimulating the constricted wall portion to cause contraction thereof, so that the movement of bile and/or gallstones in the biliary duct is further restricted but not stopped. The method may further comprise sensing a physical parameter of the patient and adjusting the intensity of the stimulation of the wall portion in response to the sensed parameter.

In accordance with a second flow restriction option, step (a) is performed by constricting the wall portion, so that the movement of bile and/or gallstones in the biliary duct is restricted but not stopped, and step (b) is performed by stimulating the constricted wall portion to cause contraction thereof, so that the movement of bile and/or gallstones in the biliary duct is stopped.

When using the method of the invention in accordance with the first or second options, the method may further comprise (c) ceasing stimulating the wall portion to increase or allow the movement of bile and/or gallstones in the biliary duct and (d) releasing the wall portion to restore the movement of bile and/or gallstones in the biliary duct.

In accordance with a third flow restriction option, step (a) is performed by constricting the wall portion, so that the movement of bile and/or gallstones in the biliary duct is substantially stopped, and step (b) is performed by stimulating the constricted wall portion to cause contraction thereof, so that the movement of bile and/or gallstones in the biliary duct is completely stopped. The method may further comprise (c) ceasing stimulating the wall portion to allow the movement of bile and/or gallstones in the biliary duct and (d) releasing the wall portion to restore the movement of bile and/or gallstones in the biliary duct.

Where the constricted wall portion is stimulated to contract, so that the movement of bile and/or gallstones in the biliary duct is stopped, a first length of the constricted wall portion and a second length of the constricted wall portion, which is located downstream of the first length, are suitably simultaneously and cyclically stimulated, wherein the first length is progressively stimulated in the upstream direction of the lumen and the second length is progressively stimulated in the downstream direction of the lumen.

Furthermore, when using the method of the invention in accordance with the second and third options, the method may further comprise sensing a physical parameter of the patient or functional parameter of implanted components and adjusting the stimulation of the wall portion in response to the sensed parameter. For example, the intensity of the stimulation of the wall portion may be increased in response to a sensed pressure increase in the lumen, so that the movement of bile and/or gallstones in the biliary duct remains stopped when a pressure increase occurs in the lumen. In particular, the method may comprise sensing a physical parameter of the patient's that relates to the pressure in the lumen, and controlling the stimulation of the wall portion in response to the sensed parameter. Any sensor for sensing a physical parameter of the patient, such as a pressure in the patient's body that relates to the pressure in the lumen may be provided, wherein the stimulation is controlled in response to signals from the sensor. Such a sensor may for example sense the pressure in the patient's abdomen, the pressure against the implanted constriction device or the pressure on the tissue wall of the biliary duct.

In accordance with a fourth restriction option, step (a) is performed by constricting the wall portion, so that the movement of bile and/or gallstones in the biliary duct is stopped. When needed, the wall portion is released to restore the movement of bile and/or gallstones in the biliary duct. Step (b) is only performed by stimulating the constricted wall portion to cause contraction thereof, so that the movement of bile and/or gallstones in the biliary duct remains stopped when a pressure increase occurs in the lumen. The method may further comprise sensing a physical parameter of the patient's body, such as a pressure in the patient's body that relates to the pressure in the lumen, and controlling the stimulation of the wall portion in response to the sensed parameter. Such a physical parameter may be a pressure in the patient's abdomen and the sensor may be a pressure sensor.

In some applications of the method of the invention, continuous stimulation may over time change the physical properties of the tissue so that the tissue might be injured. Also, the effect of a continuous stimulation of the tissue wall may decrease over time. Therefore, step (b) is preferably performed by intermittently and individually stimulating different areas of the wall portion so that the movement of bile and/or gallstones in the biliary duct continues to be restricted as desired and each area of the wall portion essentially maintains its natural physical properties over time to prevent the area from being injured. Advantageously, each area of the wall portion is stimulated during successive time periods, each time period being short enough to maintain over time satisfactory blood circulation in the area. Thus, the areas are stimulated so that an area that currently is not stimulated will have time to restore substantially normal blood circulation before it is stimulated again.

To maintain satisfactory blood circulation in the tissue wall of the patient's biliary duct stimulation step (b) is suitably performed by stimulating one or more of different areas of the wall portion at a time, preferably by sequentially stimulating the different areas of the wall portion or by shifting the stimulation from one area to another over time. Preferably, stimulation step (b) is performed by cyclically propagating the stimulation of the areas along the wall portion, for example in accordance with a determined stimulation pattern.

The method of the invention may further comprise controlling, preferably by the patient, the constriction and/or stimulation of the wall portion from outside the patient's body.

Generally, the method of the invention comprises sensing a physical parameter of the patient and controlling, preferably automatically, the constriction and/or stimulation of the wall portion in response to the sensed parameter.

The constriction step (a) may be performed by constricting any wall portions of a series of wall portions of the tissue wall of the biliary duct, respectively, either in random or in accordance with a predetermined sequence. The stimulation step (b) may be performed by stimulating any of the constricted wall portions of the series of wall portions. Specifically, step (a) may be performed by constricting all of the wall portions of the series of wall portions, and step (b) may be performed by stimulating any constricted wall portions in random or in accordance with a predetermined sequence to close the biliary duct.

Moving Bile and/or Gall Stones in the Biliary Duct

Importantly, the method of the present invention can be practised for actively moving the bile and/or gall stones in lumen of a patient's biliary duct. Thus, in the embodiments of the invention listed below, steps (a) and (b) are co-operated to move the bile and/or gall stones in the lumen.

1) Step (a) is performed by constricting the wall portion to restrict the movement of bile and/or gallstones in the biliary duct, and step (b) is performed by stimulating the constricted wall portion to close the lumen either at an upstream end or a downstream end of the constricted wall portion. The method further comprises (c) increasing the constriction of the wall portion to move the bile and/or gall stones in the lumen.

2) Step (a) is performed by constricting the wall portion to restrict the movement of bile and/or gallstones in the biliary duct, and step (b) is performed by progressively stimulating the constricted wall portion to cause progressive contraction of the wall portion to move the bile and/or gall stones in the lumen. The constricted wall portion is progressively stimulated in the downstream or upstream direction of the lumen.

3) Step (a) is performed by varyingly constricting the wall portion to vary the movement of bile and/or gallstones in the biliary duct, and step (b) is performed by progressively stimulating the constricted wall portion to cause progressive contraction of the wall portion to move the bile and/or gall stones in the lumen. The constricted wall portion is progressively stimulated in the downstream or upstream direction of the lumen.

4) Step (a) is performed by varyingly constricting different areas of the wall portion to cause progressive constriction of the wall portion in the downstream or upstream direction of the lumen, and the constricted wall portion is progressively stimulated to cause progressive contraction thereof in harmony with the progressive constriction of the wall portion. The method may further comprise providing at least one elongated constriction element extending along the wall portion, and controlling the elongated constriction element to progressively constrict the wall portion in the downstream or upstream direction of the lumen. The elongated constriction element suitably comprises contact surfaces dimensioned to contact a length of wall portion, and the method may further comprise providing a plurality of stimulation elements distributed along the contact surfaces, and controlling the stimulation elements to stimulate the different areas of the wall portion along the length of the wall portion.

5) Step (a) is performed by constricting any one of a series of wall portions of the tissue wall to at least restrict the movement of bile and/or gallstones in the biliary duct, and step (b) is performed by stimulating the constricted wall portion to close the lumen. The method further comprises successively constricting the wall portions of the series of wall portions to move the bile and/or gall stones in the lumen in a peristaltic manner.

5a) In accordance with an alternative, the method further comprises providing at least one constriction element and at least one stimulation element positioned on the constriction element, moving the constriction element along the organ in the flow direction in the lumen to successively constrict the wall portions of the series of wall portions, and using the stimulation element to stimulate the wall portion constricted by the constriction element to close the lumen. Suitably, the method further comprises cyclically moving the constriction element along the wall portions of the series of wall portions.

5b) In accordance with another alternative, the method further comprises providing a plurality of constriction elements and stimulation elements positioned on the constriction elements, moving each constriction element along the biliary duct to successively constrict the wall portions of the series of wall portions, and using the stimulation elements to stimulate the wall portion constricted by any one of the constriction elements to close the lumen. Suitably, the method further comprises cyclically moving the constriction elements one after the other along the wall portions of the series of wall portions. Specifically, the method further comprises providing a rotor carrying the constriction elements, and rotating the rotor so that each constriction element cyclically constricts the wall portions of the series of wall portions. Each constriction element suitably comprises a roller that rolls on the biliary duct to constrict the latter.

6) Step (a) is performed by constricting any wall portions of a series of wall portions of the tissue wall of the organ, respectively, wherein the wall portions of the series of wall portions are successively constricted along the biliary duct to move the bile and/or gall stones in the lumen of the patient's biliary duct. The stimulation step (b) is performed by stimulating any constricted wall portions of the series of wall portions.

7) Step (a) is performed by constricting wall portions of a series of wall portions without completely closing the biliary duct, and step (b) is performed by stimulating the constricted wall portions one after the other, so that the wall portions of the series of wall portions are successively contracted along the biliary duct to move the bile and/or gall stones in the lumen of the patient's biliary duct.

8) Step (a) is performed by constricting the wall portion at an upstream or downstream end thereof to close the lumen. The method further comprises (c) constricting the wall portion between the upstream and downstream ends thereof, to move the bile and/or gallstones contained in the wall portion between the upstream and downstream ends thereof downstream or upstream in the biliary duct. Optionally, the method further comprises stimulating the wall portion between the upstream and downstream ends thereof, as (c) is performed.

8a) In accordance with an alternative, step (a) is performed by constricting the wall portion at the upstream end thereof to restrict the movement of bile and/or gallstones in the biliary duct, and step (b) is performed by stimulating the constricted wall portion at the upstream end to close the biliary duct, whereby the bile and/or gall stones contained in the wall portion between the upstream and downstream ends thereof is moved downstream in the biliary duct, as step (c) is performed.

8b) In accordance with another alternative, step (a) is performed by constricting the wall portion at the downstream end thereof to restrict the movement of bile and/or gallstones in the biliary duct, and step (b) is performed by stimulating the constricted wall portion at the downstream end to close the biliary duct, whereby the bile and/or gall stones contained in the wall portion between the upstream and downstream ends thereof is moved upstream in the biliary duct, as step (c) is performed. This can be used to release gallstones that are stuck in the biliary ducts. These gallstones are subsequently moved downstream, towards the duodenum.

As the biliary duct is tubular in shape, a particularly long wall portion of the biliary duct may be surgically prepared to extend in zigzag with adjacent walls stitched together by two parallel rows of stitches and with the adjacent walls cut through between the two rows of stitches. As a result, the lumen of this long wall portion of the biliary duct can be significantly expanded. In this case, a considerably larger volume of fluid is moved in the biliary duct each time step (a) and/or step (b) is performed.

In any of the above noted embodiments (1) to (8b), step (b) may be performed by stimulating the wall portion with electric pulses.

Importantly, in any of the embodiments above, movement of bile and/or gallstones can be carried out with electric stimulation only. Thus, in such an embodiment, there is no constriction device.

Stimulation Modes

When stimulating neural or muscular tissue there is a risk of injuring or deteriorating the tissue over time if the stimulation is not properly performed. The method of the present invention is performed to reduce or even eliminate that risk. Thus, step (b) is performed by intermittently stimulating different areas of the wall portion so that at least two of the areas are stimulated at different points of time. I.e., the stimulation is shifted from one area to another area over time. In addition, step (b) is performed by intermittently stimulating the areas of the wall portion so that an area of the different areas that currently is not stimulated has time to restore substantially normal blood circulation before it is stimulated again. Furthermore, step (b) is performed by intermittently stimulating the areas during successive time periods, wherein each time period is short enough to maintain satisfactory blood circulation in the area until the laps of the time period. This gives the advantage that the method of the present invention provides continuous stimulation of the wall portion of the biliary duct to achieve the desired flow control while essentially maintaining over time the natural physical properties of the biliary duct without risk of injuring the biliary duct.

Also, by physically changing the places of stimulation on the biliary duct over time as described above it is possible to create an advantageous changing stimulation pattern on the biliary duct, in order to achieve a desired flow control.

To achieve the desired reaction of the tissue wall during the stimulation thereof, step (b) may be performed by stimulating the wall portion with, preferably cyclically, varying stimulation intensity.

In a main embodiment of the invention, step (b) is performed by intermittently stimulating the wall portion with pulses, preferably in the form of pulse trains. The pulse trains can be configured in many different ways by varying pulse parameters. Thus, the pulse amplitudes of the pulses of the pulse trains, the off time periods between the individual pulses of each pulse train and the width and repetition frequency of each pulse may be varied. Also the off time periods between the pulse trains may be varied, wherein each off time period between the pulse trains is kept long enough to restore substantially normal blood circulation in each area of the wall portion, when the area is not stimulated during the off time periods. Furthermore, the repetition frequency of the pulses of the pulse trains and the length and number of pulses of each pulse train may be varied.

As mentioned above, for reasons of maintaining over time the effect of stimulation, it is preferable that different areas of the wall portion are intermittently and individually stimulated. In consequence, step (b) may be performed by stimulating one or more of the areas at a time with pulses, by cyclically propagating the stimulation of the areas with pulses along the wall portion, and/or by propagating the stimulation of the areas with pulses in accordance with a determined stimulation pattern. In case the off time periods between pulse trains that stimulate the respective area of the wall portion are varied, it is preferable that each off time period between the pulse trains is controlled to last long enough to restore substantially normal blood circulation in the area when the latter is not stimulated during the off time periods.

Electric Stimulation

In accordance with a preferred embodiment of the invention, step (b) is performed by electrically stimulating the wall portion, preferably with electric pulses to cause contraction of the wall portion. This embodiment is particularly suited for applications in which the patient's wall portion includes muscle fibers that react to electrical stimula. Thus, the wall portion that includes the muscle fibers is stimulated with such electric pulses, preferably in the form of electric pulse trains, when the wall portion is in the constricted state, to cause contraction of the wall portion. Of course, the configuration of the electric pulse trains may be similar to the above described pulse trains and different areas of the wall portion may be electrically stimulated in the same manner as described above.

In accordance with the preferred embodiment, the method of the invention comprises providing at least one, preferably a plurality of electrical elements, such as electrodes, engaging and stimulating the wall portion with electric pulses. Optionally, the electrical elements may be placed in a fixed orientation relative to one another. The method comprises electrically energizing the electrical elements, preferably by cyclically energizing each element with electric pulses. The electrical elements may be energized so that the electrical elements are energized one at a time in sequence, or so that a number or groups of the electrical elements are energized at a time. Also, groups of electrical elements may be sequentially energized, either randomly or in accordance with a predetermined pattern.

The method may further comprise applying the electrical elements on the patient's wall portion so that the electrical elements form any pattern of electrical elements, preferably an elongate pattern of electrical elements extending lengthwise along the wall portion and the elements abut the respective areas of the wall portion. The electrical elements may be successively energized along the elongate pattern of electrical elements in a direction opposite to or in the same direction as that of the flow in the patient's biliary duct. Optionally, the electrical elements may be successively energized along the elongate pattern of electrical elements from a position substantially at the center of the constricted wall portion towards both ends of the elongate pattern of electrical elements. Where the lumen of the biliary duct is to be kept closed for a relatively long time, the electrical elements may be energized so that energized electrical elements form two waves of energized electrical elements that simultaneously advance from the center of the constricted wall portion in two opposite directions towards both ends of the elongate pattern of electrical elements. Such waves of energized electrical elements can be repeated over and over again without harming the biliary duct and without moving matter in any direction in the lumen of the biliary duct.

The elongate pattern of electrical elements may include one or more rows of electrical elements extending lengthwise along the biliary duct. Each row of electrical elements may form a straight, helical or zig-zag path of electrical elements, or any form of path. The electrical elements may be energized so that the electrical elements currently energized form at least one group of adjacent energized electrical elements, wherein the elements in the group of energized electrical elements form a path of energized electrical elements extending at least in part around the patient's biliary duct, preferably completely around the patient's biliary duct. Alternatively, the elements in the group of energized electrical elements form two paths of energized electrical elements extending on mutual sides of the patient's biliary duct or more than two paths of energized electrical elements extending on different sides of the patient's biliary duct, preferably at least substantially transverse to the flow direction in the lumen of the biliary duct.

In an embodiment of the invention, the electrical elements form a plurality of groups of elements, wherein the groups form a series of groups extending along the patient's biliary duct in the flow direction in the patient's biliary duct. The electrical elements of each group of electrical elements may form a path of elements extending at least in part around the patient's biliary duct. In a first alternative, the electrical elements of each group of electrical elements may form more than two paths of elements extending on different sides of the patient's biliary duct, preferably substantially transverse to the flow direction in the patient's biliary duct. The groups of electrical elements in the series of groups may be energized in random or in accordance with a predetermined pattern. Alternatively, the groups of electrical elements in the series of groups may be successively energized in a direction opposite to or in the same direction as that of the flow in the patient's biliary duct, or in both said directions starting from a position substantially at the center of the constricted wall portion. For example, groups of energized electrical elements may form advancing waves of energized electrical elements, as described above. I.e., the groups of electrical elements may be energized so that energized electrical elements form two waves of energized electrical elements that simultaneously advance from the center of the constricted wall portion in two opposite directions towards both ends of the elongate pattern of electrical elements.

Thermal Stimulation

In accordance with an embodiment of the invention, stimulation step (b) is performed by thermally stimulating the wall portion. Thus, the wall portion may be cooled, when the wall portion is constricted, to cause contraction of the wall portion. For example, the wall portion may be constricted to at least restrict the movement of bile and/or gallstones in the biliary duct, and the constricted wall portion may be cooled to cause contraction thereof, so that the movement of bile and/or gallstones in the biliary duct is at least further restricted, or further restricted but not stopped, or stopped. Alternatively, the wall portion may be heated, when the wall portion is constricted and contracted, to cause expansion of the wall portion. Where the wall portion includes a blood vessel, the blood vessel may be cooled to cause contraction thereof, or heated to cause expansion thereof. Where applicable, thermal stimulation may be practised in any of the embodiments of the present invention. Where applicable, thermal stimulation may be practised in any of the embodiments of the present invention, and the thermal stimulation may be controlled in response to various sensors, for example strain, motion or pressure sensors.

Constriction and Stimulation Devices

Generally, the method of the invention comprises providing a constriction device that constricts the wall portion, a stimulation device that stimulates the constricted wall portion and a control device that controls the constriction device and/or the stimulation device. The method comprises operating the control device from outside the patient's body, preferably by using the control device to wirelessly control the constriction device and/or stimulation device. The wireless control is preferably performed in a non-magnetic manner, whereby implanted magnetic devices can be avoided. Suitably, the control device comprises a hand-held wireless remote control operated by the patient.

Alternatively, the control device comprises a manually operable switch for switching on and off the constriction device and/or stimulation device. In this case, the method comprises subcutaneously implanting the switch in the patient and manually operating the implanted switch from outside the patient's body.

In an embodiment of the invention, the control device comprises a programmable internal control unit, such as a microprocessor, and the method comprises implanting in the patient the internal control unit and controlling by the internal control unit the constriction device and/or stimulation device. The control device may also comprise an external control unit outside the patient's body. In this case, the method comprises controlling by the external control unit the constriction device and/or stimulation device and, optionally, using the external control unit to program the implanted internal control unit. The internal control unit may be programmable for controlling the constriction device and/or stimulation device over time, for example in accordance with an activity schedule program.

The constriction of the wall portion can be calibrated by using the control device to control the stimulation device to stimulate the wall portion while controlling the constriction device to adjust the constriction of the wall portion until the desired restriction of the movement of bile and/or gallstones in the biliary duct is obtained.

Sensor Controlled Constriction and/or Stimulation

In an embodiment of the invention, the method comprises implanting at least one sensor and controlling by the control device the constriction device and/or the stimulation device in response to signals from the sensor. Generally, the sensor directly or indirectly senses at least one physical parameter of the patient, functional parameter of the apparatus, or functional parameter of a medical implant in the patient.

Many different kinds of sensor for sensing physical parameters may be used. For example motion sensors for sensing biliary duct motion, natural contractions, such as stomach or intestinal contractions, pressure sensors for sensing pressure in the biliary duct, strain sensors for sensing strain of the biliary duct, flow sensors for sensing fluid movement of bile and/or gallstones in the biliary duct of the biliary duct, spectro-photometrical sensors, Ph-sensors for acidity or alkalinity of the fluid in the lumen of the biliary duct, oxygen-sensors sensors for sensing the oxygen content of the fluid in the lumen of the biliary duct, or sensors for sensing the distribution of the stimulation on the stimulated biliary duct. Any conceivable sensors for sensing any other kind of useful physical parameter may be used.

Many different kinds of sensors that sense functional parameters of implanted components may also be used for the control of the constriction device and/or the stimulation device. For example sensors for sensing electric parameters of implanted electric components, or sensors for sensing the performance of implanted motors or the like.

The sensor may comprise a pressure sensor for sensing as the physical parameter a pressure in the patient's body that relates to the pressure in the lumen of the patient's biliary duct. In this case, the method suitably comprises operating the control device to control the constriction device to change the constriction of the patient's wall portion in response to the pressure sensor sensing a predetermined value of measured pressure.

Alternatively, or in combination with the pressure sensor, a position sensor may be provided for sensing as the physical parameter the orientation of the patient with respect to the horizontal. The position sensor may be a biocompatible version of what is shown in U.S. Pat. Nos. 4,942,668 and 5,900,909. For example, the control device may control the constriction device and/or stimulation device to change the constriction of the patient's wall portion in response to the position sensor sensing that the patient has assumed a substantially horizontal orientation, i.e. that the patient is lying down.

The above described sensors may be used in any of the embodiments of the invention, where applicable.

The control device may control the constriction device and/or stimulation device to change the constriction of the patient's wall portion in response to the time of day. For that purpose the control device may include a clock mechanism for controlling the constriction device and/or stimulation device to change the constriction of the patient's wall portion to increase or decrease the influence on the movement of bile and/or gallstones in the biliary duct during different time periods of the day. In case a sensor of any of the above-described types for sensing a physical or functional parameter is provided, either the clock mechanism is used for controlling the constriction device and/or stimulation device provided that the parameter sensed by the sensor does not override the clock mechanism, or the sensor is used for controlling the constriction device and/or stimulation device provided that the clock mechanism does not override the sensor. Suitably, the control device produces an indication, such as a sound signal or displayed information, in response to signals from the sensor.

The control device may comprise an implantable internal control unit that directly controls the constriction device and/or stimulation device in response to signals from the sensor. The control device may further comprise a wireless remote control adapted to set control parameters of the internal control unit from outside the patient without mechanically penetrating the patient. At least one of the control parameters, which is settable by the wireless remote control, is the physical or functional parameter. Suitably, the internal control unit includes the above mentioned clock mechanism, wherein the wireless remote control also is adapted to set the clock mechanism. Alternatively, the control device may comprise an external control unit outside the patient's body for controlling the constriction device and/or stimulation device in response to signals from the sensor.

Constriction of the Patient's Biliary Duct

Method step (a) may be performed in many different ways. Thus, step (a) may be performed by:
(1)—constricting the wall portion so that the through-flow area of the biliary duct assumes a size in the constricted state small enough to cause the constricted wall portion to contract to stop the movement of bile and/or gallstones in the biliary duct when step (b) is performed;
(2)—bending the wall portion;
(3)—clamping the wall portion between at least two elements positioned on different sides of the biliary duct;
(4)—clamping the biliary duct between an element and the bone or tissue of the patient;
(5)—rotating at least two elements positioned on different sides of the biliary duct; or
(6)—clamping the biliary duct between at least two articulated clamping elements positioned on different sides of the biliary duct.

In the above noted alternatives (1) to (6) of method step (a), the constriction of the wall portion of the biliary duct may be changed either mechanically or hydraulically. For many applications of the present invention, step (a) is suitably performed so that the through-flow area of the biliary duct assumes a size in the constricted state that is small enough to enable the stimulation during step (b) to contract the wall portion of the biliary duct to stop the movement of bile and/or gallstones in the biliary duct.

Where the constriction of the wall portion is hydraulically changed, the method of the invention may further comprise implanting in the patient a reservoir containing a predetermined amount of hydraulic fluid, and a constriction device engaging the wall portion and having an expandable/contractible cavity, wherein step (a) is performed by distributing hydraulic fluid from the reservoir to increase the volume of the cavity to constrict the wall portion, and by distributing hydraulic fluid from the cavity to the reservoir to decrease the volume of the cavity to release the wall portion. The cavity may be defined by a balloon of the constriction device that abuts the tissue wall portion of the patient's biliary duct, so that the patient's wall portion is constricted upon expansion of the cavity and released upon contraction of the cavity.

Alternatively, the cavity may be defined by a bellows that displaces a relatively large contraction element of the constriction device, for example a large balloon that abuts the wall portion, so that the patient's wall portion is constricted upon contraction of the bellows and released upon expansion of the bellows. Thus, a relatively small addition of hydraulic fluid to the bellows causes a relatively large increase in the constriction of the wall portion. Such a bellows may also be replaced by a suitably designed piston/cylinder mechanism.

Where the hydraulic means comprises a cavity in the constriction device, the following embodiments of the invention are conceivable.

1) The reservoir comprises first and second wall portions, and step (a) is performed by displacing the first and second wall portions relative to each other to change the volume of the reservoir, so that fluid is distributed from the reservoir to the cavity, or from the cavity to the reservoir.

1a) At least one of a magnetic device, a hydraulic device or an electric control device displaces the first and second wall portions of the reservoir.

2) A pump is provided for pumping fluid between the reservoir and the cavity.

2a) The pump comprises a first activation member for activating the pump to pump fluid from the reservoir to the cavity and a second activation member for activating the pump to pump fluid from the cavity to the reservoir.

2a1) The first and second activation members are operable by manual manipulation thereof.

2a2) At least one of the activation members operates when subjected to an external predetermined pressure.

2a3) At least one of the first and second activating members is operable by magnetic means, hydraulic means, or electric control means.

2b) A fluid conduit between the pump and the cavity is provided, wherein the reservoir forms part of the conduit. The conduit and pump are devoid of any non-return valve. The reservoir forms a fluid chamber with a variable volume, and the pump distributes fluid from the chamber to the cavity by a reduction in the volume of the chamber and withdraws fluid from the cavity by an expansion of the volume of the chamber. A motor is provided for driving the pump, wherein the pump comprises a movable wall of the reservoir for changing the volume of the chamber.

In all of the above noted embodiments 1 to 2b where the hydraulic means comprises an expandable cavity in the constriction device, the cavity can be exchanged by a cylinder/piston mechanism for adjusting the constriction device. In this case, hydraulic fluid is distributed between the reservoir and the cylinder/piston mechanism to adjust the constriction device.

3) The method further comprises implanting a reverse servo operatively connected to the hydraulic means. The term "reverse servo" is to be understood as a mechanism that transfers a strong force acting on a moving element having a short stroke into a weak force acting on another moving element having a long stroke; i.e., the reverse function of a normal servo mechanism. Thus, minor changes in the amount of fluid in a smaller reservoir could be transferred by the reverse servo into major changes in the amount of fluid in a larger reservoir.

Preferably, the reverse servo comprises an expandable servo reservoir containing servo fluid and a fluid supply reservoir hydraulically connected to the servo reservoir to form a closed conduit system for the servo fluid. The expandable servo reservoir has first and second wall portions, which are displaceable relative to each other in response to a change in the volume of the expandable servo reservoir.

In accordance with a first alternative, the first and second wall portions of the servo reservoir are operatively connected to the hydraulic means. The reverse servo distributes fluid between the fluid supply reservoir and the expandable servo reservoir to change the volume of the servo reservoir, whereby the hydraulic means is operated to adjust the constriction device.

In accordance with a second alternative, there is provided an implantable main reservoir containing a predetermined amount of hydraulic fluid, wherein the reverse servo is operated to distribute hydraulic fluid between the main reservoir and the hydraulic means to adjust the constriction device. More specifically, the main reservoir is provided with first and second wall portions operatively connected to the first and second wall portions of the expandable servo reservoir, so that the volume of the main reservoir is changed when the volume of the expandable servo reservoir is changed. Thus, when the reverse servo distributes servo fluid between the fluid supply reservoir and the expandable servo reservoir to change the volume of the main reservoir, hydraulic fluid is distributed from the main reservoir to the hydraulic means, or from the hydraulic means to the main reservoir. Advantageously, the method comprises dimensioning the servo and main reservoirs, so that when the volume of the servo reservoir is changed by a relatively small amount of servo fluid, the volume of the main reservoir is changed by a relatively large amount of hydraulic fluid.

In both of the above-described alternatives, the fluid supply reservoir may have first and second wall portions, which are displaceable relative to each other to change the volume of the fluid supply reservoir to distribute servo fluid between the fluid supply reservoir and the expandable servo reservoir. The first and second wall portions of the fluid supply reservoir may be displaced relative to each other by manual manipulation, a magnetic device, a hydraulic device, or an electric control device to change the volume of the fluid supply reservoir to distribute servo fluid between the fluid supply reservoir and the expandable servo reservoir.

In all of the above noted embodiments 1 to 2b where the hydraulic means comprises an expandable cavity in the constriction device, or in embodiments where the hydraulic means includes a hydraulically operable mechanical construction, the reverse servo described above may be used. In a further embodiment of the invention, the hydraulic means include first and second hydraulically interconnected expandable/contractible reservoirs. The first reservoir is operatively connected to the constriction device, so that the constriction device changes the constriction of the patient's wall portion upon expansion or contraction of the first reservoir. By changing the volume of the second reservoir hydraulic fluid is distributed between the two reservoirs, so that the first reservoir is either expanded or contracted. This embodiment requires no non-return valve in the fluid communication conduits between the two reservoirs, which is beneficial to long-term operation of the hydraulic means.

Alternatively, the hydraulic means may include first and second hydraulically interconnected piston/cylinder mechanisms instead of the first and second reservoirs described above. The first piston/cylinder mechanism is operatively connected to the constriction device, so that the constriction device changes the constriction of the patient's wall portion upon operation of the first piston/cylinder mechanism. By operating the second piston/cylinder mechanism hydraulic fluid is distributed between the two piston/cylinder mechanisms, so that the first piston/cylinder mechanism adjusts the constriction device.

Where the constriction device does not include an expandable/contractible cavity, the constriction device may comprise at least two elongated clamping elements extending along the wall portion on different sides of the biliary duct. The hydraulic means, which may include the reverse servo described above, hydraulically moves the elongated clamping elements towards the biliary duct to constrict the wall portion of the biliary duct. For example, the constriction device may have hydraulic chambers in which the clamping elements slide back and forth, and the hydraulic means may also include a pump and an implantable reservoir containing hydraulic fluid. The pump distributes hydraulic fluid from the reservoir to the chambers to move the clamping elements against the wall portion, and distributes hydraulic fluid from the chambers to the reservoir to move the clamping elements away from the wall portion.

Energy Supply

Generally, method step (a) is performed by using the constriction device and step (b) is performed by using the stimulation device, wherein the method further comprises forming the constriction and stimulation devices in an operable constriction/stimulation unit.

In a simple form of the invention, the method comprises implanting a source of energy, such as a battery, rechargeable battery or accumulator, releasing energy from the source of energy and using the released energy in connection with the operation of the constriction/stimulation unit.

In a more sophisticated form of the invention, which is preferable, the method comprises transmitting wireless energy from outside the patient's body to inside the patient's body and using the transmitted wireless energy in connection with the operation of the constriction/stimulation unit.

Transmission of Wireless Energy

The wireless energy may be directly used in connection with the operation of the constriction/stimulation unit, as the wireless energy is being transmitted. For example, the wireless energy may be transmitted in the form of an electric, an electromagnetic or a magnetic field, or a combination thereof, or electromagnetic waves for direct power of the constriction/stimulation unit. For example, where an electric motor or pump operates the constriction device of the constriction/stimulation unit, wireless energy in the form of a magnetic or an electromagnetic field may be used for direct power of the motor or pump.

Thus, the motor or pump is running directly during transmission of the wireless energy. This may be achieved in two different ways: a) using a transforming device implanted in the patient to transform the wireless energy into energy of a different form, preferably electric energy, and powering the motor or pump with the transformed energy, or b) using the wirelessly transmitted energy to directly power the motor or pump. Preferably wireless energy in the form of an electromagnetic or magnetic field is used to directly influence specific components of the motor or pump to create kinetic energy. Such components may include coils integrated in the motor or pump.

The wireless energy is suitably transmitted in pulses or digital pulses, or a combination of pulses and digital pulses.

Preferably, the wireless energy is transmitted in at least one wireless signal, suitably a wave signal. The wave signal may comprise an electromagnetic wave signal including one of an infrared light signal, a visible light signal, an ultra violet light signal, a laser signal, a microwave signal, a radio wave signal, an x-ray radiation signal, and a gamma radiation signal. Alternatively, the wave signal may comprise a sound or an ultrasound wave signal. The wireless signal may be a digital or analogue signal, or a combination of a digital and analogue signal.

In accordance with a particular embodiment of the invention, the wireless energy is not for direct use in connection with the operation of the constriction/stimulation unit. In this embodiment the wireless energy comprises energy of a first form, which is transmitted into energy of a second form suited to operate the constriction/stimulation unit. Typically, the energy of the second form is different from the energy of the first form. For example, the wireless energy of the first form may comprise sound waves, whereas the energy of the second form may comprise electric energy. Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

Transforming Wireless Energy

In accordance with a particular embodiment of the invention, an implantable energy-transforming device is provided for transforming wireless energy of a first form transmitted by the energy-transmission device into energy of a second form, which typically is different from the energy of the first form. The constriction/stimulation unit is operable in response to the energy of the second form. For example, the wireless energy of the first form may comprise sound waves, whereas the energy of the second form may comprise electric energy. Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

The energy-transforming device may function different from or similar to the energy-transmission device. Advantageously, the energy-transforming device comprises at least one element, such as at least one semiconductor, having a positive region and a negative region, when exposed to the energy of the first form transmitted by the energy-transmission device, wherein the element is capable of creating an energy field between the positive and negative regions, and the energy field produces the energy of the second form. More specifically, the element may comprise an electrical junction element, which is capable of inducing an electric field between the positive and negative regions when exposed to the energy of the first form transmitted by the energy-transmission device, whereby the energy of the second form comprises electric energy.

The energy of the first form may directly or indirectly be transformed into the energy of the second form. The method of the invention may comprise providing a motor for operating the constriction device and powering the motor with the energy of the second form. The constriction device may be operable to perform at least one reversible function and the method may comprise reversing the function by using the motor. For example, the method may comprise shifting the polarity of the energy of the second form to reverse the motor.

The motor may be directly powered with the transformed energy, as the energy of the second form is being transformed from the energy of the first form. Preferably, the constriction/stimulation unit is directly operated with the energy of the second form in a non-magnetic, non-thermal or non-mechanical manner.

Normally, the implanted constriction/stimulation unit comprises electric components that are energized with electrical energy. Therefore, the energy of the first form may be transformed into a direct current or pulsating direct current, or a combination of a direct current and pulsating direct current. Alternatively, the energy of the first form may be transformed into an alternating current or a combination of a direct and alternating current.

The method of the invention may comprise implanting in the patient an internal source of energy, and supplying energy from the internal source of energy for the operation of the constriction/stimulation unit. The method may further comprise implanting in the patient a switch operable to switch from an "off" mode, in which the internal source of energy is not in use, to an "on" mode, in which the internal source of energy supplies energy for the operation of the constriction/stimulation unit, and/or for energizing implanted electronic components of the constriction/stimulation unit. The switch may be operated by the energy of the first form or by the energy of the second form. The described switch arrangement reduces power consumption of the constriction/stimulation unit between operations.

The internal source of energy may store the energy of the second form. In this case, the internal source of energy suitably comprises an accumulator, such as at least one capacitor or at least one rechargeable battery, or a combination of at least one capacitor and at least one rechargeable battery. Where the internal source of energy is a rechargeable battery it may be charged only at times convenient for the patient, for example when the patient is sleeping. Alternatively, the internal source of energy may supply energy for the operation of the constriction/stimulation unit but not be used for storing the energy of the second form. In this alternative, the internal source of energy may be a battery and the switch described above may or may not be provided.

Suitably, the method of the invention may comprise implanting a stabilizer for stabilizing the energy of the second form. Where the energy of the second form comprises electric energy the stabilizer suitably comprises at least one capacitor.

The energy-transforming device may be designed for implantation subcutaneously in the abdomen, thorax or cephalic region of the patient. Alternatively, it may be designed for implantation in an orifice of the patient's body and under the mucosa or intramuscularly outside the mucosa of the orifice.

Control of Constriction/Stimulation Unit

Although the constriction device of the constriction/stimulation unit may normally keep the patient's wall portion in the constricted state, in most applications using the present invention there will be daily adjustments of the constriction device. Therefore, in a preferred embodiment of the invention, the constriction device is adjustable to enable changing the constriction of the patient's wall portion as desired and the control device controls the constriction device to change the constriction of the wall portion.

The method of the invention suitably comprises operating the control device by the patient. In a simple form the control device comprises a manually operable switch for switching on and off the constriction/stimulation unit, and the method further comprises subcutaneously implanting the switch in the patient. It is preferable, however, that the control device comprises a hand-held wireless remote control operable by the patient from outside the patient's body to control the constriction/stimulation unit to adjust the stimulation intensity and/or adjust the constriction of the wall portion. The wireless remote control is suitably designed for application on the patient's body like a wristwatch.

In some applications of the invention, the constriction device of the constriction/stimulation unit may be designed to normally keep the patient's wall portion in the constricted state. I.e., after implantation the constriction device all the time keeps the wall portion constricted. In this case, the control device may be used when needed, conveniently by the patient, to control the stimulation device of the constriction/stimulation unit to stimulate the constricted tissue wall portion, preferably while adjusting the stimulation intensity, to cause contraction of the wall portion, so that the movement of bile and/or gallstones in the biliary duct is at least further restricted or stopped, and to control the stimulation device to cease the stimulation. More precisely, the method of the invention may comprise operating the control device by the patient to a) control the stimulation device in a first mode to stimulate the constricted wall portion to further restrict the movement of bile and/or gallstones in the biliary duct and control the stimulation device in a second mode to cease the stimulation of the wall portion to increase the movement of bile and/or gallstones in the biliary duct; or b) control the stimulation device in a first mode to stimulate the constricted wall portion to stop the movement of bile and/or gallstones in the biliary duct and control the stimulation device in a second mode to cease the stimulation of the wall portion to allow movement of bile and/or gallstones in the biliary duct.

Either the first mode or the second mode may be temporary.

The wireless remote control preferably transmits at least one wireless control signal for controlling the constriction/stimulation unit. The control signal may comprise a frequency, amplitude, phase modulated signal or a combination thereof, and may be an analogue or a digital signal, or a combination of an analogue and digital signal. The remote control may transmit an electromagnetic carrier wave signal for carrying the digital or analogue control signal. Also the carrier signal may comprise digital, analogue or a combination of digital and analogue signals.

Any of the above signals may comprise wave signals, such as a sound wave signal, an ultrasound wave signal, an electromagnetic wave signal, an infrared light signal, a visible light signal, an ultra violet light signal, a laser light signal, a micro wave signal, a radio wave signal, an x-ray radiation signal or a gamma radiation signal.

Alternatively, the control signal may comprise an electric or magnetic field, or a combined electric and magnetic field.

Operation of Constriction/Stimulation Unit

The method of the invention may comprise implanting in the patient an operation device, and operating the constriction/stimulation unit with the operation device. A magnet may be provided, wherein the method comprises using the magnet to activate the operation device from outside the patient's body. The operation device suitably comprises a motor which is powered with energy released from a source of energy, such as a battery. Although the constriction/stimulation unit in embodiments described above suitably is designed as a single piece, which is most practical for implantation, it should be noted that as an alternative the constriction device and stimulation device of the constriction/stimulation unit could be designed as separate pieces.

Laparoscopic Method

The present invention also provides a laparoscopic method. Accordingly, there is provided a method for controlling a movement of bile and/or gallstones of bile and/or gall stones in the biliary duct. The methods comprises:

First: The method for controlling a movement of bile and/or gallstones in a biliary duct, the method comprising the steps of:

inserting a needle like tube into the abdomen of the patients body,
  filling the abdomen with gas thereby expanding the abdominal cavity,
  placing at least two laparoscopical trocars in the patient's body,
  inserting a camera through one of the trocars into the abdomen,
  inserting a dissecting tool through any of the trocar and dissecting an area of at least one portion of the tissue wall of the biliary duct,
  placing a constriction device and a stimulation device in the dissected area in operative engagement with the biliary duct,
  using the constriction device to gently constrict the wall portion of the biliary duct to influence the movement of bile and/or gallstones in the biliary duct, and
  using the stimulation device to stimulate the constricted wall portion to cause contraction of the wall portion to further influence the movement of bile and/or gallstones in the biliary duct.

Second: The method for controlling a movement of bile and/or gallstones in a biliary duct, the method comprising the steps of:

inserting a needle like tube into a cavity of the patients body,
  using the needle like tube to fill the cavity with gas thereby expanding the cavity,
  placing at least two laparoscopical trocars in the patient's body,
  inserting a camera through one of the trocars into the cavity,
  inserting a dissecting tool through any of the trocar and dissecting an area of at least one wall portion of a biliary duct,
  placing a flow influence device comprising, a stimulation device in the dissected area in operative engagement with the biliary duct, and
  using the stimulation device to stimulate the wall portion of the biliary duct to cause contraction of the wall portion to influence the movement of bile and/or gallstones in the biliary duct.

Third: The method for controlling a movement of bile and/or gallstones in a biliary duct, the method comprising the steps of:

inserting a needle like tube into a cavity of the patients body, using the needle like tube to fill the cavity with gas thereby expanding the cavity, placing at least two laparoscopical trocars in the patient's body, inserting a camera through one of the trocars into the cavity, inserting a dissecting tool through any of the trocar and dissecting an area of at least one wall portion of the biliary duct, placing a flow influence device comprising, a constriction device in the dissected area in operative engagement with the biliary duct, using the constriction device to constrict the wall portion of the biliary duct to influence the movement of bile and/or gallstones in the lumen.

Fourth: The method for controlling a movement of bile and/or gallstones in a lumen formed by a tissue wall of a patient's biliary duct, the method comprising the steps of:

cutting the skin of the patient, inserting a dissecting tool and dissecting an area of at least one portion of the tissue wall of the biliary duct, placing a flow influence device comprising, a constriction device and a stimulation device in the dissected area in operative engagement with the biliary duct, using the constriction device to gently constrict the wall portion of the organ to influence the movement of bile and/or gallstones in the lumen of the biliary duct, and using the stimulation device to stimulate the constricted wall portion to cause contraction of the wall portion of the biliary duct to further influence the movement of bile and/or gallstones in the lumen.

Fifth: The method for controlling a movement of bile and/or gallstones in a lumen formed by a tissue wall of a patient's biliary duct, the method comprising the steps of:

cutting the skin of the patient, inserting a dissecting tool and dissecting an area of at least one portion of the tissue wall of the biliary duct, placing a flow influence device comprising, a stimulation device in the dissected area in operative engagement with the biliary duct, and using the stimulation device to stimulate the wall portion to cause contraction of the wall portion of the biliary duct to influence the movement of bile and/or gallstones in the lumen.

Sixth: The method for controlling a movement of bile and/or gallstones in a lumen formed by a tissue wall of a patient's biliary duct, the method comprising the steps of:

cutting the skin of the patient, inserting a dissecting tool and dissecting an area of at least one portion of the tissue wall of the biliary duct, placing a flow influence device comprising, a constriction device in the dissected area in operative engagement with the biliary duct, and using the constriction device to constrict the wall portion of the biliary duct to influence the movement of bile and/or gallstones in the lumen.

The method according to any one of claim 225-230, wherein the cavity comprising; at least one of an abdominal cavity, a cavity in the pelvic region, a thoraxial cavity, a cavity in a limb, a cavity in human soft tissue, or muscle, or fat or fibrotic tissue.

The method further comprises implanting a powered operation device for operating the constriction device. The operation device may comprise a powered hydraulic operation device or an electrically powered operation device, such as an electric motor.

The method further comprises transmitting wireless energy for powering the operation device, and when desired to influence the flow in the patient's biliary duct, powering the operation device with the transmitted energy to operate the constriction device.

The method further comprises implanting a source of energy in the patient, providing an external source of energy, controlling the external source of energy to release wireless energy, transforming the wireless energy into storable energy, such as electric energy, non-invasively charging the implanted source of energy with the transformed energy, and controlling the implanted source of energy from outside the patient's body to release energy for use in connection with the operation of the constriction device and/or stimulation device. The wireless energy is transformed into a storable energy different from the wireless energy.

Alternatively, the method further comprises providing a source of energy outside the patient's body, controlling the external source of energy from outside the patient's body to release wireless energy, and using the released wireless energy for operating the constriction device and/or stimulation device. The wireless energy may be transformed into electrical energy inside the patient's body by an implanted energy-transforming device, wherein the electrical energy is used in connection with the operation of the constriction device and/or stimulation device. The electrical energy may be directly used in connection with the operation of the constriction device and/or stimulation device, as the transforming device transforms the wireless energy into the electrical energy. The external source of energy may be controlled from outside the patient's body to release non-magnetic wireless energy, wherein the released non-magnetic wireless energy is used for operating the constriction device and/or stimulation device. Alternatively, the external source of energy may be controlled from outside the patient's body to release electromagnetic wireless energy, wherein the released electromagnetic wireless energy is used for operating the constriction device and/or stimulation device.

Feed Back Related to the Wireless Energy

The following embodiments are related to feed back information related to an energy balance either comparing;

a) the amount of energy received by the internal energy source compared to the energy used by the constriction device and/or stimulation device, or b) The amount of energy received by the internal energy source and the amount of energy transmitted by the external energy source.

Several alternatives of the method of the present invention are disclosed below and may except being correlated directly to the constriction device and/or stimulation device also be included in the operating method. These methods are valid for use both with the stimulation device and constriction device separate or in combination.

A method for controlling the transmission of wireless energy comprising an internal energy source, wherein said wireless energy is transmitted from an external energy source located outside the patient and is received by the internal energy source located inside the patient, the internal energy source being connected to the constriction device and/or stimulation device for directly or indirectly supplying received energy thereto, the method comprising the steps of:

determining an energy balance between the energy received by the internal energy source and the energy used for the constriction device and/or stimulation device, and controlling the transmission of wireless energy from the external energy source, based on the determined energy balance.

A method, wherein the wireless energy is transmitted inductively from a primary coil in the external energy source to a secondary coil in the internal energy receiver.

A method, wherein a change in said energy balance is detected, and the transmission of wireless energy is controlled based on said detected energy balance change.

A method, wherein a difference is detected between energy received by said internal energy receiver and energy used for a medical device, and the transmission of wireless energy is controlled based on said detected energy difference.

A method, wherein the amount of transmitted wireless energy is decreased if the detected energy balance change implies that the energy balance is increasing, or vice versa.

A method, wherein the decrease/increase of energy transmission corresponds to a detected change rate.

A method, wherein the amount of transmitted wireless energy is decreased if the detected energy difference implies that the received energy is greater than the used energy, or vice versa.

A method, wherein the decrease/increase of energy transmission corresponds to the magnitude of said detected energy difference.

A method, wherein the energy used for the constriction device and/or stimulation device is stored in at least one energy storage device of the device.

A method, wherein substantially all the energy used for the constriction device and/or stimulation device i is consumed to operate the device.

A method, wherein the energy is consumed after being stabilised in at least one energy stabilising unit of the device.

A method, wherein the energy used for the constriction device and/or stimulation device is stored in at least one energy storage device of the device.

A method, wherein substantially all the energy used for the constriction device and/or stimulation device i is consumed to operate the device.

A method, wherein the energy is consumed after being stabilised in at least one energy stabilising unit of the device.

A method of controlling transmission of wireless energy supplied to the at least one of the stimulation and constriction devices, comprising an internal energy source located inside the patient, connected to the constriction device and/or stimulation device for directly or indirectly supplying received energy thereto, the method comprising the steps of:
   determining an energy balance between the energy sent by the external energy source and the energy received by the internal energy source, and
   controlling the transmission of wireless energy from the external energy source, based on the determined energy balance.

A method, wherein the wireless energy is transmitted inductively from a primary coil in the external energy source to a secondary coil in the internal energy receiver.

A method, wherein a change in said energy balance is detected, and the transmission of wireless energy is controlled based on said detected energy balance change.

A method, wherein a difference is detected between the energy sent by the external energy source and the energy received by said internal energy receiver, and the transmission of wireless energy is controlled based on said detected energy difference.

A method, wherein the amount of transmitted wireless energy is decreased if the detected energy balance change implies that the energy balance is increasing, or vice versa.

A method, wherein the decrease/increase of energy transmission corresponds to a detected change rate.

A method, wherein the amount of transmitted wireless energy is decreased if the detected energy difference implies that the received energy is greater than the used energy, or vice versa.

A method, wherein the decrease/increase of energy transmission corresponds to the magnitude of said detected energy difference.

A method of controlling transmission of wireless energy, wherein said wireless energy being transmitted by means of a primary coil in the external energy source and received inductively by means of a secondary coil in an internal energy source, the internal energy source being connected to the medical device for directly or indirectly supplying received energy thereto, wherein feedback control information (S) is transferred from the secondary coil to the primary coil by switching the secondary coil on and off to induce a detectable impedance load variation in the primary coil encoding the feedback control information, wherein the feedback control information relates to the energy received by the internal energy source and is used for controlling the transmission of wireless energy from the external energy source.

The method, wherein the electronic circuit comprises an analyzer analyzing the amount of energy being transmitted and receiving the feedback information related to the amount of energy received in the receiver, and determining the energy balance by comparing the amount of transmitted energy and the feedback information related to the amount of received energy.

The method, wherein the external energy source is adapted to use said feedback information adjusting the level of said transmitted energy.

A method of controlling transmission of wireless energy, wherein said wireless energy being transmitted by means of a primary coil in an external energy source and received inductively by means of a secondary coil in an internal energy source, the internal energy receiver being connected to the medical device for directly or indirectly supplying received energy thereto, wherein feedback control information (S) is transferred from the secondary coil to the primary coil by switching the secondary coil on and off to induce a detectable impedance load variation in the primary coil encoding the feedback control information, where the feedback control information relates to said energy balance.

BRIEF DESCRIPTION OF THE DRAWINGS

FIGS. 1F, 1G and 1H illustrate different states of operation of a modification of the general embodiment.

FIGS. 1I, 1K and 1L illustrate an alternative mode of operation of the modification of the general embodiment.

FIG. 14 illustrates an apparatus used for practicing the method of the invention where the apparatus is applied on the common bile duct.

DETAILED DESCRIPTION OF THE INVENTION

Figure 1A:
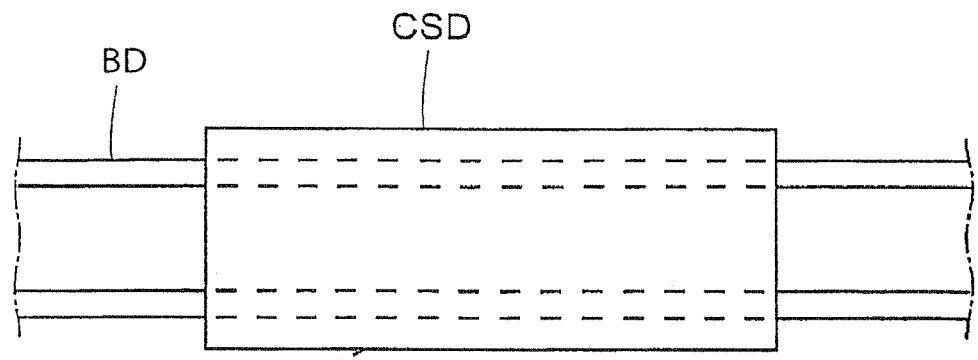
FIGS. 1A, 1B, 1C, 1D and 1E schematically illustrate different states of operation of a general embodiment of an apparatus used for practicing the method according to the present invention.

Referring to the drawing figures, like reference numerals designate identical or corresponding elements throughout the several figures.

Figure 1B:
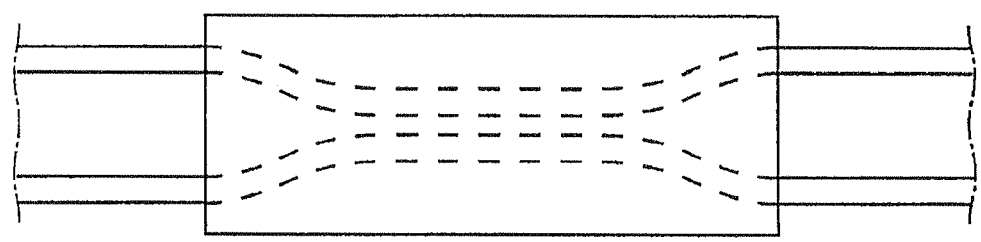
Figure 1C:
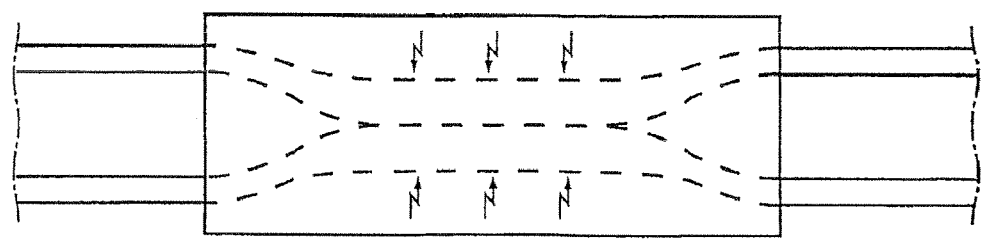

FIGS. 1A, 1B and 1C schematically illustrate different states of operation of a generally designed apparatus used for practicing the method of the present invention, when the apparatus is applied on a wall portion of a biliary duct designated BD. The apparatus includes a constriction device and a stimulation device, which are designated CSD, and a control device designated CD for controlling the constriction and stimulation devices CSD. FIG. 1A shows the apparatus in an inactivation state, in which the constriction device does not constrict the biliary duct BD and the stimulation device does not stimulate the biliary duct BD. FIG. 1B shows the apparatus in a constriction state, in which the control device CD controls the constriction device to gently constrict the wall portion of the biliary duct BD to a constricted state, in which the blood circulation in the constricted wall portion is substantially unrestricted and the movement of bile and/or gallstones in the biliary duct of the wall portion is restricted. FIG. 1C shows the apparatus in a stimulation state, in which the control device CD controls the stimulation device to stimulate different areas of the constricted wall portion, so that the wall portion of the biliary duct BD contracts (thickens) and closes the biliary duct.

Figure 1D:
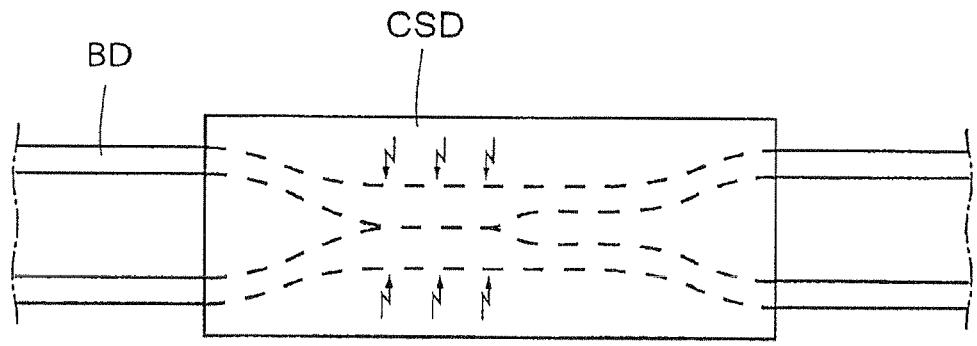
Figure 1E:
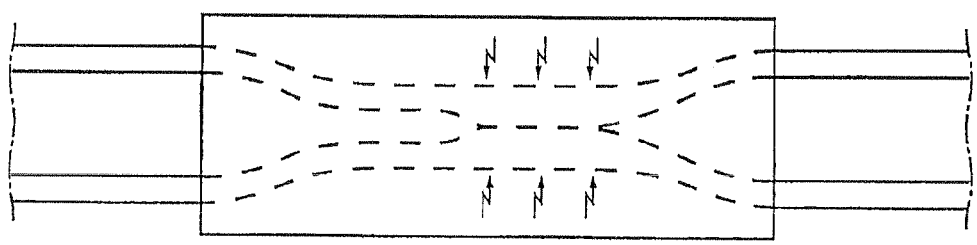

FIGS. 1D and 1E show how the stimulation of the constricted wall portion can be cyclically varied between a first stimulation mode, in which the left area of the wall portion (see FIG. 1D) is stimulated while the right area of the wall portion is not stimulated, and a second stimulation mode, in which the right area of the wall portion (see FIG. 1E) is stimulated while the left area of the wall portion is not stimulated, in order to maintain over time satisfactory blood circulation in the constricted wall portion. In addition, the FIGS. 1D and 1E show how electric stimulation can be used to move bile and/or gallstones in the biliary duct.

It should be noted that the stimulation modes shown in FIGS. 1D and 1E only constitute a principle example of how the constricted wall portion of the biliary duct BD may be stimulated. Thus, more than two different areas of the constricted wall portion may be simultaneously stimulated in cycles or successively stimulated. Also, groups of different areas of the constricted wall portion may be successively stimulated.

FIGS. 1F, 1G and 1H illustrate different states of operation of a modification of the general embodiment shown in FIGS. 1A-1E, wherein the constriction and stimulation devices CSD include several separate constriction/stimulation elements, here three elements CSDE1, CSDE2 and CSDE3. FIG. 1F shows how the element CSDE1 in a first state of operation is activated to both constrict and stimulate the biliary duct BD, so that the lumen of the biliary duct BD is closed, whereas the other two elements CSDE2 and CSDE3 are inactivated. FIG. 1G shows how the element CSDE2 in a second following state of operation is activated, so that the lumen of the biliary duct BD is closed, whereas the other two elements CSDE1 and CSDE3 are inactivated. FIG. 1H shows how the element CSDE3 in a following third state of operation is activated, so that the lumen of the biliary duct BD is closed, whereas the other two elements CSDE1 and CSDE2 are inactivated. By shifting between the first, second and third states of operation, either randomly or in accordance with a predetermined sequence, different portions of the biliary duct can by temporarily constricted and stimulated while maintaining the lumen of the biliary duct closed, whereby the risk of injuring the biliary duct is minimized. It is also possible to activate the elements CSDE1-CSDE3 successively along the lumen of the biliary duct to move bile and/or gallstones in the lumen.

FIGS. 1I, 1K and 1L illustrate an alternative mode of operation of the modification of the general embodiment. Thus, FIG. 1I shows how the element CSDE1 in a first state of operation is activated to both constrict and stimulate the biliary duct BD, so that the lumen of the biliary duct BD is closed, whereas the other two elements CSDE2 and CSDE3 are activated to constrict but not stimulate the biliary duct BD, so that the lumen of the biliary duct BD is not completely closed where the elements CSDE2 and CSDE3 engage the biliary duct BD. FIG. 1K shows how the element CSDE2 in a second following state of operation is activated to both constrict and stimulate the biliary duct BD, so that the lumen of the biliary duct BD is closed, whereas the other two elements CSDE1 and CSDE3 are activated to constrict but not stimulate the biliary duct BD, so that the lumen of the biliary duct BD is not completely closed where the elements CSDE1 and CSDE3 engage the biliary duct BD. FIG. 1L shows how the element CSDE3 in a following third state of operation is activated to both constrict and stimulate the biliary duct BD, so that the lumen of the biliary duct BD is closed, whereas the other two elements CSDE1 and CSDE2 are activated to constrict but not stimulate the biliary duct BD, so that the lumen of the biliary duct BD is not completely closed where the elements CSDE1 and CSDE2 engage the biliary duct BD. By shifting between the first, second and third states of operation, either randomly or in accordance with a predetermined sequence, different portions of the biliary duct can by temporarily stimulated while maintaining the lumen of the biliary duct closed, whereby the risk of injuring the biliary duct is reduced. It is also possible to activate the stimulation of the elements CSDE1-CSDE3 successively along the lumen of the biliary duct BD to move bile and/or gallstones in the biliary duct.

Figure 3:
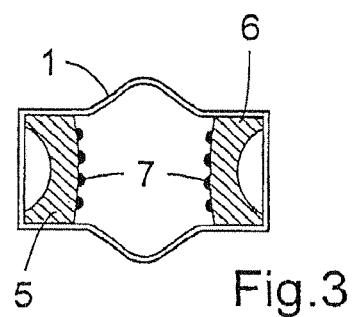
FIG. 3 is a cross-section along line II-II in FIG. 2.
Figure 2:
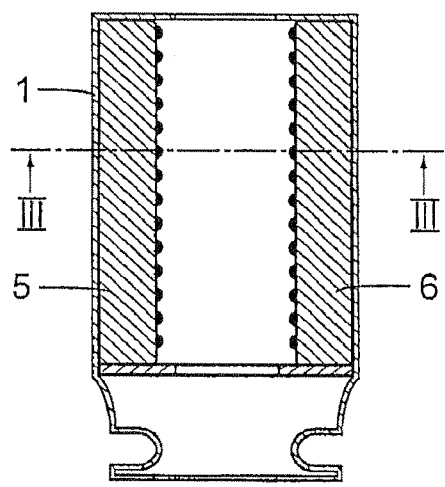
FIG. 2 is a longitudinal cross-section of an embodiment of the apparatus of FIG. 1 including a constriction device and an electric stimulation device.
Figure 4:
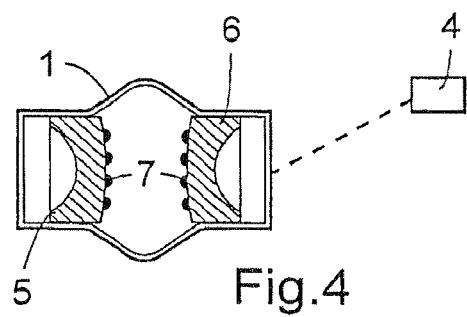
FIG. 4 is the same cross-section shown in FIG. 3 but with the apparatus in a different state of operation.

FIGS. 2-4 show basic components of an embodiment of the apparatus according to FIGS. 1A-1C for controlling the movement of bile and/or gallstones in the biliary duct. The apparatus includes a tubular housing 1 with open ends, a constriction device 2 arranged in the housing 1, a stimulation device 3 integrated in the constriction device 2, and a control device 4 (indicated in FIG. 4) for controlling the constriction and stimulation devices 2 and 3. The constriction device 2 has two elongate clamping elements 5, 6, which are radially movable in the tubular housing 1 towards and away from each other between retracted positions, see FIG. 3, and clamping positions, see FIG. 4. The stimulation device 3 includes a multiplicity of electrical elements 7 positioned on the clamping elements 5, 6, so that the electrical elements 7 on one of the clamping elements 5, 6 face the electrical elements 7 on the other clamping element. Thus, in this embodiment the constriction and stimulation devices form a constriction/stimulation unit, in which the constriction and stimulation devices are integrated in a single piece.

The constriction and stimulation devices may also be separate from each other. In this case, a structure may be provided for holding the electrical elements 7 in a fixed orientation relative to one another. Alternatively, the electrical elements 7 may include electrodes that are separately attached to the wall portion of the patient's biliary duct.

Figure 5A:
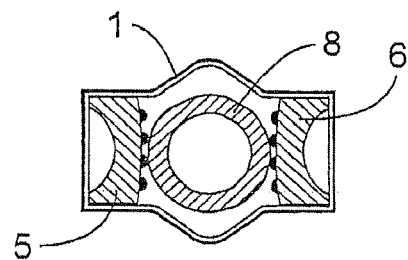
FIGS. 5A, 5B and 5C are cross-sections of the embodiment of FIG. 2 showing different states of operations with the apparatus applied on a tissue wall of a patient's biliary duct.
Figure 5B:
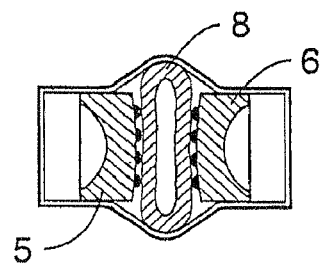
Figure 5C:
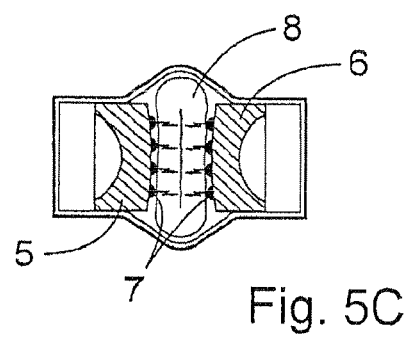

FIGS. 5A-5C illustrate in principle the function of the apparatus of FIG. 2 when the apparatus is applied on a portion 8 of a tubular tissue wall of a patient's biliary duct. Thus, FIG. 5A shows the apparatus in a non-clamping state, in which the clamping elements 5, 6 are in their retracted positions and the wall portion 8 extends through the open ends of the housing 1 without being constricted by the clamping elements 5, 6. FIG. 5B shows the apparatus in a clamping state, in which the clamping elements 5, 6 have been moved from their retracted positions to their clamping positions, in which the clamping elements 5, 6 gently constrict the wall portion 8 to a constricted state, in which the blood circulation in the constricted wall portion 8 is substantially unrestricted and the movement of bile and/or gallstones in the biliary duct of the wall portion 8 is restricted. FIG. 5C shows the apparatus in a stimulation state, in which the clamping elements 5, 6 constrict the wall portion 8 and the electrical elements 7 of the stimulation device 3 electrically stimulate different areas of the wall portion 8, so that the wall portion 8 contracts (thickens) and closes the lumen.

When the apparatus is in its stimulation state, it is important to stimulate the different areas of the wall portion 8 in a manner so that they essentially maintains their natural physical properties over time to prevent the areas from being injured. Consequently, the control device 4 controls the stimulation device 3 to intermittently stimulate each area of the wall portion 8 during successive time periods, wherein each time period is short enough to maintain over time satisfactory blood circulation in the area. Furthermore, the control device 4 controls the stimulation of the areas of the wall portion 8, so that each area that currently is not stimulated restores substantially normal blood circulation before it is stimulated again. To maintain over time the effect of stimulation, i.e., to keep the biliary duct closed by maintaining the wall portion 8 contracted, the control device 4 controls the stimulation device 3 to stimulate one or more of the areas at a time and to shift the stimulation from one area to another over time. The control device 4 may control the stimulation device 3 to cyclically propagate the stimulation of the areas along the tubular wall portion 8, for example in accordance with a determined stimulation pattern. To achieve the desired reaction of the tissue wall during the stimulation thereof, the control device may control the stimulation device to, preferably cyclically, vary the intensity of the stimulation of the wall portion 8.

In the embodiment of FIGS. 2-4, the electrical elements 7 form a series of fourteen groups of electrical elements 7 extending longitudinally along each elongate clamping element 5 and 6, respectively, see FIG. 2. The electrical elements 7 of each group of electrical elements 7 form a first path of four electrical elements 7 positioned in a row on clamping element 5 and extending tranverse thereto and a second path of four electrical elements 7 positioned in a row on clamping element 6 and extending tranverse thereto. Thus, the two paths of electrical elements 7 extend on mutual sides of the patient's biliary duct. The control device 4 controls the stimulation device 3 to successively energize the groups of electrical elements 7 in the series of groups in a direction opposite to or, alternatively, in the same direction as that of the flow in the patient's biliary duct. Of course, the number of electrical elements 7 of each path of electrical elements 7 can be greater or smaller than four, and several parallel rows electrical elements 7 can form each path of electrical elements 7.

Figure 6A:
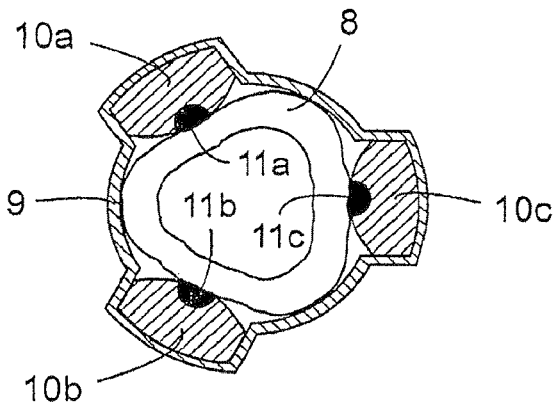
FIGS. 6A, 6B and 6C are cross-sections of a modification of the embodiment of FIG. 2 showing different states of operations with the apparatus applied on a tissue wall of a patient's biliary duct.
Figure 6B:
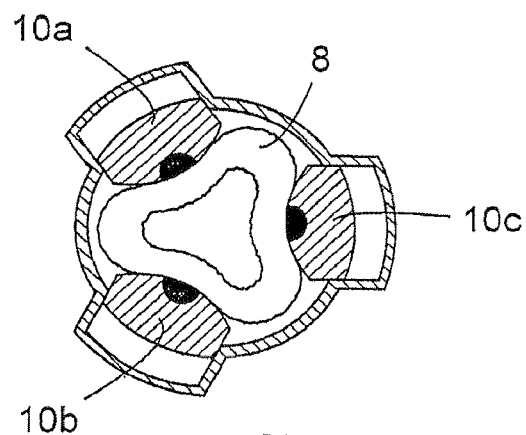
Figure 6C:
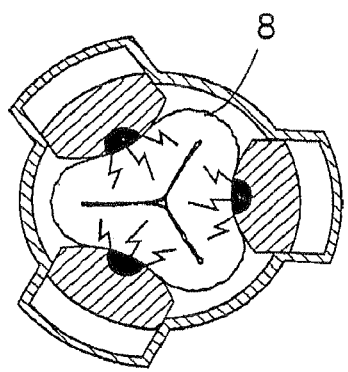

FIGS. 6A-6C show another embodiment of an apparatus used for practicing the method of the invention including a tubular housing 9 and three elongate clamping elements 10a, 10b, 10c, which are radially movable in the tubular housing 9 towards and away from a central axis thereof between retracted positions, see FIG. 6A, and clamping positions, see FIG. 6B. The three clamping elements 10a-10c are symmetrically disposed around the central axis of the housing 9. The stimulation device of this embodiment includes electrical elements 11a, 11b, 11c that form a series of groups of elements extending longitudinally along the elongate clamping elements 10a-10c, wherein the electrical elements 11a-11c of each group of electrical elements form a path of three electrical elements 11a, 11b and 11c extending circumferentially around the central axis of the housing 9. The three electrical elements 11a-11c of each group are positioned on the three clamping elements 10a-10c, respectively. Thus, the path of three electrical elements 11a-11c extends around the patient's biliary duct. Of course, the number of electrical elements 11a-11c of each path of electrical elements can be greater than three, and several parallel rows electrical elements 11a-11c can form each path of electrical elements.

Figures 7A, 7B:
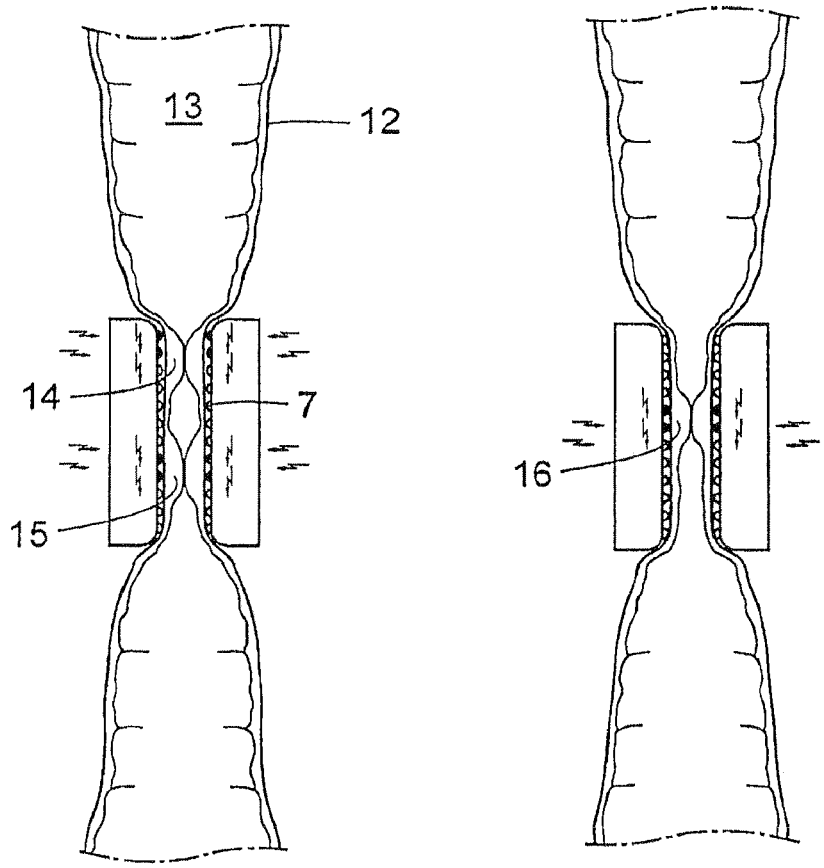
FIGS. 7A and 7B show different steps of an electric stimulation mode performed by the apparatus of FIG. 2 while the apparatus is constricting a tissue wall of a patient's biliary duct.

FIGS. 7A and 7B show different steps of an electric stimulation mode performed by the apparatus of FIG. 2 while the clamping elements 5, 6 of the apparatus are constricting a portion of a tubular tissue wall of a patient's biliary duct 12 to restrict the movement of bile and/or gallstones in the lumen 13 of the biliary duct 12. For the sake of clarity only the clamping elements 5, 6 of the constriction device 2 are shown in FIGS. 7A, 7B. Thus, FIG. 7A illustrates how energized electrical elements 7 of groups of electrical elements electrically stimulate a first portion 14 and a second portion 15 of the tubular wall to contract and close the biliary duct 13. FIG. 7B illustrates how energized electrical elements 7 of other groups of electrical elements electrically stimulate a third portion 16 of the tubular wall different from the first and second portions to contract and close the biliary duct 13, while the electrical stimulation of the first and second portions 14, 15 of the tubular wall has been ceased, so that substantially normal blood circulation in the first and second portions is restored. In this manner, the electric stimulation of the constricted tubular wall is shifted over time from one portion of the tubular wall to another to insure recurrent restoration of blood circulation in the constricted tubular wall.

The control device 4 controls the stimulation device 3 to energize the electrical elements 7 with electric biphasic pulses, i.e., combined positive and negative pulses. The desired stimulation effect is achieved by varying different pulse parameters. Thus, the control device 4 controls the stimulation device 3 to vary the pulse amplitude (voltage), the off time period between successive pulses, the pulse duration and the pulse repetition frequency. The pulse current should be between 1 to 30 mA. For neural stimulation, a pulse current of about 5 mA and a pulse duration of about 300 μs are suitable, whereas a pulse current of about 20 mA and a pulse duration of about 30 μs are suitable for muscular stimulation. The pulse repetition frequency suitably is about 10 Hz. For example, as illustrated in the Pulse/time diagram P/t of FIG. 8A, a pulse combination including a negative pulse PS of short duration and high amplitude (voltage), and a positive pulse PL of long duration and low amplitude following the negative pulse may be cyclically repeated to form a pulse train of such pulse combinations. The energy content of the negative pulse PS should be substantially equal to the energy content of the positive pulse PL.

Figure 8A:
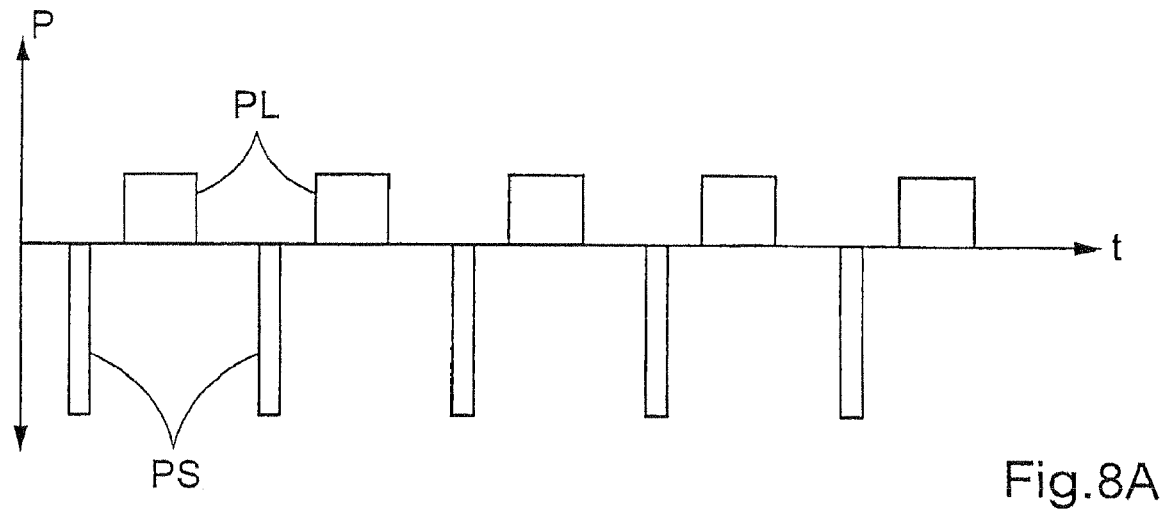
FIG. 8A is a pulse/time diagram showing electric stimulation pulses generated by the apparatus used for practicing the method of the invention, wherein the electric pulses are for stimulating a tissue wall of a patient's biliary duct.
Figure 8B:
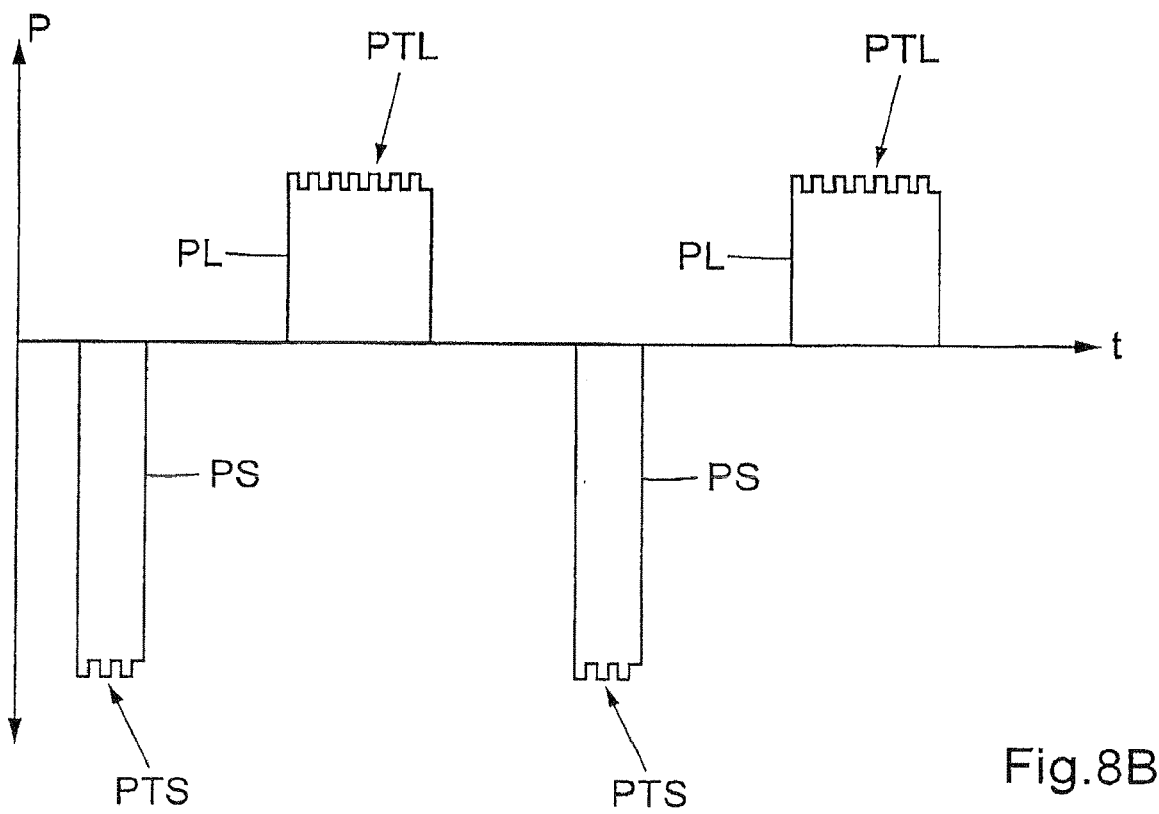
FIG. 8B is pulse/time diagram showing a modification of the electric stimulation shown in FIG. 8A, in which pulses of mixed frequencies and/or amplitudes are employed.

FIG. 8B is a pulse/time diagram showing a modification of the electric stimulation shown in FIG. 8A. Thus, the pulse combination of FIG. 8A is mixed with a pulse train combination having a first relatively long pulse train PTL of high frequency/low amplitude pulses, appearing simultaneously with the positive pulse PL of the pulse combination of FIG. 8A, and a second relatively short pulse train PTS of high frequency/low amplitude appearing simultaneously with the negative pulse PS of the pulse combination shown in FIG. 8A. As a result, the high frequency/low amplitudes pulse trains PTL and PTS are superimposed on the positive and negative pulses PL and PS of FIG. 8A, as illustrated in FIG. 8B. The pulse configuration of FIG. 8B, and variations thereof, is beneficial to use in connection with the stimulation of particular human organs, in order to achieve the desired stimulation effect.

Figure 9A:
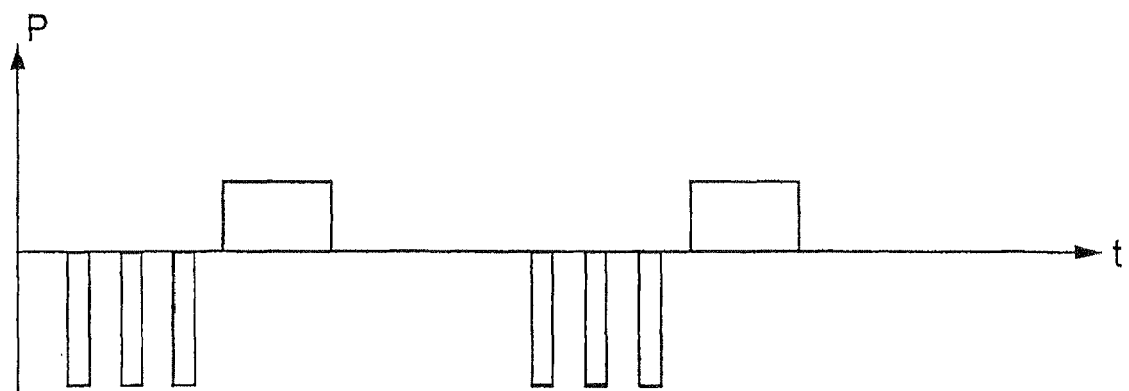
FIGS. 9A and 9B show two pulse/time diagrams, respectively, representing electric stimulation of two different areas of the tissue wall with pulses forming pulse trains.

Preferably, the electric pulses form pulse trains, as illustrated in the Pulse/time diagrams P/t of FIGS. 9A, 9B, 9C and 9D. The Pulse/time diagram P/t of FIG. 9A represents an individual area of the wall portion of the patient's biliary duct which is stimulated with a pulse train 18A. The pulse train 18A includes three initial negative pulses, each of which is of short duration and high amplitude (voltage), and one positive pulse of long duration and low amplitude following the negative pulses. After a delay to enable the area of the biliary duct to restore substantially normal blood circulation the pulse train 18A is repeated.

Figure 9B:
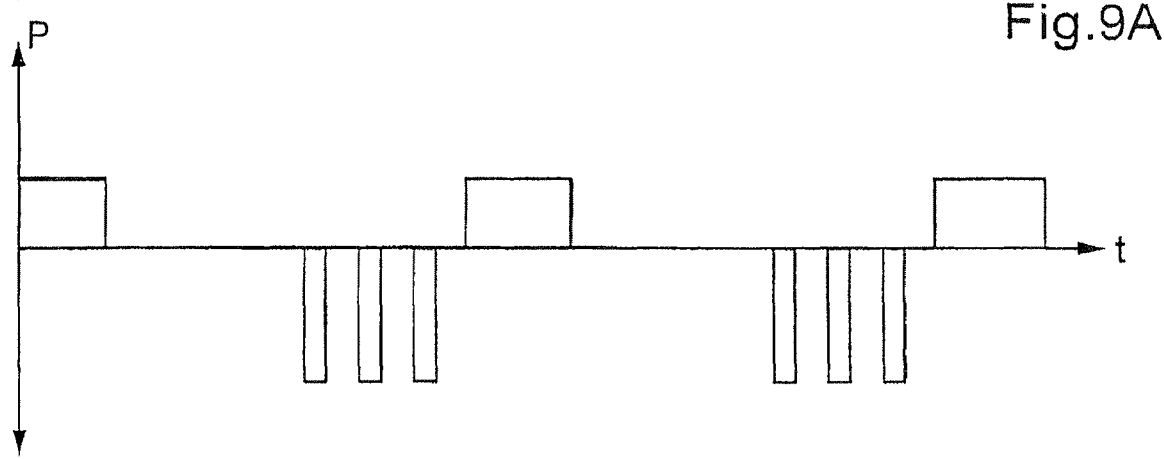

The Pulse/time diagram P/t of FIG. 9B represents another individual area of the wall portion, which is stimulated with a pulse train 18B having the same configuration as the pulse train 18A. The pulse trains 18A and 18B are shifted relative to each other, so that they partially overlap one another to ensure that the constricted wall portion always is stimulated to contract as desired.

Figure 10A:
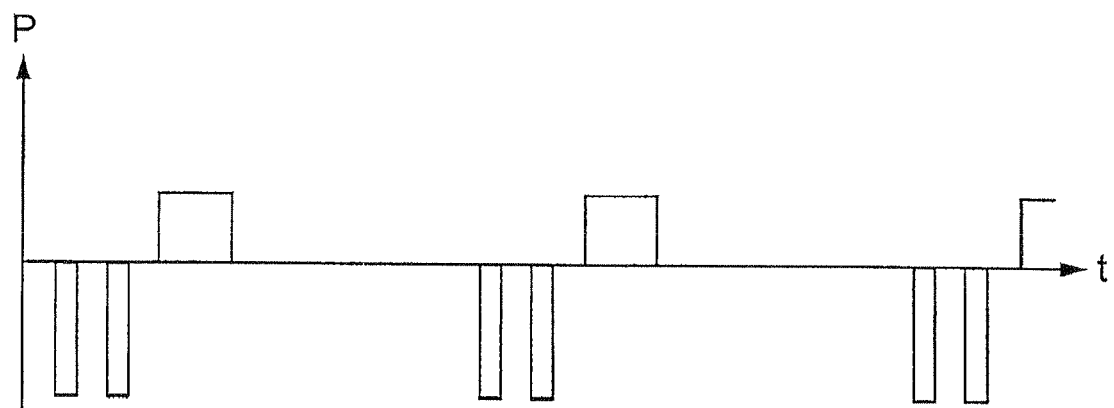
FIGS. 10A and 10B show the pulse/time diagrams of FIGS. 9A and 9B with modified pulse trains.
Figure 10B:
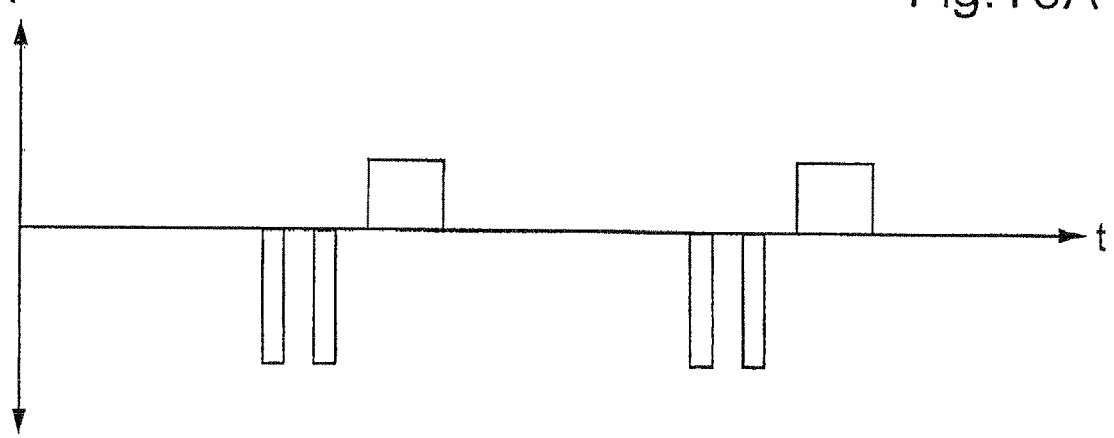

The pulse/time diagrams P/t of FIGS. 10A and 10B represent two different areas of the wall portion, which are stimulated with cyclically repeated pulse trains 18C and 18D, respectively, having the same configuration. Each pulse train 18C, 18D includes two initial negative pulses, each of which is of short duration and high amplitude (voltage), and one positive pulse of long duration and low amplitude following the two negative pulses. In this case, the pulse trains 18C and 18D are shifted relative to each other, so that they do not overlap each other. Thus, the off time period between adjacent pulse trains 18C is longer than the duration of pulse train 18D and the off time period between adjacent pulse trains 18D is longer than the duration of pulse train 18C.

The pulse trains 18A, 18B, 18C and 18D can be configured in many different ways. Thus, the control device 4 can control the stimulation device 2 to vary the length of each pulse train, the repetition frequency of the pulse trains, the number of pulses of each pulse train, and/or the off time periods between the pulse trains. Typically, the control device 4 controls each off time period between the pulse trains to last long enough to restore substantially normal blood circulation in the area that just has been stimulated before that area again is stimulated with electric pulses.

Figure 11A:
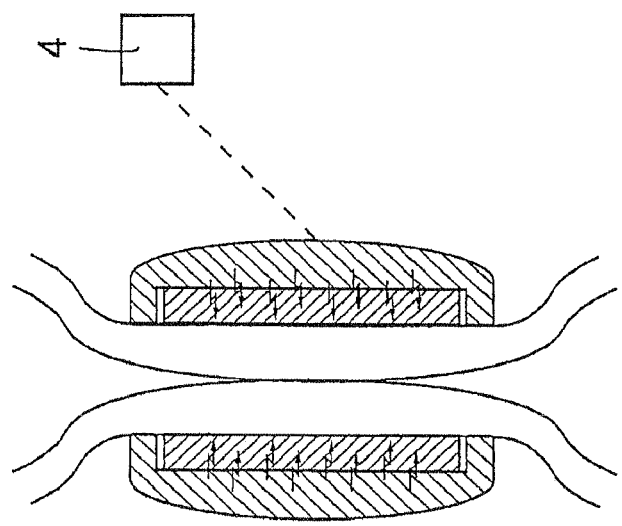
FIG. 11A is a longitudinal cross-section of an embodiment of an apparatus used for practicing the method of the invention, where the apparatus includes a thermal stimulation device and the apparatus is constricting a tissue wall of a patient's biliary duct.
Figure 11B:
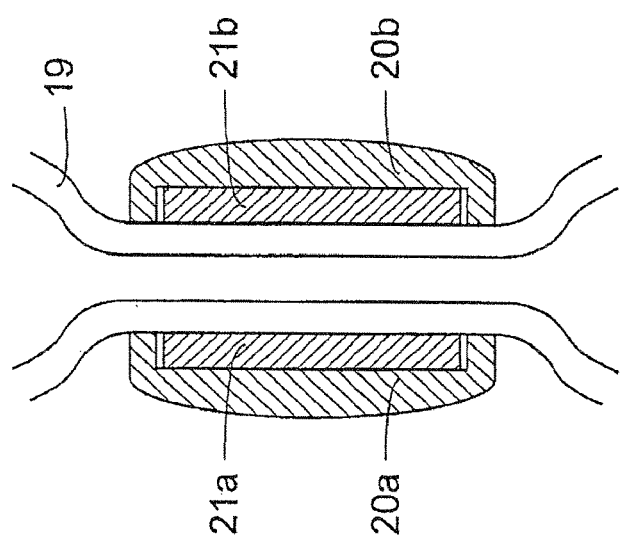
FIG. 11B is the same embodiment of FIG. 11A with the thermal stimulation device activated.

FIGS. 11A and 11B show another embodiment of an apparatus used for practicing the method of the invention that controls flow in a biliary duct 19. The apparatus of FIGS. 11A and 11B includes a constriction device with two clamping elements 20a and 20b, a stimulation device in the form of two thermal stimulation elements 21a and 21b integrated in the clamping elements 20a, 20b, respectively, and a control device 4 for controlling the clamping elements 20a, 20b and stimulation elements 21a, 21b. The clamping elements 20a and 20b are movable towards and away from each other in the same manner as described above in connection with the embodiment according to FIGS. 5A-5C. The thermal stimulation elements 21a and 21b, which may include Pertier elements, are positioned on the clamping elements 20a, 20b, so that the thermal elements 21a are facing the thermal elements 21b. FIG. 11A shows how the clamping elements 20a, 20b constrict the biliary duct 19, so that the blood movement of bile and/or gallstones is restricted. FIG. 11B shows how the control device 4 controls the thermal stimulation elements 21a, 21b to cool the wall of the biliary duct 19, so that the wall contracts and closes the biliary duct 19. To release the biliary duct 19, the control device 4 controls the thermal stimulation elements 21a, 21b to heat the wall of the biliary duct 19, so that the wall expands.

Figure 12A:
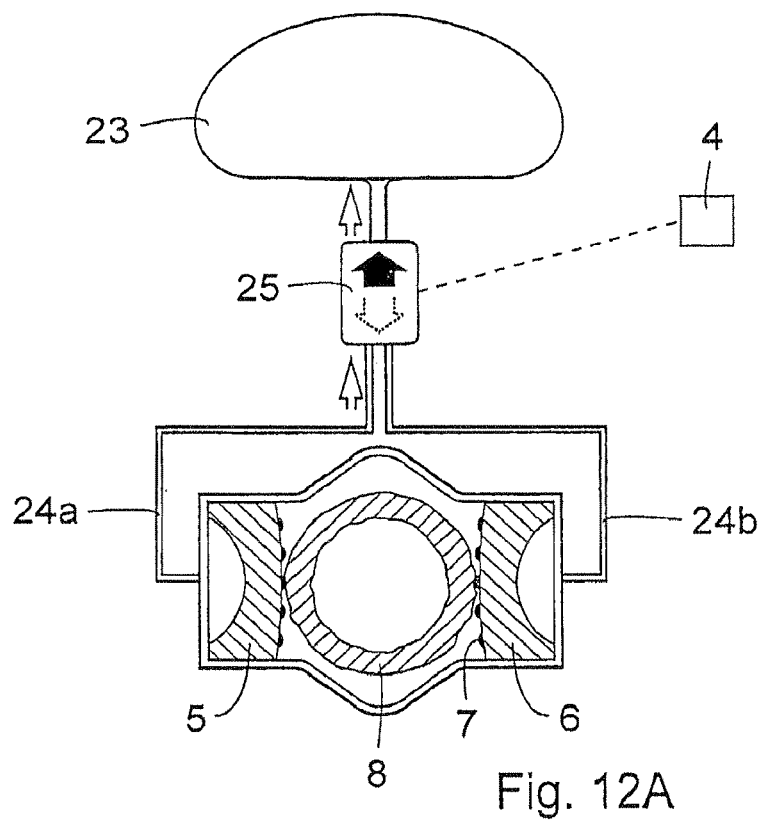
FIG. 12A is a schematic view of hydraulic operation means suited for operating the constriction device of the embodiments of FIGS. 2-11.
Figure 12B:
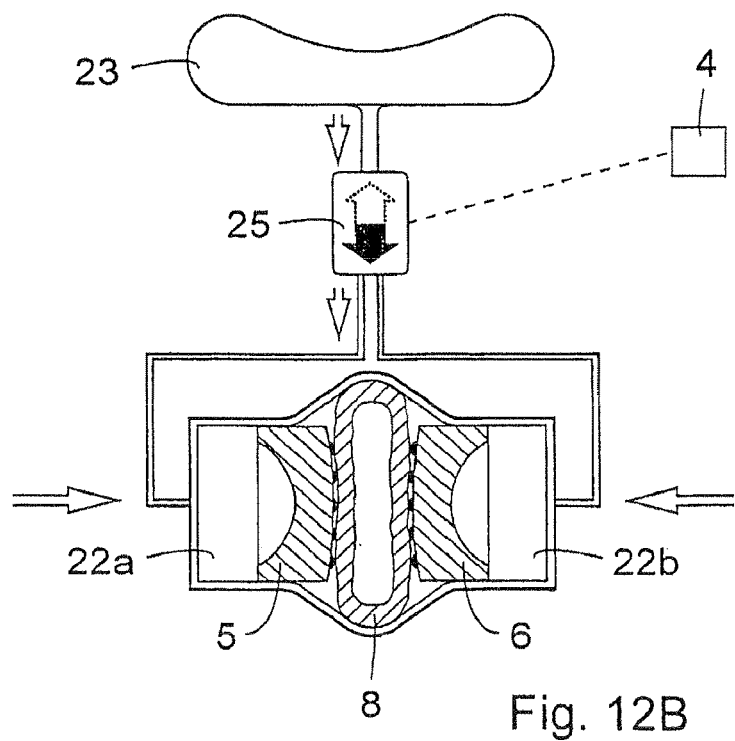
FIG. 12B shows the embodiment of FIG. 12A with the constriction device constricting a tissue wall of a patient's biliary duct.

FIGS. 12A and 12B show hydraulic operation means suited for operating the constriction device of the embodiments described above. Specifically, FIGS. 12A and 12B show the apparatus of FIG. 2 provided with such means for hydraulic operation of the constriction device 2. (The stimulation device is not shown.) Thus, the housing 1 forms two hydraulic chambers 22a and 22b, in which the two clamping elements 5,6 are slidable back and forth relative to the tubular tissue wall portion 8 of a patient's biliary duct. The hydraulic operation means include an expandable reservoir 23, such as an elastic balloon, containing hydraulic fluid, conduits 24a and 24b between the reservoir 23 and the hydraulic chambers 22a, 22b, and a two-way pump 25 for pumping the hydraulic fluid in the conduits 24a, 24b. The control device 4 controls the pump 25 to pump hydraulic fluid from the reservoir 23 to the chambers 22a, 22b to move the clamping elements 5, 6 against the wall portion 8, whereby the tubular wall portion 8 is constricted, see FIG. 12B, and to pump hydraulic fluid from the chambers 22a, 22b to the reservoir 23 to move the clamping elements 5, 6 away from the wall portion 8, whereby the tubular wall 8 is released, see FIG. 12A.

Alternatively, the embodiment of FIGS. 12A and 12B may be manually operated by applying suitable manually operable hydraulic means for distributing the hydraulic fluid between the expandable reservoir 23 and the hydraulic chambers 22a, 22b. In this case the pump 25 is omitted.

Figure 13A:
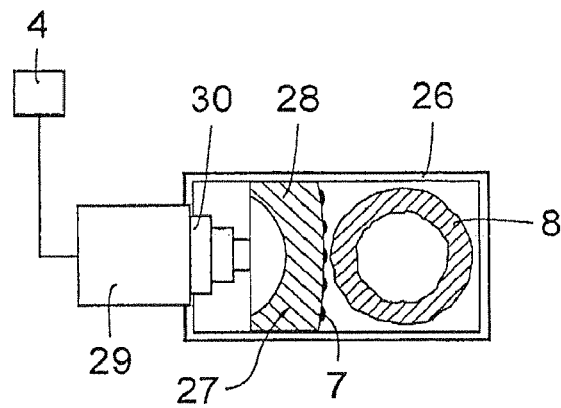
FIG. 13A is a schematic view of mechanical operation means suited for operating the constriction device of the embodiments of FIGS. 2-11.
Figure 13B:
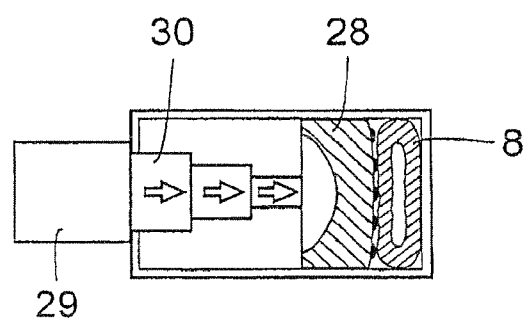
FIG. 13B shows the embodiment of FIG. 13A with the constriction device constricting a tissue wall of a patient's biliary duct.

FIGS. 13A and 13B schematically show another embodiment of an apparatus used for practicing the method of the invention. The apparatus of FIGS. 13A and 13B comprises an open ended tubular housing 26 applied on the tubular tissue wall portion 8 of a patient's biliary duct, a constriction device 27 arranged in the housing 26 and a control device 4 for controlling the constriction device 27. A stimulation device (not shown) as described above is also provided in the housing 26. The constriction device 27 includes a clamping element 28, which is radially movable in the tubular housing 26 towards and away from the tubular wall portion 8 between a retracted position, see FIG. 13A, and a clamping position, see FIG. 13B, in which the clamping element 28 gently constricts the tubular wall portion 8. Mechanical operation means for mechanically operating the clamping element 28 includes an electric motor 29 attached to the housing 26 and a telescopic device 30, which is driven by the motor 29 and operatively connected to the clamping element 28. The control device 4 controls the electric motor 29 to expand the telescopic device 30 to move the clamping element 28 against the wall portion 8, whereby the tubular wall portion 8 is constricted, see FIG. 13B, and controls the motor 29 to retract the telescopic device 30 to move the clamping element 28 away from the wall portion 8, whereby the wall portion 8 is released, see FIG. 13A.

Figure 13C:
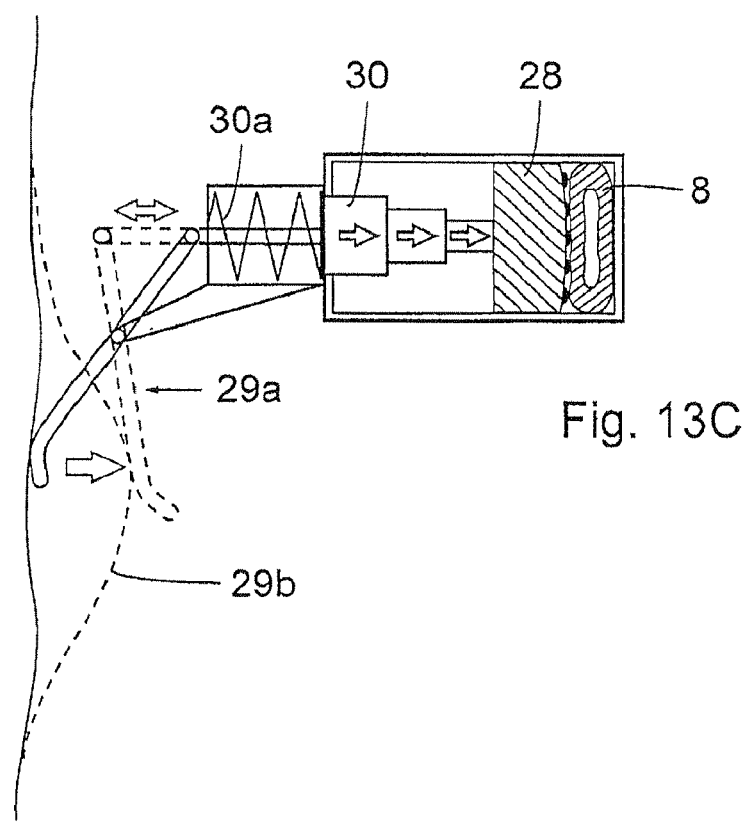
FIG. 13C shows a modification of the embodiment of FIG. 13B.

Alternatively, the motor 29 may be omitted and the telescopic device 30 be modified for manual operation, as shown in FIG. 13C. Thus, a spring 30a may be provided acting to keep the telescopic device 30 expanded to force the clamping element 28 against the wall portion 8. The mechanical operation means may include a subcutaneously implanted lever mechanism 29a that is operatively connected to the telescopic device 30. The patient may push the lever mechanism 29a through the skin to pull the telescopic device 30 against the action of the spring 30a to the retracted position of the telescopic device 30, as indicated in phantom lines. When the patient releases the lever mechanism 29a, the spring 30a expands the telescopic device 30, whereby clamping element 28 is forced against the wall portion 8.

The mechanical operation means as described above in connection with FIGS. 13A, 13B and 13C may also be implemented in the embodiments according to FIGS. 1-11.

FIG. 14 illustrates the embodiment of FIG. 2 applied on the common bile duct 31 of a gallstone patient. The clamping elements 5, 6 of the constriction device 2 constrict the common bile duct 31 and the stimulation device 3 is energized to close the common bile duct. (For the sake of clarity, the housing is not shown and the clamping elements 5, 6 are exaggerated.) In this embodiment, a control device includes an external control unit in the form of a hand-held wireless remote control 32. The remote control 32 is operable by the patient to control the internal control unit 33 to switch on and off the constriction device and/or the stimulation device. Alternatively, however, the remote control 32 may be replaced by a subcutaneously implanted push button that is manually switched by the patient between "on" and "off". Such a manually operable push button may also be provided in combination with the remote control 32 as an emergency button to allow the patient to stop the operation of the apparatus in case of emergency or malfunction.

The internal control unit 33 controls an implanted operation device 34 to move the clamping elements 5, 6. An implanted source of energy 35, such as a rechargeable battery, powers the operation device 34. The internal control unit 33, which may be implanted subcutaneously or in the abdomen, also works as en energy receiver, i.e., for transforming wireless energy into electric energy and charging the implanted source of energy 35 (rechargeable battery) with the electric energy.

An implanted sensor 36 senses a physical parameter of the patient, such as the pressure in the common bile duct, or a parameter that relates to the pressure in the intestines, wherein the internal control unit 33 controls the constriction device 2 and/or the stimulation device 3 in response to signals from the sensor 36. In this embodiment the sensor 36 is a pressure sensor, wherein the internal control unit 33 controls the constriction device and/or stimulation device to change the constriction of the patient's intestines 31 in response to the pressure sensor 36 sensing a predetermined value of measured pressure. For example, the control unit 33 may control the constriction device and/or stimulation device to increase the constriction of the patient's common bile duct 31 in response to the pressure sensor sensing an increased pressure. Alternatively or in combination, the remote control 32 controls the constriction device and/or stimulation device in response to signals from the sensor 36. The remote control 32 may be equipped with means for producing an indication, such as a sound signal or displayed information, in response to signals from the sensor 36, in the same manner as the internal control unit 33.

The remote control 32 may be equipped with means for producing an indication, such as a sound signal or displayed information, in response to signals from the sensor 36.

Of course, the constriction device 2 shown in FIG. 14 may be replaced by any one of the devices described in the various embodiments of the present invention, where applicable.

Figure 15:
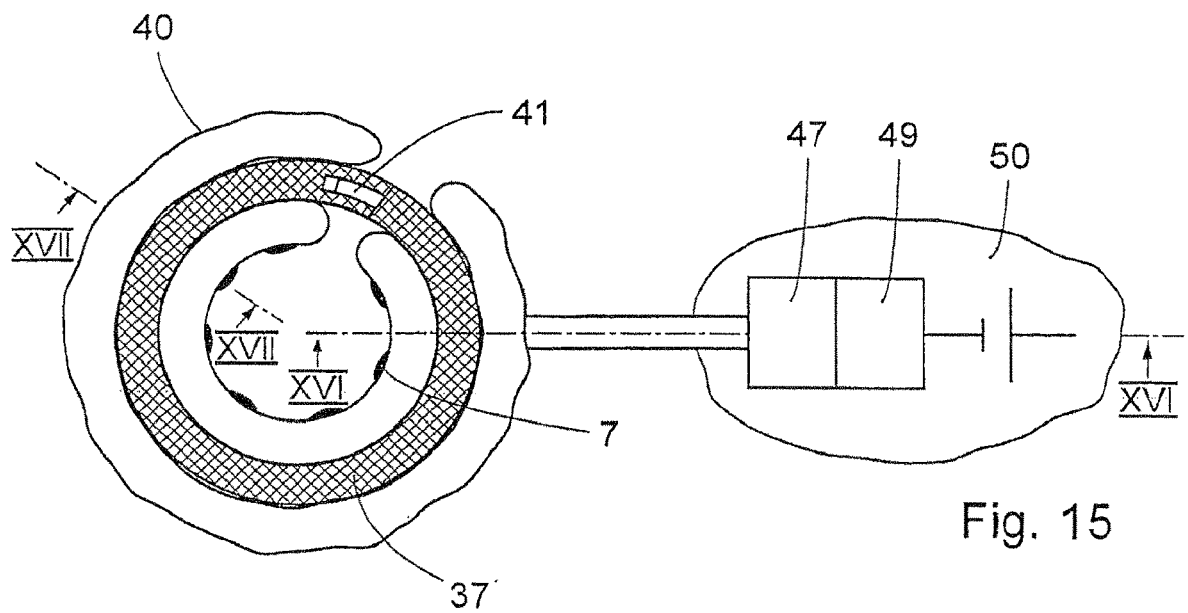
FIG. 15 is a schematic sectional view of a mechanically operable non-inflatable constriction device used for practicing the method of the invention.
Figure 16:
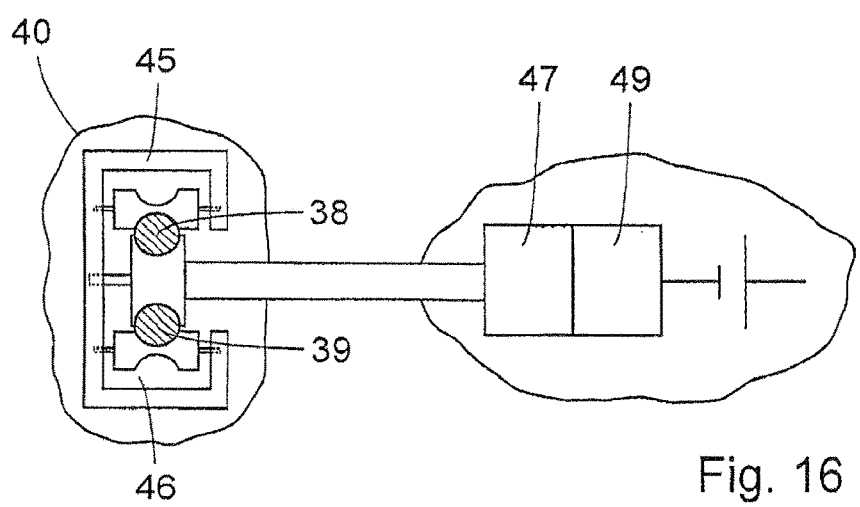
FIGS. 16 and 17 are cross-sectional views taken along the lines XVI-XVI and XVII-XVII, respectively, of FIG. 15.
Figure 17:
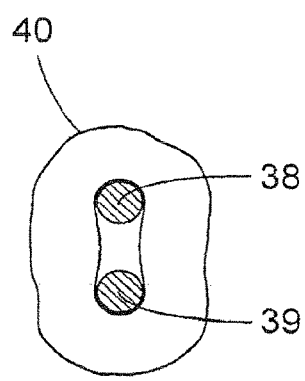

FIGS. 15-17 show another embodiment of an apparatus used for practicing the method of the invention. The apparatus of FIGS. 15-17 includes a mechanically operable constriction device having an elongated constriction member in the form of a circular resilient core 37 with two overlapping end portions 38, 39. The core 37 defines a substantially circular restriction opening and is enclosed in an elastic soft hose 40 except at a releasable and lockable joint 41 of the core 37, which when released enables application of the core 37 with its hose 40 around a portion of a tubular tissue wall of a patient. The materials of all of these elements are biocompatible so that the patient' body will not reject them. An operation device 42 for mechanically operating the longitudinal extension of the core 37 to change the size of the restriction opening comprises a drive wheel 43 in frictional engagement with the overlapping end portions 38, 39 of the core 37. The drive wheel 43 is journalled on a holder 44 placed in the hose 40 and provided with two counter pressure rollers 45, 46 pressing the respective end portions 38, 39 of the core 37 against the drive wheel 43 to increase the frictional engagement there between. An electric motor 47 of the operation device is connected to the drive wheel 43 via a long flexible drive shaft 48 and is molded together with a remote controlled power supply unit 49 in a body 50 of silicone rubber. The length of the flexible drive shaft 48 is selected so that the body 50 can be placed in a desired position in the patient's body, suitably in the abdomen.

The power supply unit 49 can be controlled to power the electric motor 47 to turn the drive wheel 43 in one direction to reduce the diameter of the core 37, so that the wall portion is constricted, or to turn the drive wheel 43 in the opposite direction to increase the diameter of the core 37, so that the wall portion is released.

In accordance with a first alternative, a rack gear may be formed on one of the end portions 38, 39 of the core 37 and the drive wheel 43 may be replaced by a drive gear wheel connected to the other end portion of the core 37 and in mesh with the rack gear.

In accordance with a second alternative, the operation device 42 may be designed as a worm-driven hose clamp, i.e., one of the end portions 38, 39 of the core 37 may be provided with threads and the other end portion of the core 37 may be provided with a worm, the threads of which interacts with the threads of said one end portion of the core 37. The threads of such a worm may also interact with threads provided on both end portions 38, 39 of the core 37. In this alternative, the electric motor 47 turns the worm in one direction to reduce the diameter of the core 37, so that the wall portion is constricted, or turn the worm in the opposite direction to increase the diameter of the core 37, so that the wall portion is released in one direction to reduce the diameter of the core 37, so that the wall portion is constricted, or turns the clamping screw in the opposite direction to increase the diameter of the core 37, so that the wall portion is released.

Figure 18:
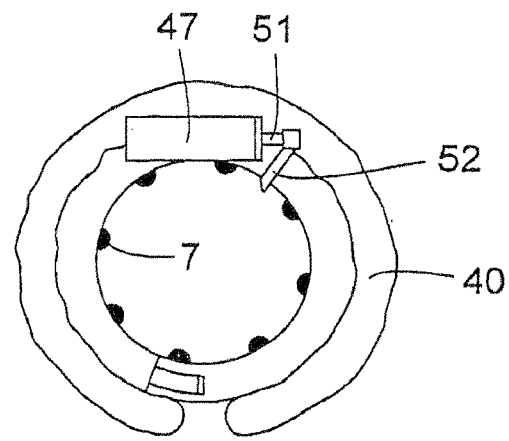
FIG. 18 schematically shows an alternative design of the embodiment of FIG. 15.

FIG. 18 shows a constriction device which is identical to the constriction device shown in FIGS. 15-17, except that the motor 47 is encapsulated in the hose 40 so that it is fixed to the core 37 and has a short drive shaft 51, and that the motor 47 is positioned relative to the core 37 such that the drive shaft 51 extends substantially tangentially to the circular core 37. There is an angular gearing 52 connecting the drive shaft 51 to the drive wheel 43.

Figure 19:
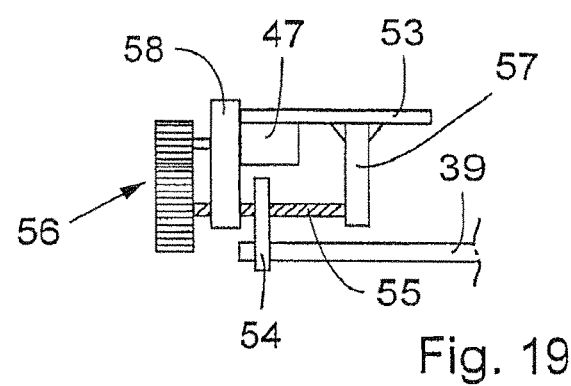
FIG. 19 schematically illustrates a motor arrangement for the embodiment according to FIG. 18.

FIG. 19 shows a suitable alternative arrangement for the motor 47 in the embodiment of FIG. 17, comprising a first clamping member 53 secured to one end portion of the core 37 and a second clamping member 54 secured to the other end portion 39 of the core 37. The motor 47 is secured to the first clamping member 53 and is operatively connected to a worm 55 via a gear transmission 56. The worm 55 is journalled at its opposite ends on holders 57 and 58, which are rigidly secured to the clamping member 53 and the motor 47, respectively. The second clamping member 54 has a pinion in mesh with the worm 55. When the motor 47 is powered the worm 55 rotates and will thereby pull the end portion 39 of the core 37 in one or the opposite longitudinal direction, so that the diameter of the substantially circular core 37 is either increased or decreased. The motor 47, worm gear 55, gear transmission 56 and second clamping member 54 constitute a servo system of the type that transfers a weak force acting on a moving element having a long stroke into a strong force acting on another moving element having a short stroke.

Figure 20:
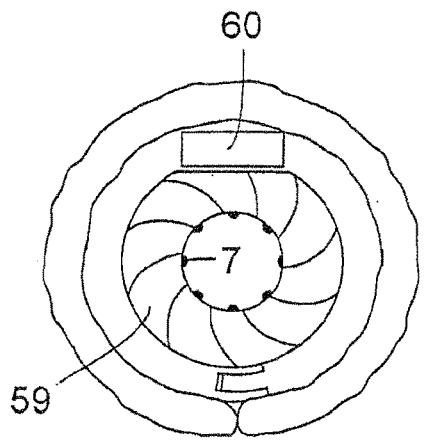
FIGS. 20 and 21 are schematic sectional views of two alternative designs of non-inflatable constriction devices used for practicing the method of the invention.

FIG. 20 shows another embodiment of an apparatus used for practicing the method of the invention. The apparatus of FIG. 20 includes a constriction device having a plurality of arcuate lamellae 59 arranged like the conventional adjustable aperture mechanism of a camera. A motor 60 operates the lamellae 59 to change the size of a restriction opening defined by the lamellae 59.

Figure 21:
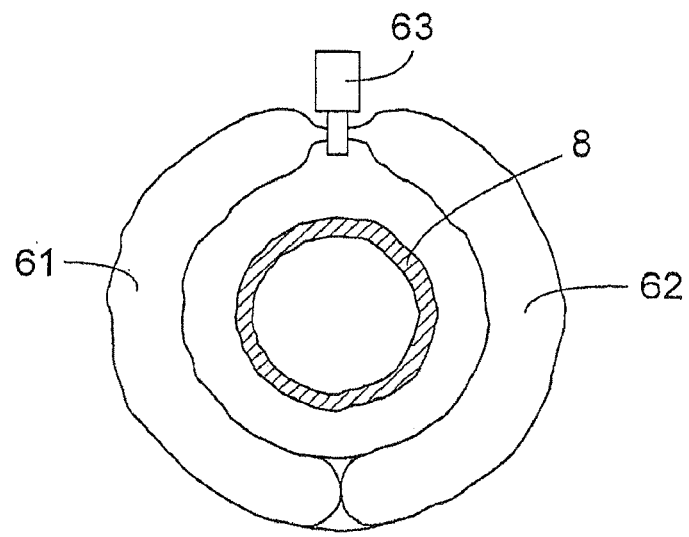
Figure 22:
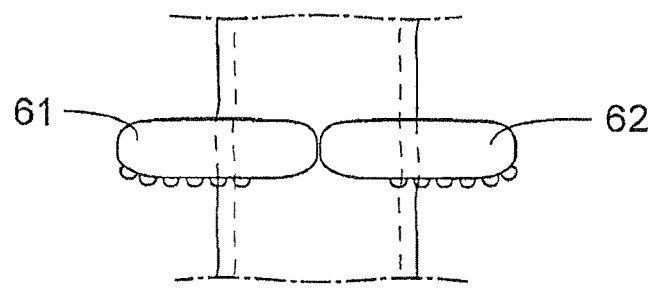
FIGS. 22 and 23 illustrate a fully open and a reduced constriction opening, respectively, of the embodiment of FIG. 21.
Figure 23:
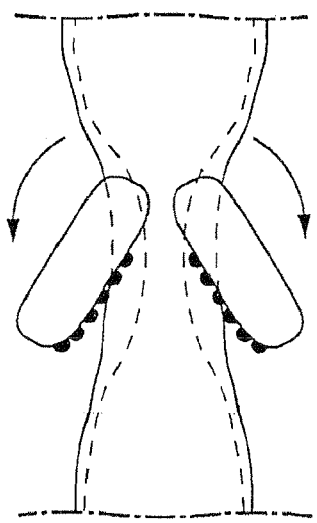
Figure 24:
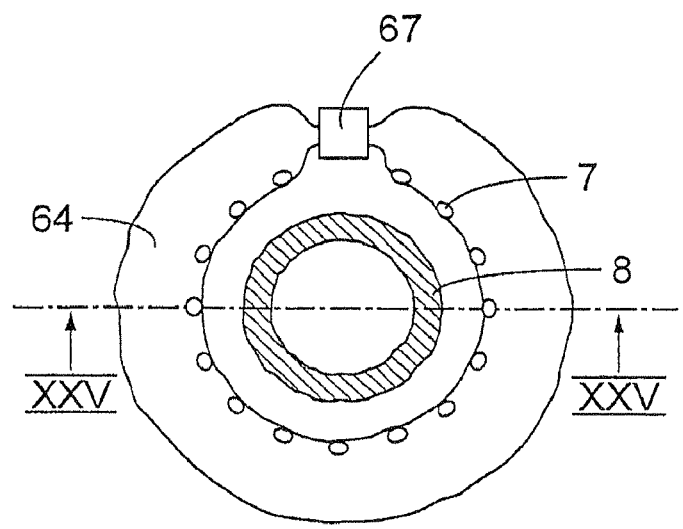
FIG. 24 is a schematic view of a further alternative design of a non-inflatable constriction device used for practicing the method of the invention.
Figure 25:
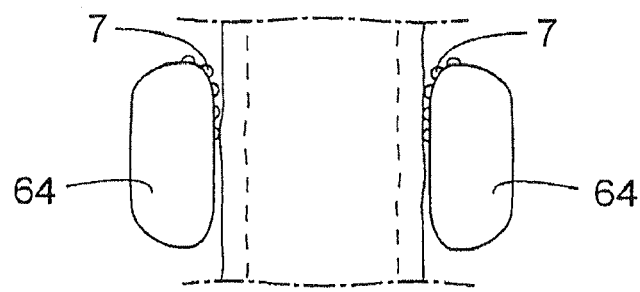
FIGS. 25 and 26 illustrate a fully open and a reduced constriction opening, respectively, of the embodiment of FIG. 24.
Figure 26:
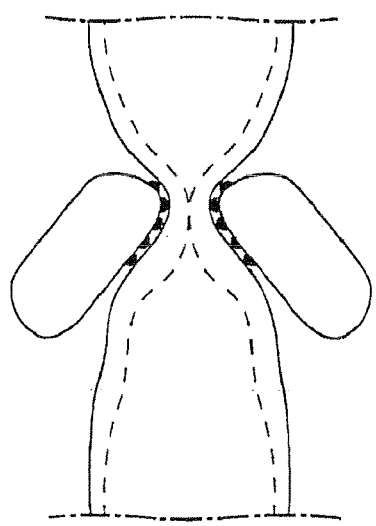

FIGS. 21-23 show another embodiment of an apparatus used for practicing the method of the invention. The apparatus of FIGS. 21-23 includes a constriction device having two semi-circular elements 61 and 62, which are hinged together. The semi-circular elements 61,62 are swingable relative to each other between a fully open state in which they substantially form a circle, illustrated in FIG. 23 and an angular state, in which the size of the restriction opening defined by the semi-circular elements 61, 62 is reduced, illustrated in FIG. 24. A motor 63 operates the semi-circular elements 61, 62 to swing them relative to each other.

FIGS. 24-28 show another embodiment of an apparatus used for practicing the method of the invention. The apparatus of FIGS. 24-28 includes a constriction device having an elastic belt 64, which forms a circle and has a substantially oval cross-section. A motor 67 operates the belt 64 to turn around the longitudinal extension thereof between a fully open state, in which the inner broader side of the belt 64 forms a substantially cylindrical surface, illustrated in FIG. 25, and a reduced open state, in which the inner broader side of the belt 64 forms a substantially conical surface, illustrated in FIG. 26.

Figure 27:
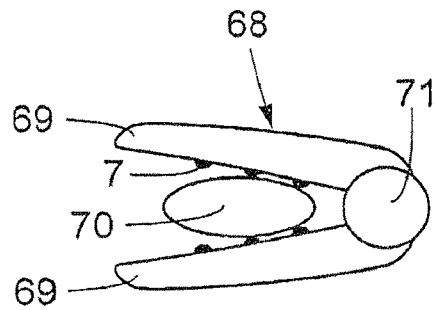
FIG. 27 is a schematic view of another alternative design of a non-inflatable constriction device used for practicing the method of the invention.

FIG. 27 shows another embodiment of an apparatus used for practicing the method of the invention. The apparatus of FIG. 27 includes a constriction device 68 having two rigid articulated clamping elements 69 positioned on opposite sides of a portion of a tubular tissue wall 70 of a patient. An operation device 71 turns the clamping elements 69 toward each other to clamp the wall portion 70 between the clamping elements 69 to thereby contract the wall portion, and turns the clamping elements 69 away from each other to release the wall portion from the clamping elements 69.

Figure 28:
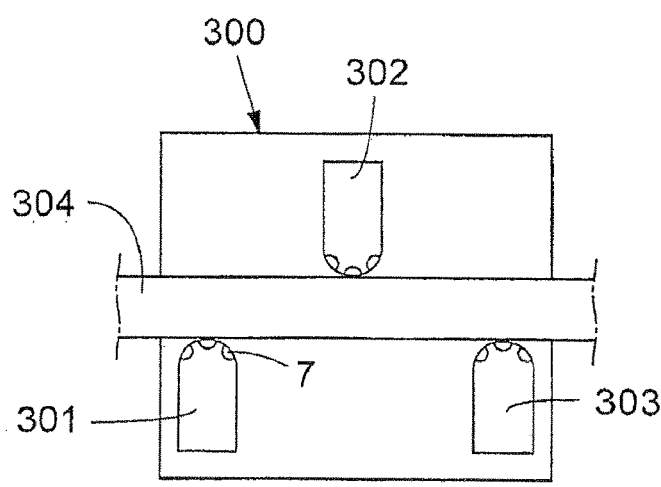
FIGS. 28 and 29 are schematic sectional views, respectively, of yet another alternative design of a non-inflatable constriction device used for practicing the method of the invention.
Figure 29:
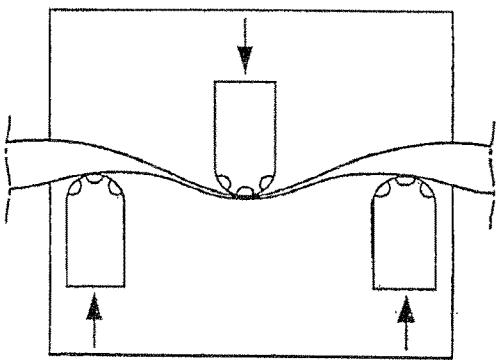

FIGS. 28 and 29 show another embodiment of an apparatus used for practicing the method of the invention. The apparatus of FIGS. 28 and 29 include a constriction device 300 having three bending members 301, 302 and 303 displaced relative to one another in a row along a portion of a tubular tissue wall 304 of a patient's biliary duct and positioned alternately on opposite sides of the tubular wall 304. (Alternatively, each member 301, 302 and 303 may take the shape of an hour-glass.) An operation device (not shown) moves the two outer members 301, 303 laterally against the tubular wall 304 in one direction and the intermediate member 302 against the tubular wall 304 in the opposite direction to bend the tubular wall 304 to thereby constrict the tubular wall portion 304, see FIG. 29. To release the wall portion 304 the operation device moves the members 301-303 away from the tubular wall portion 304 to the position shown in FIG. 28.

Figure 30A:
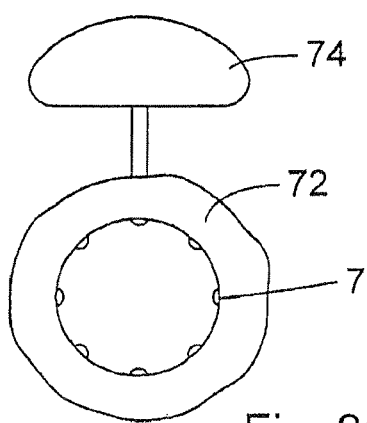
FIG. 30A is a schematic view of a hydraulically operable inflatable constriction device for used for practicing the method of the invention.
Figure 30B:
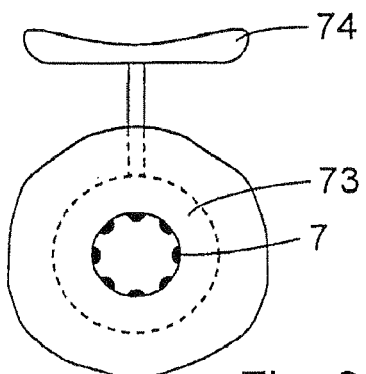
FIG. 30B is the same embodiment shown in FIG. 30A with the constriction device inflated.

FIGS. 30A and 30B show another embodiment of an apparatus used for practicing the method of the invention. The apparatus of FIGS. 30A and 30B include a hydraulically operable elongated constriction device in the form of a band 72 having an expandable/contractible cavity 73, which is in fluid communication with an adjustable reservoir 74 containing hydraulic fluid. FIG. 30A illustrates when the band is in a non-constriction state, whereas FIG. 30B illustrates when the band is in a constriction state, in which the cavity 73 is expanded by hydraulic fluid supplied by the reservoir 74.

Figure 31A:
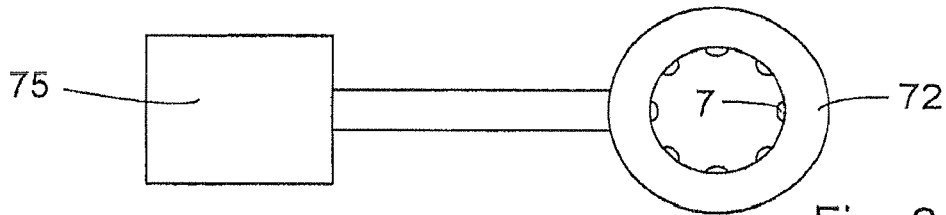
FIGS. 31A, 31B, 31C and 31D are block diagrams illustrating four different principles for hydraulic operation of the constriction device shown in FIG. 30A.
Figure 31B:
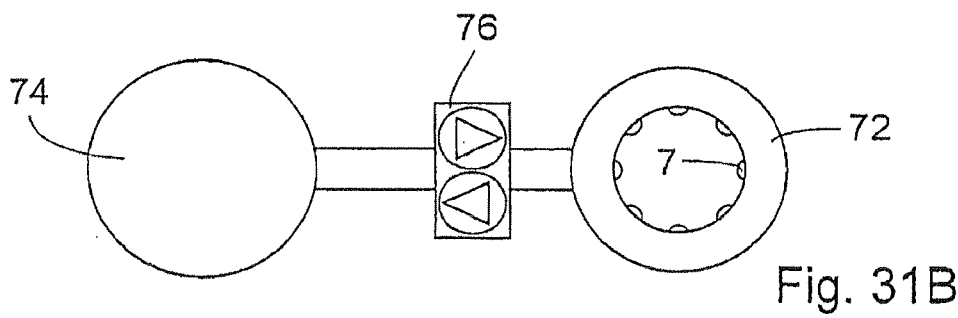
Figure 31C:
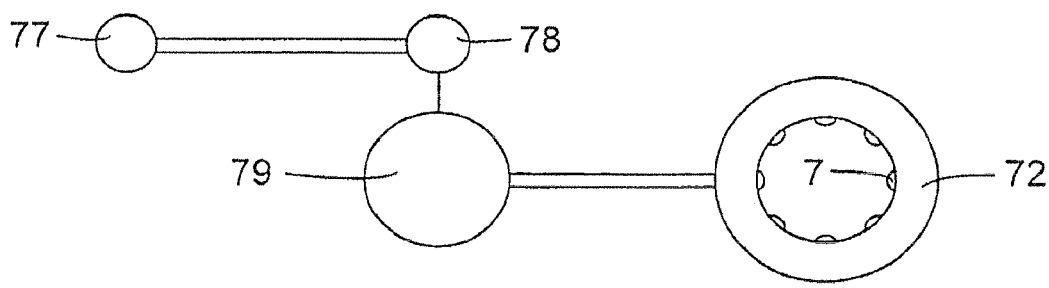
Figure 31D:
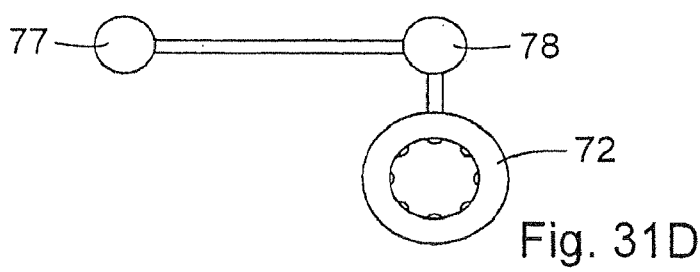

FIGS. 31A, 31B, 31C and 31D are block diagrams of three differently operated hydraulic constriction devices used for practicing the method of the invention, FIG. 31A shows the band 72 of FIG. 30A, the cavity 73 of which is in fluid communication with a reservoir 75. FIG. 31B shows the embodiment of FIG. 30A, in which the cavity 73 of the band 72 is in fluid communication with the reservoir 74 via an operation device in the form of a two-way pump 76. FIG. 31C shows an operation device in the form of a reverse servo system with a first closed system controlling a second system. The reverse servo system comprises an adjustable fluid supply reservoir 77 and an adjustable servo reservoir 78. The servo reservoir 78 controls a larger adjustable reservoir 79 which in connection with the band 72 applied around a portion of tubular tissue wall of a patient's biliary duct varies the volume of the cavity 73 of the band 72, which in turn varies the constriction of the wall portion. FIG. 31D shows an embodiment identical to the embodiment of FIG. 31C, except that the larger reservoir 79 is omitted. Instead, the servo reservoir 78 is in fluid communication with the cavity of the band 72.

In all of the above embodiments according to FIGS. 12A through 30B, stimulation devices may be provided to form constriction/stimulation units, in which the stimulation devices include a multiplicity of electrical elements 7 (indicated in FIGS. 12A-15, 18, 20-23, 26-31B) positioned on the constriction devices.

Figure 32:
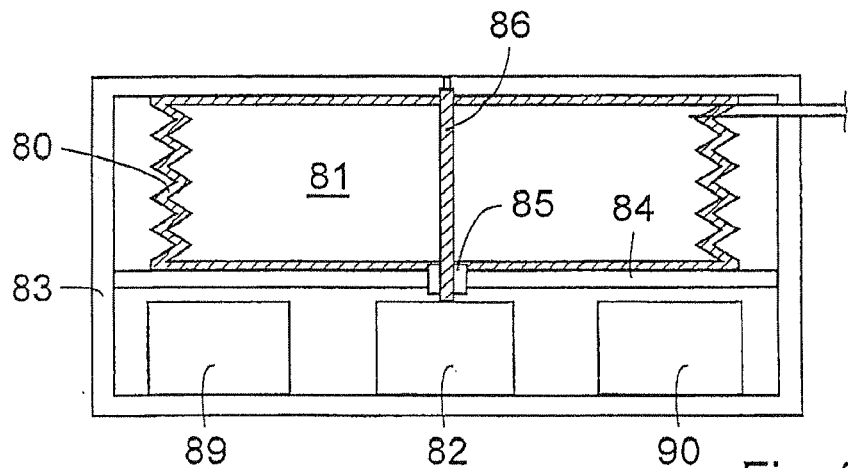
FIG. 32 is a cross-sectional view of a reservoir having a variable volume controlled by a remote control motor.

FIG. 32 is a cross-sectional view of a fluid supply device including a bellows reservoir 80 defining a chamber 81, the size of which is variable by an operation device comprising a remote controlled electric motor 82. The reservoir 80 and the motor 82 are placed in a housing 83. Moving a large wall 84 varies the chamber 81. The wall 84 is secured to a nut 85, which is threaded on a rotatable spindle 86. The spindle 86 is rotated by the motor 82. A battery 89 placed in the housing 83 powers the motor 82. A signal receiver 90 for controlling the motor 82 is also placed in the housing 83. Alternatively, the battery 89 and the signal receiver 90 may be mounted in a separate place. The motor 82 may also be powered with energy transferred from transmitted signals.

Where applicable, the fluid supply device of FIG. 32 may be used for supplying hydraulic fluid for the operation of the constriction devices described in this specification. For example, the fluid supply device of FIG. 32 may be substituted for the reservoir 74 in the embodiment according to FIG. 30A.

Figure 33A:
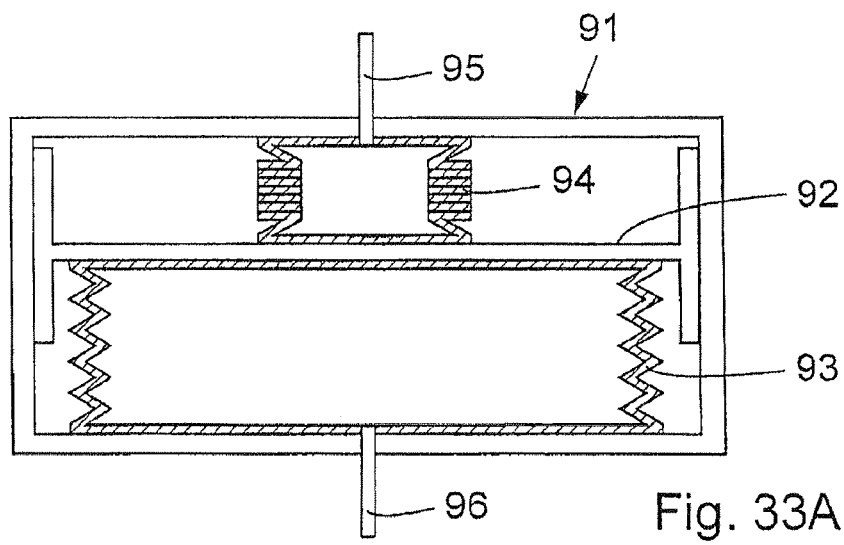
FIGS. 33A and 33B are perspective views of a reverse servo in accordance with a particular embodiment of the hydraulic operation principle shown in FIG. 31C.
Figure 33B:
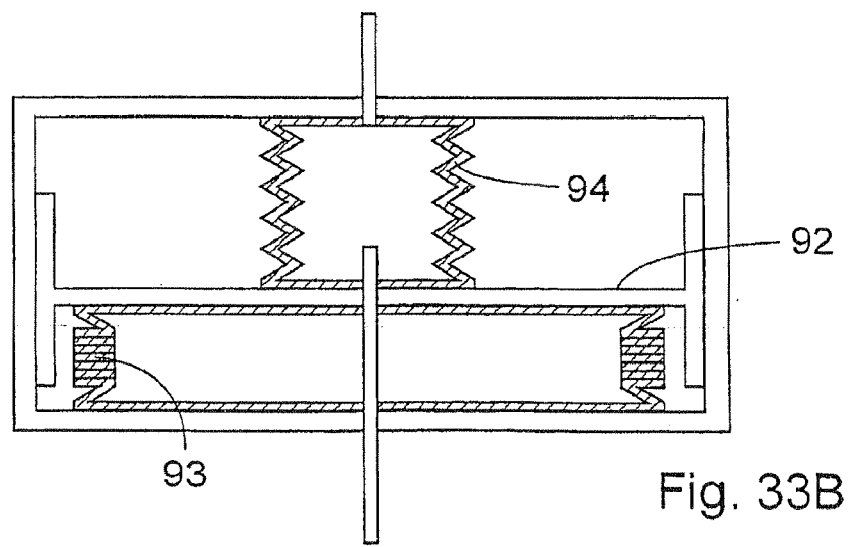

FIGS. 33A and 33B show a reverse servo used for practicing the method of the invention. The reverse servo includes a rectangular housing 91 and an intermediate wall 92, which is movable in the housing 91. A relatively large, substantially cylindrical bellows reservoir 93 is arranged in the housing 91 and is joined to the movable intermediate wall 92. Another cylindrical bellows reservoir 94, which is substantially smaller than reservoir 93, is arranged in the housing 91 at the other side of the intermediate wall 92 and is also joined to the wall 92. The small bellows reservoir 94 has a fluid supply pipe 95 and the large bellows reservoir 93 has a fluid supply pipe 96.

Referring to FIG. 33A, when a small amount of hydraulic fluid is conducted through the supply pipe 95 into the small bellows reservoir 94, the small bellows reservoir 94 expands and pushes the movable intermediate wall 92 towards the large bellows reservoir 93. As a result, the large bellows reservoir 93 is contracted by the intermediate wall 92, whereby a large amount of hydraulic fluid is forced out of the large bellows reservoir 93 through the supply pipe 96, see FIG. 33B.

For example, the reverse servo of FIGS. 33A and 33B may be used in the embodiment of FIG. 31c, wherein the small bellows reservoir 94 corresponds to the small servo reservoir 78 and the large bellows reservoir 93 corresponds to the large reservoir 79. Also, the reverse servo of FIGS. 33A and 33B may be used in the embodiment of FIGS. 30A and 30B, wherein the small bellows reservoir 94 is connected to the adjustable reservoir 74 and the large bellows reservoir 93 is connected to the cavity 73 of the band 72.

Figure 34:
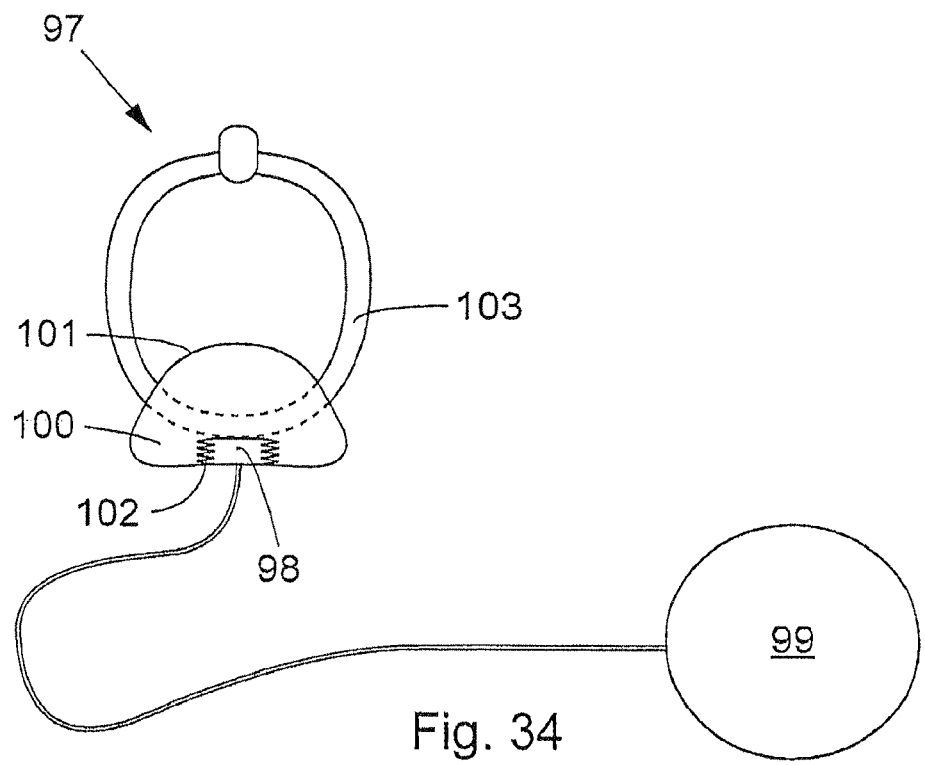
FIG. 34 is a schematic view of another hydraulically operable constriction device for practicing the method according to the present invention.

FIG. 34 schematically shows a hydraulically operable constriction device 97, which is similar to the embodiment shown in FIG. 30A, except that the hydraulic system is designed differently. Thus, the constriction device 97 includes a relatively small inflatable cavity 98, which is in fluid communication with a reservoir 99 containing hydraulic fluid, and a relatively large cavity 100, which is displaceable by small cavity 98. Small cavity 98 is adapted to displace large cavity 100 to constrict the patient's tubular wall portion when small cavity 98 is inflated and to displace large cavity 100 to release the wall portion when small cavity 98 is deflated. Thus, a relatively small addition of hydraulic fluid from reservoir 99 to small cavity 98 causes a relatively large increase in the constriction of the wall portion.

Large cavity 100 is defined by a contraction element in the form of a big balloon 101, which may be connected to an injection port (not shown) for calibration of the volume of large cavity 100. Adding fluid to or withdrawing fluid from the injection port with the aid of a syringe calibrates the volume of balloon 101. Small cavity 98 is defined by a small bellows 102 attached to an annular frame 103 of constriction device 97 and at the opposite end is attached to balloon 101.

Figure 35A:
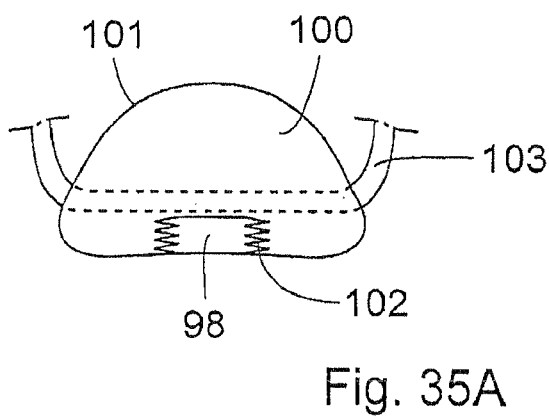
FIG. 35A illustrates the constriction device of FIG. 34 in a constricted state.
Figure 35B:
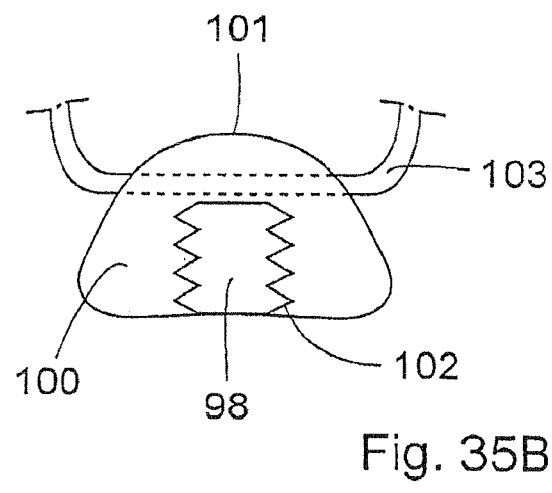
FIG. 35B illustrates the constriction device of FIG. 34 in a released state.

FIGS. 35A and 35B schematically illustrate the operation of constriction device 97, when annular frame 103 is applied around the tubular wall portion of the patient's biliary duct. Referring to FIG. 35A, when small cavity 98 is deflated bellows 102 pulls balloon 101 inwardly into annular frame 103, so that constriction device 97 constricts the wall portion. Referring to FIG. 34B, when small cavity 98 is inflated bellows 102 pulls balloon 101 out of annular frame 103, so that constriction device 97 releases the wall portion.

As mentioned above, the constriction device and stimulation device can co-operate to actively move the bile and/or gall stones in the lumen of a patient's biliary duct. This can be practised by use of the constriction/stimulation unit according to FIG. 2. Thus, in accordance with a first cooperation option, the clamping elements 5, 6 of the constriction device constricts the wall portion 8 without completely closing the biliary duct, and the control device 4 controls the electrical elements 7 to progressively stimulate the constricted wall portion in the downstream or upstream direction of the biliary duct to cause progressive contraction of the wall portion 8 to move the bile and/or gall stones in the biliary duct.

In accordance with a second cooperation option, the constriction device constricts the wall portion so that the movement of bile and/or gallstones in the biliary duct is restricted, and the control device 4 controls a few electrical elements 7 at one end of the elongate clamping elements 5, 6 to stimulate the constricted wall portion 8 to close the biliary duct either at an upstream end or a downstream end of the wall portion 8. With the biliary duct closed in this manner, the control device 4 controls the constriction device to increase the constriction of the wall portion, whereby the bile and/or gall stones in the biliary duct is moved downstream or upstream of the wall portion 8.

Alternatively, the control device 4 controls the stimulation device to stimulate the constricted wall portion 8 while the constriction device varies the constriction of the different areas of the wall portion, so that the wall portion 8 is progressively constricted in the downstream or upstream direction of the biliary duct. FIGS. 36A-36E show different operation stages of such an alternative embodiment. Thus, a constriction device 104 used for practicing the method of the invention includes two elongate constriction elements 105, 106 having convex surfaces 107, 108 that abut a length of the wall portion 8 on mutual sides thereof. A multiplicity of electrical elements 7 (such as electrodes) are positioned on the convex surfaces 107, 108. The control device 4 controls the electrical elements 7 during operation of the constriction device 104 to stimulate the wall portion 8 and controls the elongate constriction elements 105, 106 to move relative to the tubular wall portion 8 so that the constriction elements 105, 106 progressively constrict the wall portion 8, as appears from FIGS. 36A to 36D.

Figure 36:
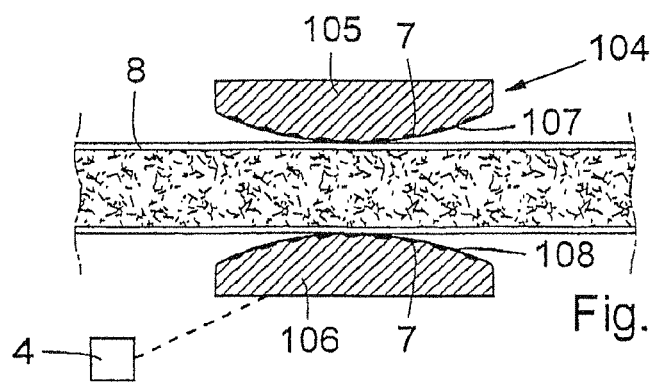
FIGS. 36A-36E schematically illustrate different operation stages of an embodiment of the invention, in which a constriction device and a stimulation device used for practicing the method of the invention co-operate to move the bile and/or gall stones in the biliary duct.
Figure 36:
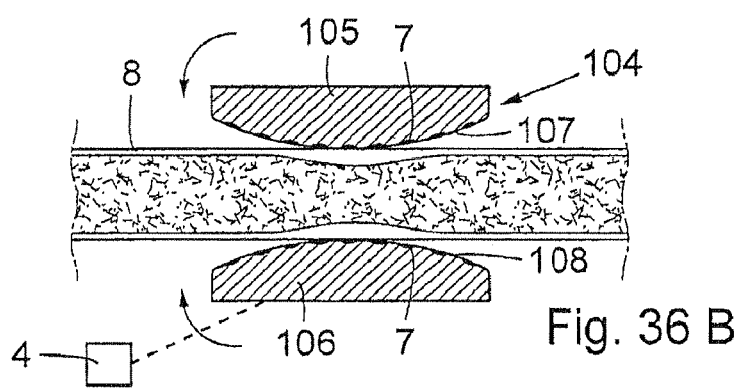
Figure 36:
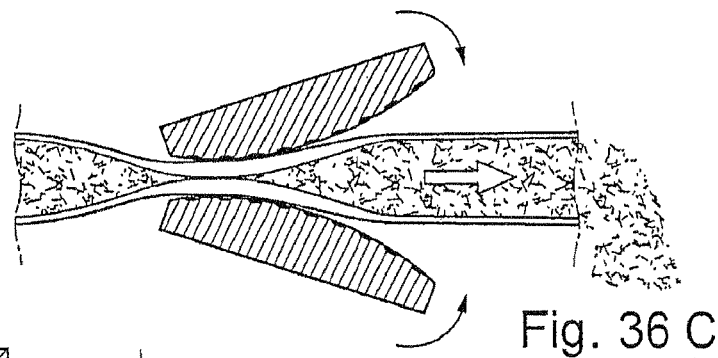
Figure 36:
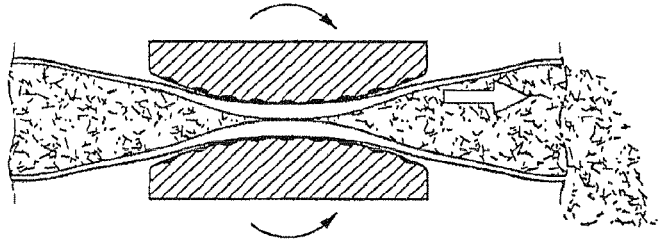
Figure 36:
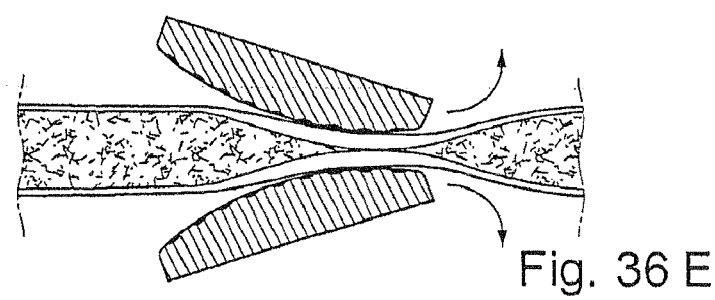

Thus, in an initial position of the constriction elements 105, 106 shown in FIG. 36A, the wall portion is not constricted by the constriction elements 105, 106 and the electrical elements 7 are not energized. Starting from this initial position, the control device 4 controls the constriction elements 105, 106 to swing the left ends of the constriction elements 105, 106 toward the wall portion (indicated by arrows) to constrict the tubular wall portion 8, see FIG. 36B, while energizing the electrical elements 7, so that the electrical elements 7 that contact the wall portion 8 contract the latter. FIG. 36 C shows how the lumen of the tubular wall portion 8 is completely closed by the thickened wall portion 8. Then, as shown in FIG. 36C, the control device 4 controls the constriction elements 105, 106 to move so that their right ends are moving towards each other (indicated by arrows), while the convex surfaces 107, 108 of the constriction elements 105, 106 are rolling on each other with the contracted wall portion 8 between them, see FIG. 36D. As a result, the bile and/or gallstones in the lumen of the biliary duct are forced to the right (indicated by a white arrow). When the constriction elements 105, 106 have rolled on each other to the position shown in FIG. 36E, the control device 4 controls the right ends of the constriction elements 105, 106 to move away from each other (indicated by arrows in FIG. 36E) to the initial position shown in FIG. 36A. The operation stages described according to FIGS. 36A to 36E can be cyclically repeated a number of times until the desired amount of bile and/or gallstones has been moved in the lumen of the biliary duct in a peristaltic manner.

Alternatively, only one of the constriction elements 105, 106 can be provided with a convex surface, whereas the other constriction element has a plane surface that abuts the wall portion. It is also possible to use a single constriction element with a convex surface that presses the tubular portion 8 of the biliary duct against bone or other tissue of the patient.

In the embodiment according to FIGS. 36A to 36E, the control device 4 may control the electrical elements 7 to progressively stimulate the constricted wall portion 8 to cause progressive contraction thereof in harmony with the movement of the elongate constriction elements 105, 106, as the convex surfaces 107, 108 of the constriction elements 105, 106 are rolling on each other.

Figure 37:
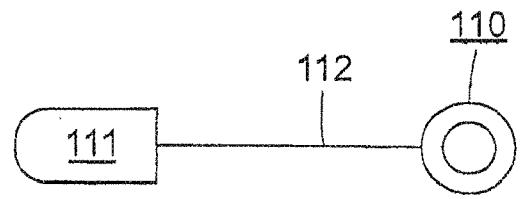
FIGS. 37 to 49 are schematic block diagrams illustrating twelve embodiments, respectively, of an apparatus used for practicing the method of the invention, wherein wireless energy is transmitted from outside a patient's body to energy consuming components of the apparatus implanted in the patient.

FIG. 37 schematically shows a general embodiment of the apparatus of the invention, in which energy is transferred to energy consuming components of the apparatus implanted in the patient.

The apparatus of FIG. 37 comprises an implanted constriction/stimulation unit 109, which is operable to gently constrict a portion of a tubular tissue wall of a patient's biliary duct and to stimulate different areas of the constricted portion to cause contraction of the wall portion. The constriction device of the constriction/stimulation unit 110 is capable of performing a reversible function, i.e., to constrict and release the wall portion, so that the constriction/stimulation unit 110 works as an artificial sphincter.

A source of energy 111 is adapted to supply energy consuming components of the constriction/stimulation unit 110 with energy via a power supply line 112. A wireless remote control or a subcutaneously implanted switch operable by the patient to switch on or off the supply of energy from the source of energy may be provided. The source of energy may be an implantable permanent or rechargeable battery, or be included in an external energy-transmission device, which may be operable directly by the patient or be controlled by a remote control operable by the patient to transmit wireless energy to the energy consuming components of the constriction/stimulation unit. Alternatively, the source of energy may comprise a combination of an implantable rechargeable battery, an external energy-transmission device and an implantable energy-transforming device for transforming wireless energy transmitted by the external energy-transmission device into electric energy for the charge of the implantable rechargeable battery.

Figure 38:
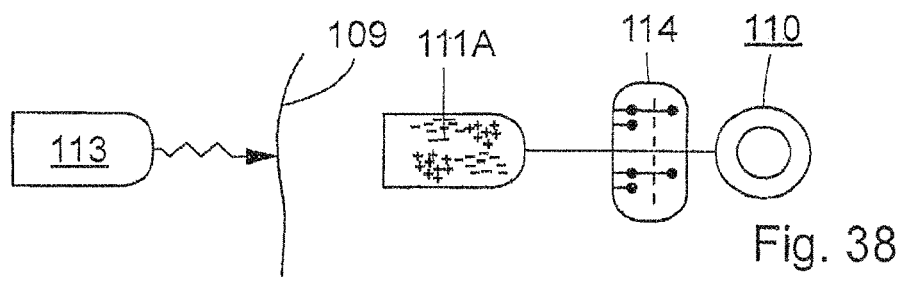

FIG. 38 shows a special embodiment of the general embodiment of FIG. 37 having some parts implanted in a patient and other parts located outside the patient's body. Thus, in FIG. 38 all parts placed to the right of the patient's skin 109 are implanted and all parts placed to the left of the skin 109 are located outside the patient's body. An implanted energy-transforming device 111A of the apparatus is adapted to supply energy consuming components of the constriction/stimulation unit 110 with energy via the power supply line 112. An external energy-transmission device 113 of the apparatus includes a wireless remote control transmitting a wireless signal, which is received by a signal receiver incorporated in the implanted energy-transforming device 111A. The implanted energy-transforming device 111A transforms energy from the signal into electric energy which is supplied via the power supply line 112 to the constriction/stimulation unit 110.

The apparatus of FIG. 3 (may also include an implanted rechargeable battery for energizing energy consuming implanted components of the apparatus. In this case, the implanted energy-transforming device 111A also charges the battery with electric energy, as the energy-transforming device transforms energy from the signal into the electric energy.

A reversing device in the form of an electric switch 114, such as a microprocessor, is implanted in the patient for reversing the constriction device of the constriction/stimulation unit 110. The wireless remote control of the external energy-transmission device 113 transmits a wireless signal that carries energy and the implanted energy-transforming device 111A transforms the wireless energy into a current for operating the switch 114. When the polarity of the current is shifted by the energy-transforming device 111A the switch 114 reverses the function performed by the constriction device of the constriction/stimulation unit 110.

Figure 39:
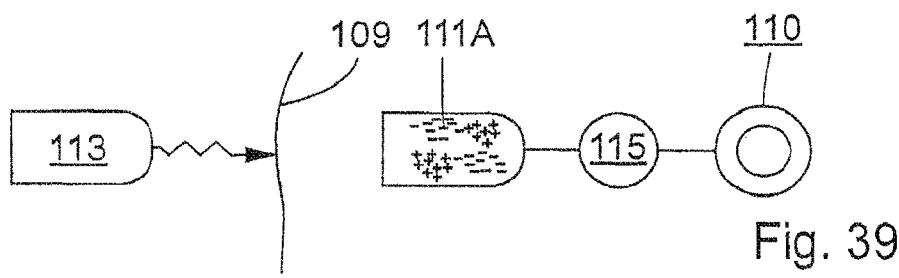

FIG. 39 shows another embodiment of the invention including the energy-transforming device 111A, the constriction/stimulation unit 110 and an operation device in the form of a motor 115 for operating the constriction device of the constriction/stimulation unit 110. The motor 115 is powered with energy from the energy-transforming device 111A, as the remote control of the external energy-transmission device 113 transmits a wireless signal to the receiver of the energy-transforming device 111A.

Figure 40:
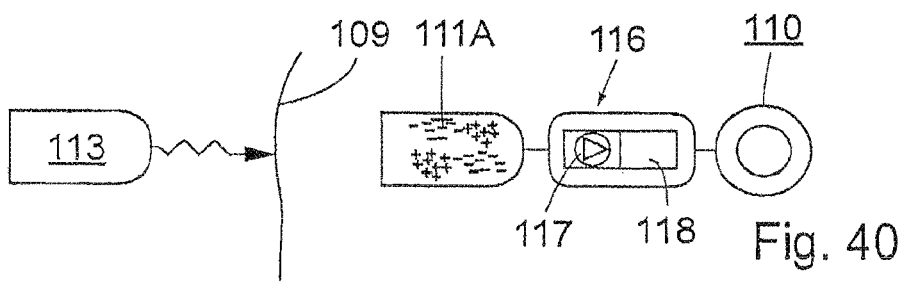

FIG. 40 shows yet another embodiment of the invention including the energy-transforming device 111A, the constriction/stimulation unit 110 and an assembly 116 including a motor/pump unit 117 and a fluid reservoir 118. In this case the constriction device of the constriction/stimulation unit 110 is hydraulically operated, i.e., hydraulic fluid is pumped by the motor/pump unit 117 from the reservoir 118 to the constriction/stimulation unit 110 to constrict the wall portion, and hydraulic fluid is pumped by the motor/pump unit 117 back from the constriction/stimulation unit 110 to the reservoir 118 to release the wall portion. The implanted energy-transforming device 111A transforms wireless energy into a current, for powering the motor/pump unit 117.

Figure 41:
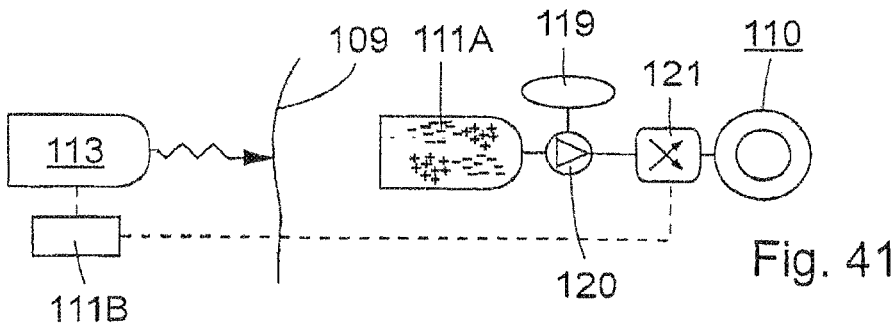
Figure 42:
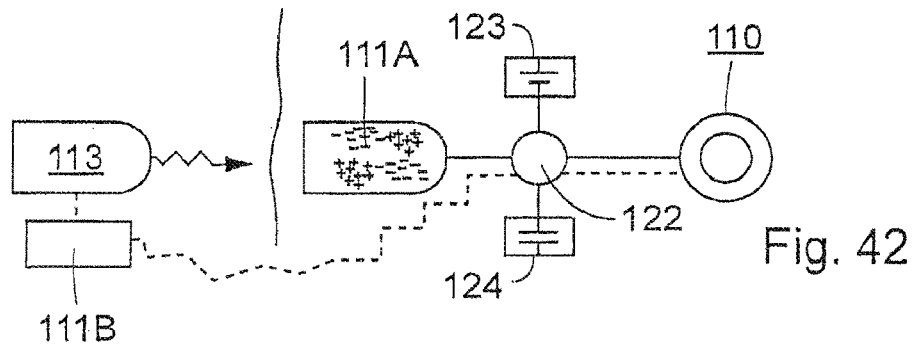

FIG. 41 shows another embodiment of an apparatus used for practicing the method of the invention. The apparatus of FIG. 41 comprises the external energy-transmission device 113 that controls the control unit 122 to reverse the motor 115 when needed, the constriction/stimulation unit 110, the constriction device of which is hydraulically operated, and the implanted energy-transforming device 111A, and further comprises an implanted hydraulic fluid reservoir 119, an implanted motor/pump unit 120, an implanted reversing device in the form of a hydraulic valve shifting device 121 and a separate external wireless remote control 111B. The motor of the motor/pump unit 120 is an electric motor. In response to a control signal from the wireless remote control of the external energy-transmission device 113, the implanted energy-transforming device 111A powers the motor/pump unit 120 with energy from the energy carried by the control signal, whereby the motor/pump unit 120 distributes hydraulic fluid between the reservoir 119 and the constriction device of the constriction/stimulation unit 110. The remote control 111B controls the shifting device 121 to shift the hydraulic fluid flow direction between one direction in which the fluid is pumped by the motor/pump unit 120 from the reservoir 119 to the constriction device of the constriction/stimulation unit 110 to constrict the wall portion, and another opposite direction in which the fluid is pumped by the motor/pump unit 120 back from the constriction device of the constriction/stimulation unit 110 to the reservoir 119 to release the wall portion, FIG. 42 shows an embodiment of the invention including the energy-transforming device 111A and the constriction/stimulation unit 110. A control unit 122, an accumulator 123 and a capacitor 124 are also implanted in the patient. A separate external wireless remote control 111B controls the control unit 122. The control unit 122 controls the energy-transforming device 111A to store electric energy in the accumulator 123, which supplies energy to the constriction/stimulation unit 110. In response to a control signal from the wireless remote control 111B, the control unit 122 either releases electric energy from the accumulator 123 and transfers the released energy via power lines, or directly transfers electric energy from the energy-transforming device 111A via the capacitor 124, which stabilizes the electric current, for the operation of the constriction/stimulation unit 110.

In accordance with one alternative, the capacitor 124 in the apparatus of FIG. 42 may be omitted. In accordance with another alternative, the accumulator 123 in this apparatus may be omitted.

Figure 43:
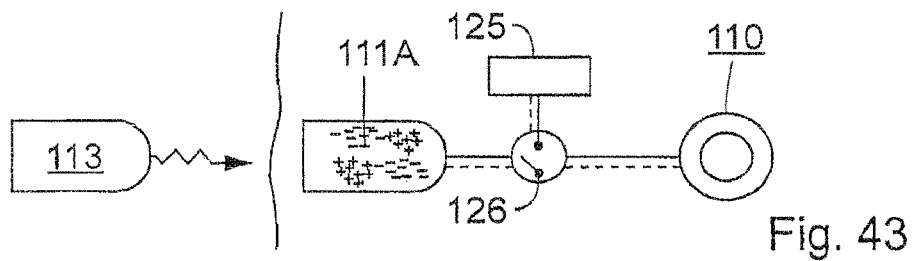

FIG. 43 shows an embodiment of the invention including the energy-transforming device 111A, the constriction/stimulation unit 110. A battery 125 for supplying energy for the operation of the constriction/stimulation unit 110 and an electric switch 126 for switching the operation of the constriction/stimulation unit 110 are also implanted in the patient. The switch 126 is operated by the energy supplied by the energy-transforming device 111A to switch from an off mode, in which the battery 125 is not in use, to an on mode, in which the battery 125 supplies energy for the operation of the constriction/stimulation unit 110.

Figure 44:
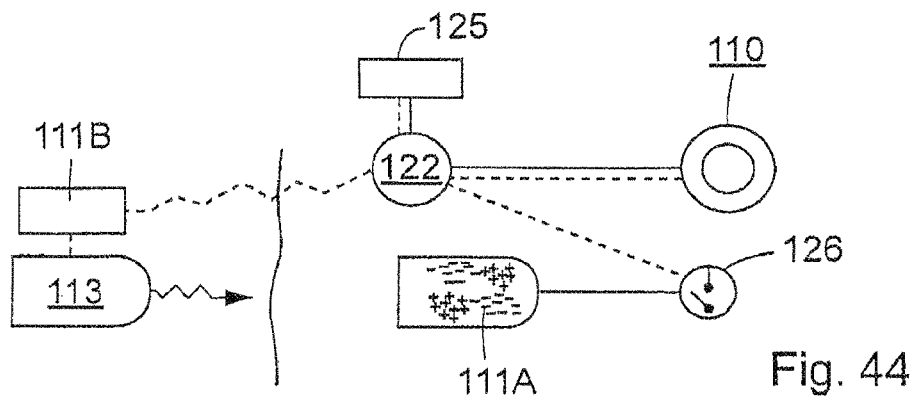

FIG. 44 shows an apparatus identical to that of FIG. 43, except that a control unit 122 also is implanted in the patient. A separate external wireless remote control 1118 controls the control unit 122. In this case, the switch 126 is operated by the energy supplied by the energy-transforming device 111A to switch from an off mode, in which the wireless remote control 111B is prevented from controlling the control unit 122 and the battery 125 is not in use, to a standby mode, in which the remote control 111B is permitted to control the control unit 122 to release electric energy from the battery 125 for the operation of the constriction/stimulation unit 110.

Figure 45:
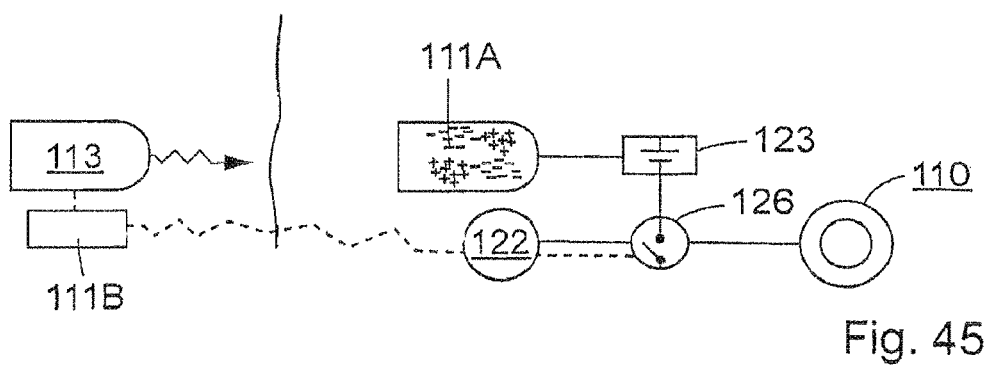

FIG. 45 shows an apparatus identical to that of FIG. 44, except that the accumulator 123 is substituted for the battery 125 and the implanted components are interconnected differently. In this case, the accumulator 123 stores energy from the energy-transforming device 111A. In response to a control signal from the wireless remote control 111B, the implanted control unit 122 controls the switch 126 to switch from an off mode, in which the accumulator 123 is not in use, to an on mode, in which the accumulator 123 supplies energy for the operation of the constriction/stimulation unit 110.

Figure 46:
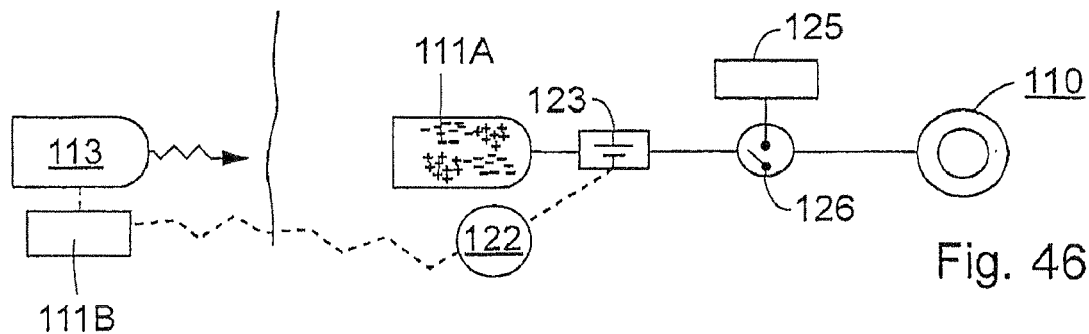

FIG. 46 shows an apparatus identical to that of FIG. 45, except that the battery 125 also is implanted in the patient and the implanted components are interconnected differently. In response to a control signal from the wireless remote control 111B, the implanted control unit 122 controls the accumulator 123, which may be a capacitor, to deliver energy for operating the switch 126 to switch from an off mode, in which the battery 125 is not in use, to an on mode, in which the battery 125 supplies electric energy for the operation of the constriction/stimulation unit 110.

Alternatively, the switch 126 may be operated by energy supplied by the accumulator 123 to switch from an off mode, in which the wireless remote control 111B is prevented from controlling the battery 125 to supply electric energy and the battery 125 is not in use, to a standby mode, in which the wireless remote control 111B is permitted to control the battery 125 to supply electric energy for the operation of the constriction/stimulation unit 110.

Figure 47:
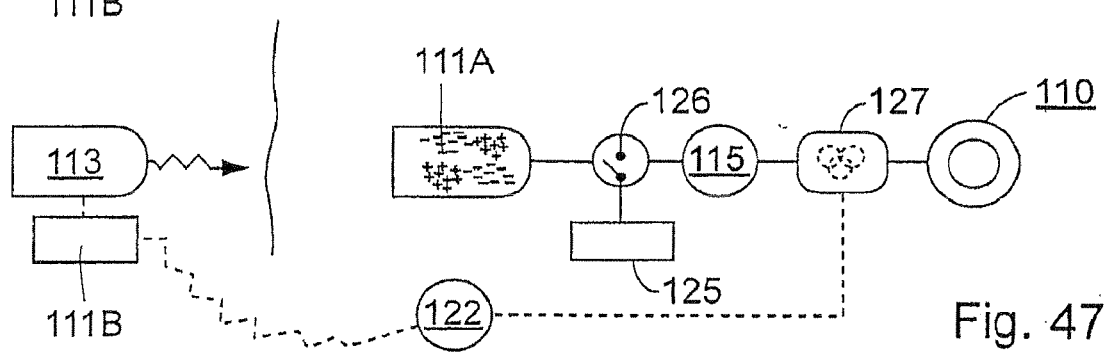

FIG. 47 shows an apparatus identical to that of FIG. 43, except that a motor 115, a mechanical reversing device in the form of a gearbox 127 and a control unit 122 for controlling the gearbox 127 also are implanted in the patient. A separate external wireless remote control 111B controls the implanted control unit 122 to control the gearbox 127 to reverse the function performed by the constriction device (mechanically operated) of the constriction/stimulation unit 110.

Figure 48:
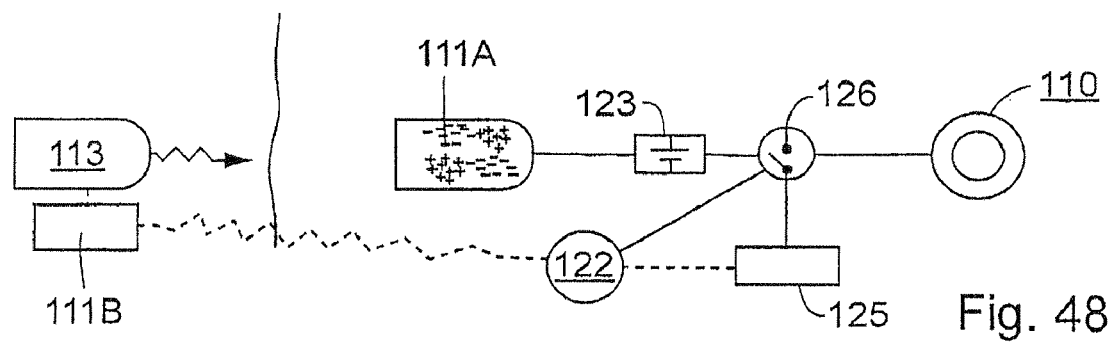

FIG. 48 shows an apparatus identical to that of FIG. 46 except that the implanted components are interconnected differently. Thus, in this case the battery 125 powers the control unit 122 when the accumulator 123, suitably a capacitor, activates the switch 126 to switch to an on mode. When the switch 126 is in its on mode the control unit 122 is permitted to control the battery 125 to supply, or not supply, energy for the operation of the constriction/stimulation unit 110.

Figure 49:
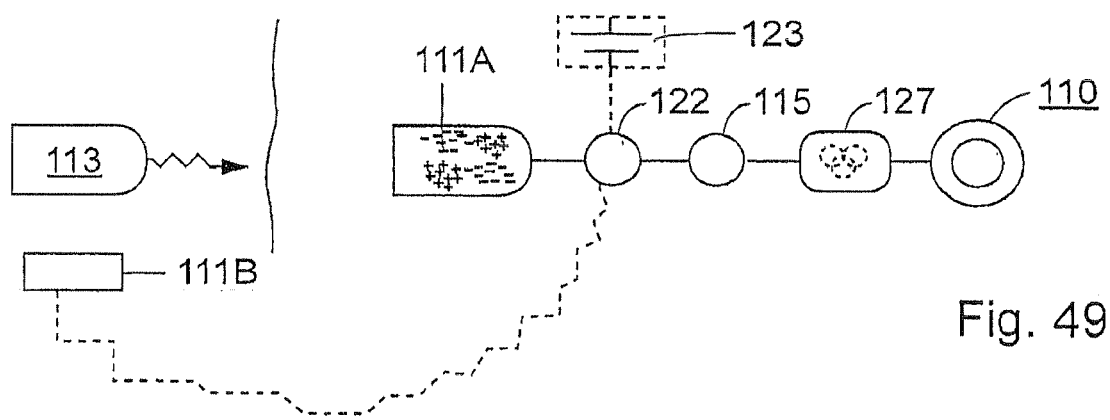

FIG. 49 shows an embodiment of the invention identical to that of FIG. 39, except that a gearbox 127 that connects the motor 115 to the constriction/stimulation unit 110, and a control unit 122 that controls the energy-transforming device 111A to power the motor 115 also are implanted in the patient. There is a separate external wireless remote control 111B that controls the control unit 122 to reverse the motor 115 when needed.

Optionally, the accumulator 123 shown in FIG. 42 may be provided in the embodiment of FIG. 49, wherein the implanted control unit 122 controls the energy-transforming device 111A to store the transformed energy in the accumulator 123. In response to a control signal from the wireless remote control 111B, the control unit 122 controls the accumulator 123 to supply energy for the operation of the constriction/stimulation unit 110.

Any of the apparatuses of FIGS. 36-49 can be used for practicing the method of the invention.

Those skilled in the art will realize that the above various embodiments according to FIGS. 38-49 could be combined in many different ways. For example, the energy operated switch 114 could be incorporated in any of the embodiments of FIGS. 39, 42-49, the hydraulic shifting device 121 could be incorporated in the embodiment of FIG. 40, and the gearbox 127 could be incorporated in the embodiment of FIG. 39. The switch 114 may be of a type that includes electronic components, for example a microprocessor, or a FGPA (Field Programmable Gate Array) designed for switching. Alternatively, however, the energy operated switch 114 may be replaced by a subcutaneously implanted push button that is manually switched by the patient between "on" and "off".

Alternatively, a permanent or rechargeable battery may be substituted for the energy-transforming devices 111A of the embodiments shown in FIGS. 38-49.

Figure 50:
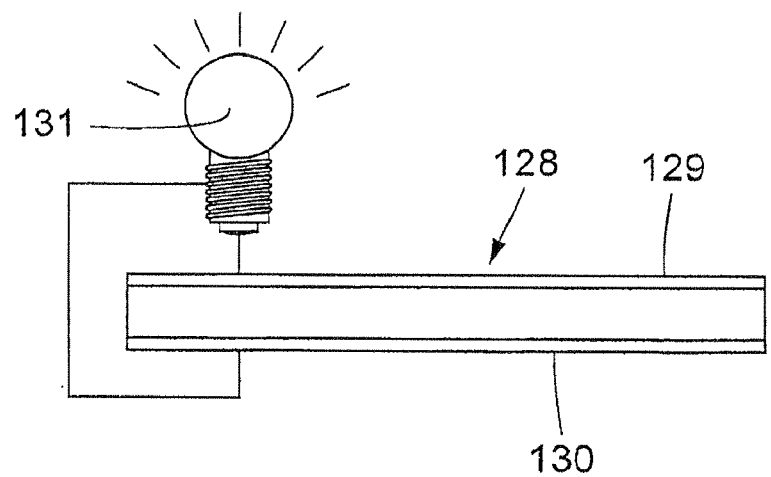
FIG. 50 illustrates an energy-transforming device in the form of an electrical junction element used for practicing the method of the invention.

FIG. 50 shows the energy-transforming device in the form of an electrical junction element 128 for use in any of the above embodiments according to FIGS. 37-49. The element 128 is a flat p-n junction element comprising a p-type semiconductor layer 129 and an n-type semiconductor layer 130 sandwiched together. A light bulb 131 is electrically connected to opposite sides of the element 128 to illustrate how the generated current is obtained. The output of current from such a p-n junction element 128 is correlated to the temperature. See the formula below.

$$I = I0(\exp(qV/kT)-1)$$

where

I is the external current flow,

I0 is the reverse saturation current, q is the fundamental electronic charge of $1.602 \times 10^{-19}$ coulombs, V is the applied voltage, k is the Boltzmann constant, and T is the absolute temperature.

Under large negative applied voltage (reverse bias), the exponential term becomes negligible compared to 1.0, and I is approximately −I0. I0 is strongly dependent on the temperature of the junction and hence on the intrinsic-carrier concentration. I0 is larger for materials with smaller bandgaps than for those with larger bandgaps. The rectifier action of the diode, that is, its restriction of current flow to only one direction, is in this particular embodiment the key to the operation of the p-n junction element 128.

The alternative way to design a p-n junction element is to deposit a thin layer of semiconductor onto a supporting material which does not absorb the kind of energy utilized in the respective embodiments. For use with wirelessly transmitted energy in terms of light waves, glass could be a suitable material. Various materials may be used in the semiconductor layers such as but not limited to cadmium telluride, copper-indium-diselenide and silicon. It is also possible to use a multilayer structure with several layers of p and n-type materials to improve efficiency.

The electric energy generated by the p-n junction element 128 could be of the same type as generated by solar cells, in which the negative and positive fields create a direct current. Alternatively, the negative and positive semiconductor layers may change polarity following the transmitted waves, thereby generating the alternating current.

The p-n junction element 128 is designed to make it suited for implantation. Thus, all the external surfaces of the element 128 in contact with the human body are made of a biocompatible material. The p-n junction semiconductors are designed to operate optimally at a body temperature of 37° C. because the current output, which should be more than 1 µA, is significantly depending on temperature as shown above. Since both the skin and subcutis absorb energy, the relation between the sensitivity or working area of the element 128 and the intensity or strength of the wireless energy-transmission is considered. The p-n junction element 128 preferably is designed flat and small. Alternatively, if the element 128 is made in larger sizes it should be flexible, in order to adapt to the patient's body movements. The volume of the element 128 should be kept less than 2000 cm³.

Figure 51:
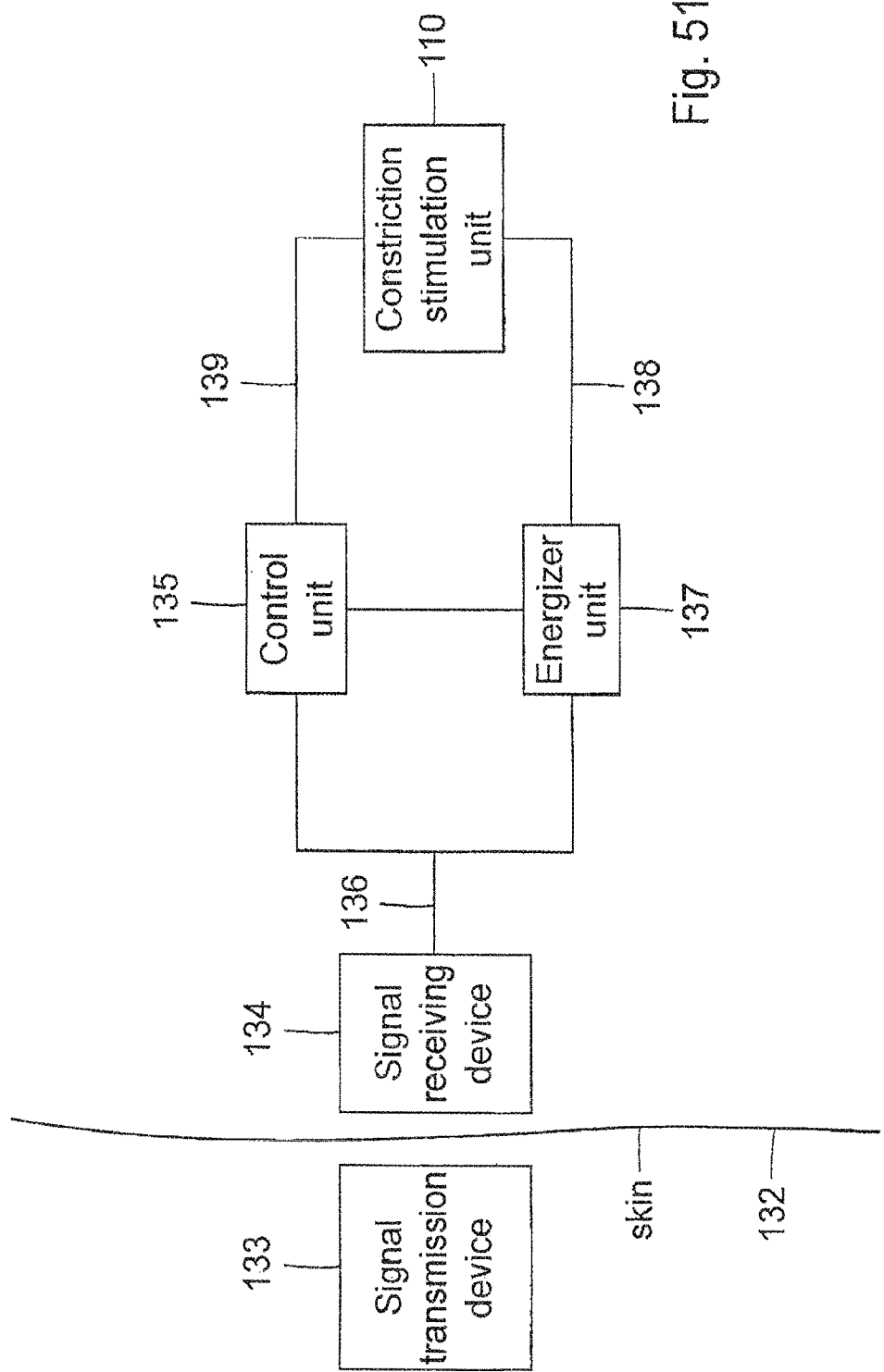
FIG. 51 is a block diagram illustrating control components used for practicing the method of the invention.

FIG. 51 shows basic parts of a remote control used for practicing the method of the invention. The remote control controls the constriction/stimulation unit 110. In this case, the stimulation device of the constriction/stimulation unit stimulates the wall portion of the patient's biliary duct with electric pulses. The remote control is based on wireless transmission of electromagnetic wave signals, often of high frequencies in the order of 100 kHz-1 gHz, through the skin 132 of the patient. In FIG. 51, all parts placed to the left of the skin 132 are located outside the patient's body and all parts placed to the right of the skin 132 are implanted.

An external signal-transmission device 133 is to be positioned close to a signal-receiving device 134 implanted close to the skin 132. As an alternative, the signal-receiving device 134 may be placed for example inside the abdomen of the patient. The signal-receiving device 134 comprises a coil, approximately 1-100 mm, preferably 25 mm in diameter, wound with a very thin wire and tuned with a capacitor to a specific high frequency. A small coil is chosen if it is to be implanted under the skin of the patient and a large coil is chosen if it is to be implanted in the abdomen of the patient. The signal transmission device 133 comprises a coil having about the same size as the coil of the signal-receiving device 134 but wound with a thick wire that can handle the larger currents that is necessary. The coil of the signal transmission device 133 is tuned to the same specific high frequency as the coil of the signal-receiving device 134.

The signal-transmission device 133 is adapted to send digital information via the power amplifier and signal-receiving device 134 to an implanted control unit 135. To avoid that accidental random high frequency fields trigger control commands, digital signal codes are used. A conventional keypad placed on the signal transmission device 133 is used to order the signal transmission device 133 to send digital signals for the control of the constriction/stimulation unit. The signal transmission device 133 starts a command by generating a high frequency signal. After a short time, when the signal has energized the implanted parts of the control system, commands are sent to operate the constriction device of the constriction/stimulation unit 110 in pre-defined steps. The commands are sent as digital packets in the form illustrated below.

| Start pattern, 8 bits | Command, 8 bits | Count, 8 bits | Checksum, 8 bits |
|---|---|---|---|

The commands are sent continuously during a rather long time period (e.g. about 30 seconds or more). When a new constriction or release step is desired the Count byte is increased by one to allow the implanted control unit 135 to decode and understand that another step is demanded by the signal transmission device 133. If any part of the digital packet is erroneous, its content is simply ignored.

Through a line 136, an implanted energizer unit 137 draws energy from the high frequency electromagnetic wave signals received by the signal-receiving device 134. The energizer unit 137 stores the energy in a source of energy, such as a large capacitor, powers the control unit 135 and powers the constriction/stimulation unit 110 via a line 138.

The control unit 135 comprises a demodulator and a microprocessor. The demodulator demodulates digital signals sent from the signal transmission device 133. The microprocessor receives the digital packet, decodes it and sends a control signal via a signal line 139 to control the constriction device of the constriction/stimulation unit 110 to either constrict or release the wall portion of the patient's biliary duct depending on the received command code.

Figure 52:
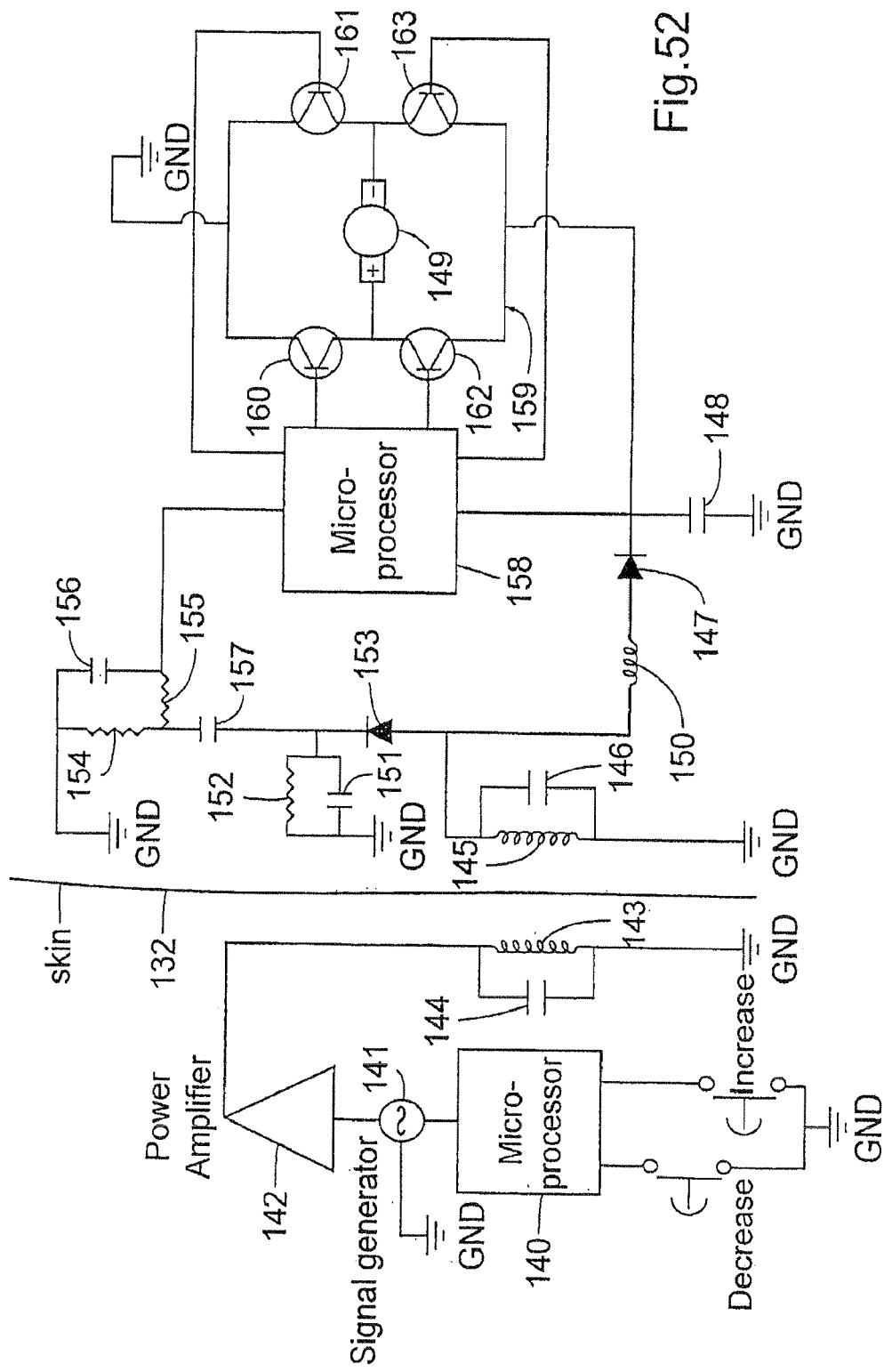
FIG. 52 is a schematic view of exemplary circuitry of an embodiment of the invention, in which wireless energy is transformed into a current.

FIG. 52 shows a circuitry of an embodiment of the invention, in which wireless energy is transformed into a current. External components of the circuitry include a microprocessor 140, a signal generator 141 and a power amplifier 142 connected thereto. The microprocessor 140 is adapted to switch the signal generator 141 on/off and to modulate signals generated by the signal generator 141 with digital commands. The power amplifier 142 amplifies the signals and sends them to an external signal-transmitting antenna 143. The antenna 143 is connected in parallel with a capacitor 144 to form a resonant circuit tuned to the frequency generated by the signal generator 141.

Implanted components of the circuitry include a signal receiving antenna coil 145 and a capacitor 146 forming together a resonant circuit that is tuned to the same frequency as the transmitting antenna 143. The signal receiving antenna coil 145 induces a current from the received high frequency electromagnetic waves and a rectifying diode 147 rectifies the induced current, which charges a storage capacitor 148. The storage capacitor 148 powers a motor 149 for driving the constriction device of the constriction/stimulation unit 110. A coil 150 connected between the antenna coil 145 and the diode 147 prevents the capacitor 148 and the diode 147 from loading the circuit of the signal-receiving antenna 145 at higher frequencies. Thus, the coil 150 makes it possible to charge the capacitor 148 and to transmit digital information using amplitude modulation.

A capacitor 151 and a resistor 152 connected in parallel and a diode 153 forms a detector used to detect amplitude modulated digital information. A filter circuit is formed by a resistor 154 connected in series with a resistor 155 connected in series with a capacitor 156 connected in series with the resistor 154 via ground, and a capacitor 157, one terminal of which is connected between the resistors 154, 155 and the other terminal of which is connected between the diode 153 and the circuit formed by the capacitor 151 and resistor 152. The filter circuit is used to filter out undesired low and high frequencies. The detected and filtered signals are fed to an implanted microprocessor 158 that decodes the digital information and controls the motor 149 via an H-bridge 159 comprising transistors 160,161,162 and 163. The motor 149 can be driven in two opposite directions by the H-bridge 159.

The microprocessor 158 also monitors the amount of stored energy in the storage capacitor 148. Before sending signals to activate the motor 149, the microprocessor 158 checks whether the energy stored in the storage capacitor 148 is enough. If the stored energy is not enough to perform the requested operation, the microprocessor 158 waits for the received signals to charge the storage capacitor 148 before activating the motor 149.

Alternatively, the energy stored in the storage capacitor 148 may only be used for powering a switch, and the energy for powering the motor 149 may be obtained from another implanted energy source of relatively high capacity, for example a battery. In this case the switch is adapted to connect the battery to the motor 149 in an on mode when the switch is powered by the storage capacitor 148 and to keep the battery disconnected from the motor 149 in a standby mode when the switch is not powered.

Figure 53A:
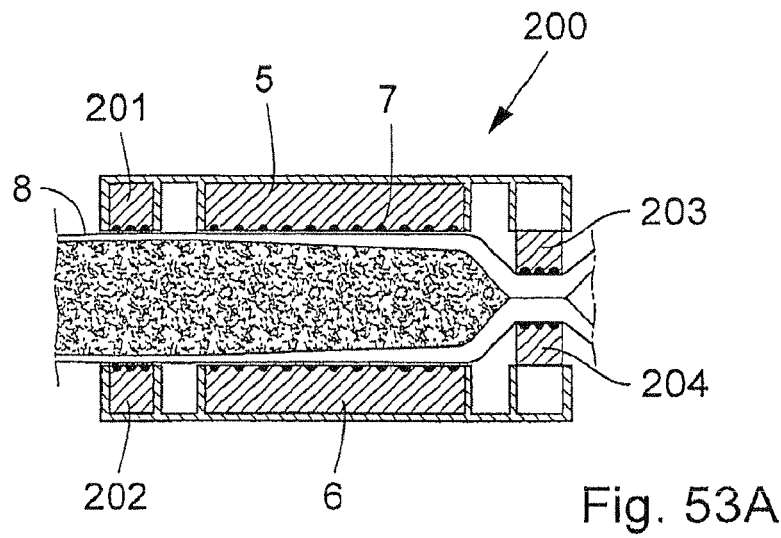
FIGS. 53A-53C schematically illustrate different operation stages of another embodiment of the invention of the type shown in FIG. 2 used for practicing the method of the invention, wherein a constriction device and a stimulation device co-operate to move the bile and/or gall stones in the lumen of a patient's biliary duct.
Figure 53B:
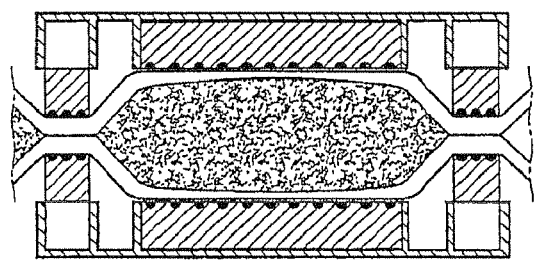
Figure 53C:
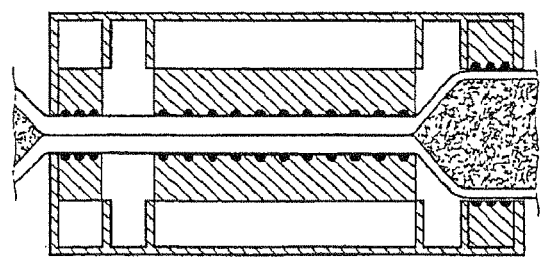

FIGS. 53A-53C show an apparatus used for practicing the method of the invention which is similar to the apparatus of FIG. 2, except that the constriction/stimulation unit, here denoted by reference numeral 200, is provided with additional clamping elements. The apparatus of FIGS. 53A-53C is suited for actively moving the bile and/or gall stones in the lumen of a patient's biliary duct. Thus, the constriction/stimulation unit 200 also includes a first pair of short clamping elements 201 and 202, and a second pair of short clamping elements 203 and 204, wherein the first and second pairs of clamping elements are positioned at mutual sides of the elongate clamping elements 5,6. The two short clamping elements 201, 202 of the first pair are radially movable towards and away from each other between retracted positions (FIG. 53A) and clamping positions (FIGS. 53B and 53C), and the two short clamping elements 203, 204 of the second pair are radially movable towards and away from each other between retracted positions (FIG. 53C) and clamping positions (FIGS. 53A and 53B). The stimulation device 3 also includes electrical elements 7 positioned on the short clamping elements 201-204, so that the electrical elements 7 on one of the short clamping elements 201 and 203, respectively, of each pair of short elements face the electrical elements 7 on the other short clamping element 202 and 204, respectively, of each pair of short elements.

The constriction/stimulation unit 200 is applied on a wall portion 8 of a tubular tissue wall of a patient's biliary duct, so that the short clamping elements 201, 202 are positioned at an upstream end of the wall portion 8, whereas the short clamping elements 203, 204 202 are positioned at a downstream end of the wall portion 8. In FIGS. 53A to 53C the upstream end of the wall portion 8 is to the left and the downstream end of the wall portion 8 is to the right.

The control device 4 controls the pair of short clamping elements 201, 202, the pair of elongate clamping elements 5, 6 and the pair of short elements 203, 204 to constrict and release the wall portion 8 independently of one another. The control device also controls the electrical elements 7 on a clamping element that is constricting the wall portion to stimulate the constricted wall portion 8 with electric pulses to cause contraction of the wall portion 8, so that the lumen of the wall portion 8 is closed.

FIGS. 53A-53C illustrate how the control device 4 controls the operation of the constriction/stimulation unit 200 to cyclically move bile and/or gall stones downstream in the lumen of the wall portion 8. Thus, in FIG. 53A the short clamping elements 201, 202 and the elongate clamping elements 5, 6 are in their retracted positions, whereas the short clamping elements 203, 204 are in their clamping positions while the electrical elements 7 on elements 203, 204 electrically stimulate the wall portion 8. The electrical stimulation causes the wall portion 8 at the elements 203, 204 to thicken, whereby the biliary duct is closed. FIG. 53B illustrates how also the short clamping elements 201, 202 have been moved radially inwardly to their clamping positions while the electrical elements 7 on elements 201, 202 electrically stimulate the wall portion 8, whereby a volume of bile and/or gallstones is trapped in the lumen between the upstream and downstream ends of the wall portion 8. FIG. 53C illustrates how initially the short clamping elements 203, 204 have been moved radially outwardly to their retracted positions, and then the elongate clamping elements 5, 6 have been moved radially inwardly to their clamping positions while the electrical elements 7 on elements 5, 6 electrically stimulate the wall portion 8. As a result, the bile and/or gallstones in the lumen between the upstream and downstream ends of the wall portion 8 has been moved downstream in the lumen as indicated by an arrow. Then, the control device 4 controls the constriction/stimulation unit 200 to assume the state shown in FIG. 53A, whereby bile and/or gallstones may flow into and fill the lumen between the upstream and downstream ends of the wall portion 8, so that the cycle of the operation is completed.

Alternatively, the operation cycle of the constriction/ stimulation unit 200 described above may be reversed, in order to move bile and/or gallstones upstream in the lumen. In this case the control device 4 controls the short clamping elements 203, 204 to constrict the wall portion 8 at the downstream end thereof to restrict the movement of bile and/or gallstones in the biliary duct and controls the electric elements 7 to stimulate the constricted wall portion 8 with electric pulses at the downstream end to close the biliary duct. With the biliary duct closed at the downstream end of the constricted wall portion 8 and the short clamping elements 201, 202 in their retracted positions, as shown in FIG. 53A, the control device 4 controls the elongate clamping elements 5, 6 to constrict the wall portion 8 between the upstream and downstream ends thereof. As a result, the bile and/or gall stones contained in the wall portion 8 between the upstream and downstream ends thereof is moved upstream in the biliary duct.

Although FIGS. 53A-53C disclose pairs of clamping elements, it should be noted that it is conceivable to design the constriction/stimulation unit 200 with only a single short clamping element 201, a single elongate clamping element 5 and a single short clamping element 203. In this case the bottom of the tubular wall portion 8 is supported by stationary elements of the constriction/stimulation unit 200 opposite to the clamping elements 201, 5, 203.

Figure 54A:
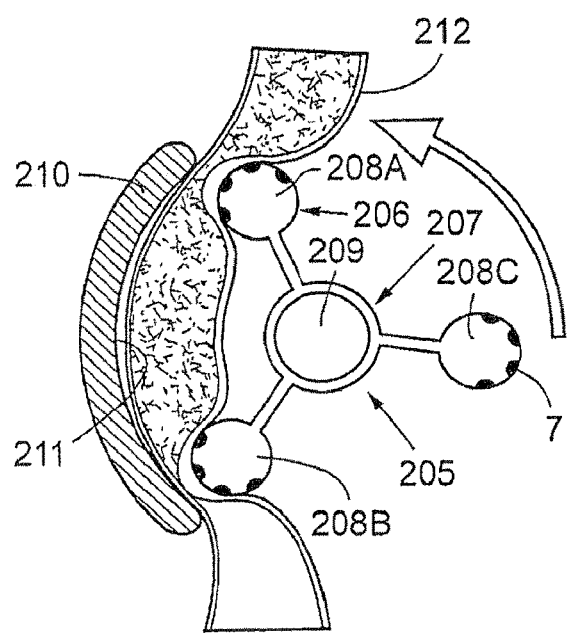
FIGS. 54A-54B schematically illustrate different operation stages of another apparatus of the type shown in FIGS. 36A-36E used for practicing the method of the invention, wherein a constriction device and a stimulation device co-operate to move the bile and/or gall stones in the lumen of a patient's biliary duct.
Figure 54B:
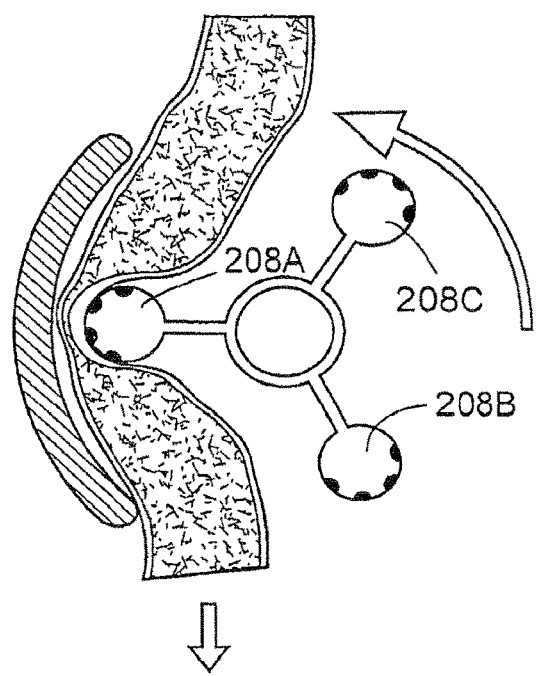

FIGS. 54A and 54B schematically show another apparatus used for practicing the method of the invention, in particular for actively moving the bile and/or gall stones in the lumen of a patient's biliary duct. The apparatus of FIGS. 54A and 54B includes a constriction/stimulation unit 205, the constriction device 206 of which has a rotor 207, which carries three cylindrical constriction elements 208A, 208B and 208C positioned equidistantly from the axis 209 of the rotor 207. The constriction elements 208A-208C may be designed as rollers. Each cylindrical element 208A-208C is provided with electrical elements 7. A stationary elongate support element 210 is positioned spaced from but close to the rotor 207 and has a part cylindrical surface 211 concentric with the axis 209 of the rotor 207. The constriction/stimulation unit 205 is applied on a patient's biliary duct 212, so that the biliary duct 212 extends between the support element 210 and the rotor 207.

The control device 4 controls the rotor 207 of the constriction device to rotate so that the constriction elements 208A-208C successively constrict wall portions of a series of wall portions of the tubular biliary duct 212 against the elongate support element 210. The electrical elements 7 of the constriction elements 208A-208C stimulate the constricted wall portions with electric pulses so that the wall portions thicken and close the lumen of the biliary duct 212. FIG. 54A illustrates how the constriction element 208A has started to constrict the wall of the biliary duct 212 and how the lumen of the biliary duct 212 is closed with the aid of the electrical elements 7 on the constriction element 208A, whereas the constriction element 208B is about to release the biliary duct 212. FIG. 54B illustrates how the constriction element 208A has advanced about halfway along the elongate support element 210 and moved the bile and/or gallstones in the biliary duct in a direction indicated by an arrow. The constriction element 208B has released the biliary duct 212, whereas the constriction element 208C is about to engage the biliary duct 212. Thus, the control device 4 controls the rotor 207 to cyclically move the constriction elements 208A-208C one after the other along the elongate support element 210 while constricting the wall portions of the biliary duct 212, so that the bile and/or gallstones in the biliary duct 212 is moved in a peristaltic manner.

Figure 55A:
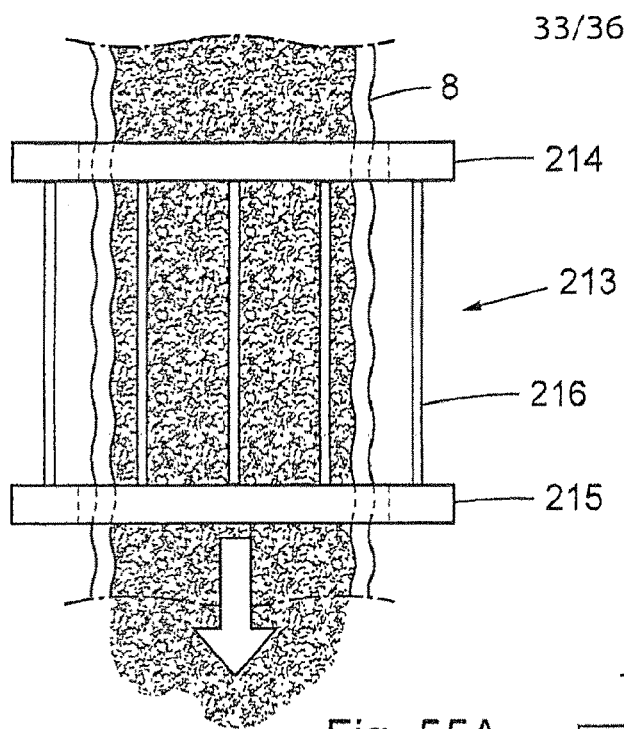
FIG. 55A is a schematic view of another mechanically operable non-inflatable constriction device used for practicing the method of the invention.
Figure 55B:
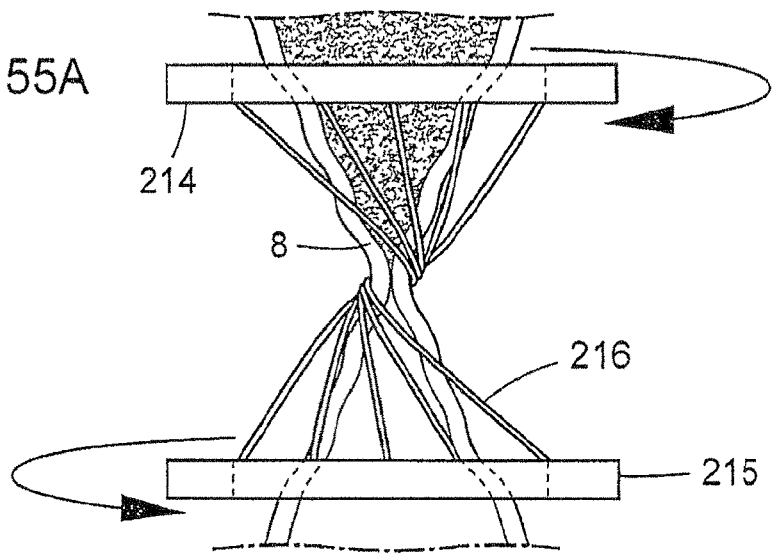
FIG. 55B shows the constriction device of FIG. 55A in a constricted state.
Figure 55:
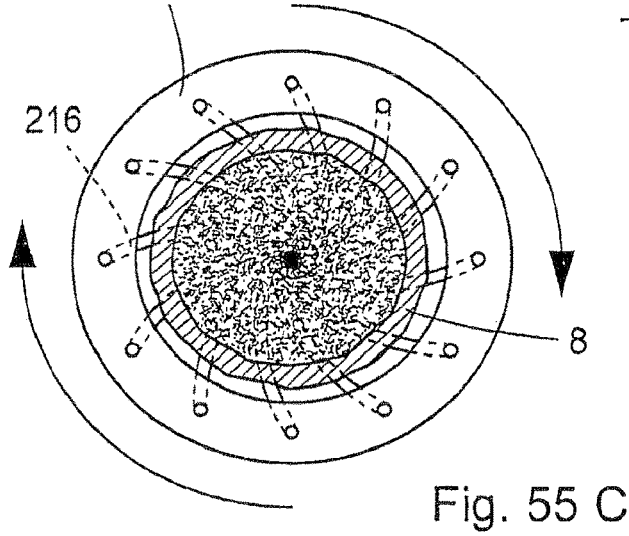
FIG. 55C is an end view of the embodiment of FIG. 55B.

FIGS. 55A, 55B and 55C show another mechanically operable constriction device 213 used for practicing the method of the invention. Referring to FIG. 55A, the constriction device 213 includes a first ring-shaped holder 214 applied on a biliary duct 8 of a patient and a second ring-shaped holder 215 also applied on the biliary duct 8 spaced apart from holder 214. There are elastic strings 216 (here twelve strings) that extend in parallel along the biliary duct 8 and interconnect the two holders 213, 214 without contacting the biliary duct 8. FIG. 55A illustrate an inactivated state of the constriction device 213 in which the biliary duct 8 is not constricted.

Referring to FIGS. 55B and 55C, when biliary duct 8 is to be constricted the ring-shaped holders 213 and 214 are rotated by an operation means (not shown) in opposite directions, whereby the elastic strings 216 constrict the biliary duct 8 in a manner that appears from FIGS. 55B and 55C. For the sake of clarity, only five strings 216 are shown in FIG. 55B.

In accordance with the present invention, electrodes for electrically stimulating the biliary duct 8 to cause contraction of the wall of the biliary duct 8 are attached to the strings 216 (not shown in FIGS. 55A-55C).

Figure 56:
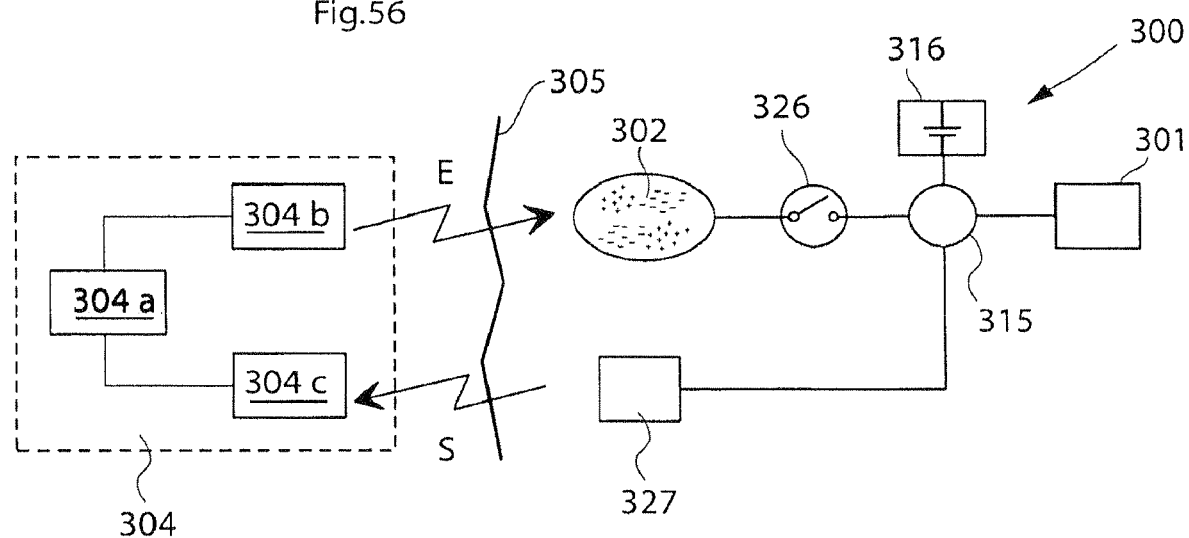
FIG. 56 is a schematic block diagram illustrating an arrangement for supplying an accurate amount of wireless energy used for the operation of the constriction/stimulation unit as described above.

FIG. 56 schematically illustrates an arrangement capable of sending information from inside the patient's body to the outside thereof to give information related to at least one functional parameter of the apparatus, and/or related to a physical parameter of the patient, in order to supply an accurate amount of energy to an implanted internal energy receiver 302 connected to energy consuming components of an implanted constriction/stimulation unit 301 of the apparatus. Such an energy receiver 302 may include a source of energy and/or an energy-transforming device. Briefly described, wireless energy is transmitted from an external source of energy 304a located outside the patient and is received by the internal energy receiver 302 located inside the patient. The internal energy receiver is adapted to directly or indirectly supply received energy to the energy consuming components of the constriction/stimulation unit 301 via a switch 326. An energy balance is determined between the energy received by the internal energy receiver 302 and the energy used for the constriction/stimulation unit 301, and the transmission of wireless energy is then controlled based on the determined energy balance. The energy balance thus provides an accurate indication of the correct amount of energy needed, which is sufficient to operate the constriction/stimulation unit 301 properly, but without causing undue temperature rise.

In FIG. 56 the patient's skin is indicated by a vertical line 305. Here, the energy receiver comprises an energy-transforming device 302 located inside the patient, preferably just beneath the patient's skin 305. Generally speaking, the implanted energy-transforming device 302 may be placed in the abdomen, thorax, muscle fascia (e.g. in the abdominal wall), subcutaneously, or at any other suitable location. The implanted energy-transforming device 302 is adapted to receive wireless energy E transmitted from the external source of energy 304a provided in an external energy-transmission device 304 located outside the patient's skin 305 in the vicinity of the implanted energy-transforming device 302.

As is well known in the art, the wireless energy E may generally be transferred by means of any suitable Transcutaneous Energy Transfer (TET) device, such as a device including a primary coil arranged in the external source of energy 304a and an adjacent secondary coil arranged in the implanted energy-transforming device 302. When an electric current is fed through the primary coil, energy in the form of a voltage is induced in the secondary coil which can be used to power the implanted energy consuming components, e.g. after storing the incoming energy in an implanted source of energy, such as a rechargeable battery or a capacitor. However, the present invention is generally not limited to any particular energy transfer technique, TET devices or energy sources, and any kind of wireless energy may be used.

The amount of energy received by the implanted energy receiver may be compared with the energy used by the implanted components of the apparatus. The term "energy used" is then understood to include also energy stored by implanted components of the apparatus. A control device includes an external control unit 304b that controls the external source of energy 304a based on the determined energy balance to regulate the amount of transferred energy. In order to transfer the correct amount of energy, the energy balance and the required amount of energy is determined by means of a determination device including an implanted internal control unit 315 connected between the switch 326 and the constriction/stimulation unit 301. The internal control unit 315 may thus be arranged to receive various measurements obtained by suitable sensors or the like, not shown, measuring certain characteristics of the constriction/stimulation unit 301, somehow reflecting the required amount of energy needed for proper operation of the constriction/stimulation unit 301. Moreover, the current condition of the patient may also be detected by means of suitable measuring devices or sensors, in order to provide parameters reflecting the patient's condition. Hence, such characteristics and/or parameters may be related to the current state of the constriction/stimulation unit 301, such as power consumption, operational mode and temperature, as well as the patient's condition reflected by parameters such as: body temperature, blood pressure, heartbeats and breathing. Other kinds of physical parameters of the patient and functional parameters of the device are described elsewhere.

Furthermore, a source of energy in the form of an accumulator 316 may optionally be connected to the implanted energy-transforming device 302 via the control unit 315 for accumulating received energy for later use by the constriction/stimulation unit 301. Alternatively or additionally, characteristics of such an accumulator, also reflecting the required amount of energy, may be measured as well. The accumulator may be replaced by a rechargeable battery, and the measured characteristics may be related to the current state of the battery, any electrical parameter such as energy consumption voltage, temperature, etc. In order to provide sufficient voltage and current to the constriction/stimulation unit 301, and also to avoid excessive heating, it is clearly understood that the battery should be charged optimally by receiving a correct amount of energy from the implanted energy-transforming device 302, i.e. not too little or too much. The accumulator may also be a capacitor with corresponding characteristics.

For example, battery characteristics may be measured on a regular basis to determine the current state of the battery, which then may be stored as state information in a suitable storage means in the internal control unit 315. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 315 of the determination device is adapted to determine the energy balance and/or the currently required amount of energy, (either energy per time unit or accumulated energy) based on measurements made by the above-mentioned sensors or measuring devices of the apparatus, or the patient, or an implanted source of energy if used, or any combination thereof. The internal control unit 315 is further connected to an internal signal transmitter 327, arranged to transmit a control signal reflecting the determined required amount of energy, to an external signal receiver 304c connected to the external control unit 304b. The amount of energy transmitted from the external source of energy 304a may then be regulated in response to the received control signal.

Alternatively, the determination device may include the external control unit 304b. In this alternative, sensor measurements can be transmitted directly to the external control unit 304b wherein the energy balance and/or the currently required amount of energy can be determined by the external control unit 304b, thus integrating the above-described function of the internal control unit 315 in the external control unit 304b. In that case, the internal control unit 315 can be omitted and the sensor measurements are supplied directly to the internal signal transmitter 327 which sends the measurements over to the external signal receiver 304c and the external control unit 304b. The energy balance and the currently required amount of energy can then be determined by the external control unit 304b based on those sensor measurements.

Hence, the present solution according to the arrangement of FIG. 56 employs the feed back of information indicating the required energy, which is more efficient than previous solutions because it is based on the actual use of energy that is compared to the received energy, e.g. with respect to the amount of energy, the energy difference, or the energy receiving rate as compared to the energy rate used by implanted energy consuming components. The apparatus may use the received energy either for consuming or for storing the energy in an implanted source of energy or the like. The different parameters discussed above would thus be used if relevant and needed and then as a tool for determining the actual energy balance. However, such parameters may also be needed per se for any actions taken internally to specifically operate the apparatus.

The internal signal transmitter 327 and the external signal receiver 304c may be implemented as separate units using suitable signal transfer means, such as radio, IR (Infrared) or ultrasonic signals. Alternatively, the internal signal transmitter 327 and the external signal receiver 304c may be integrated in the implanted energy-transforming device 302 and the external source of energy 304a, respectively, so as to convey control signals in a reverse direction relative to the energy transfer, basically using the same transmission technique. The control signals may be modulated with respect to frequency, phase or amplitude.

Thus, the feedback information may be transferred either by a separate communication system including receivers and transmitters or may be integrated in the energy system. Such an integrated information feedback and energy system comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a power switch for switching the connection of the internal first coil to the first electronic circuit on and off, such that feedback information related to the charging of the first coil is received by the external energy transmitter in the form of an impedance variation in the load of the external second coil, when the power switch switches the connection of the internal first coil to the first electronic circuit on and off. In implementing this system in the arrangement of FIG. 17, the switch 326 is either separate and controlled by the internal control unit 315, or integrated in the internal control unit 315. It should be understood that the switch 326 should be interpreted in its broadest embodiment. This means a transistor, MCU, MCPU, ASIC FPGA or a DA converter or any other electronic component or circuit that may switch the power on and off.

To conclude, the energy supply arrangement illustrated in FIG. 56 may operate basically in the following manner. The energy balance is first determined by the internal control unit 315 of the determination device. A control signal reflecting the required amount of energy is also created by the internal control unit 315, and the control signal is transmitted from the internal signal transmitter 327 to the external signal receiver 304c. Alternatively, the energy balance can be determined by the external control unit 304b instead depending on the implementation, as mentioned above. In that case, the control signal may carry measurement results from various sensors. The amount of energy emitted from the external source of energy 304a can then be regulated by the external control unit 304b, based on the determined energy balance, e.g. in response to the received control signal. This process may be repeated intermittently at certain intervals during ongoing energy transfer, or may be executed on a more or less continuous basis during the energy transfer.

The amount of transferred energy can generally be regulated by adjusting various transmission parameters in the external source of energy 304a, such as voltage, current, amplitude, wave frequency and pulse characteristics. This system may also be used to obtain information about the coupling factors between the coils in a TET system even to calibrate the system both to find an optimal place for the external coil in relation to the internal coil and to optimize energy transfer. Simply comparing in this case the amount of energy transferred with the amount of energy received. For example if the external coil is moved the coupling factor may vary and correctly displayed movements could cause the external coil to find the optimal place for energy transfer. Preferably, the external coil is adapted to calibrate the amount of transferred energy to achieve the feedback information in the determination device, before the coupling factor is maximized.

This coupling factor information may also be used as a feedback during energy transfer. In such a case, the energy system of the present invention comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a feedback device for communicating out the amount of energy received in the first coil as a feedback information, and wherein the second electronic circuit includes a determination device for receiving the feedback information and for comparing the amount of transferred energy by the second coil with the feedback information related to the amount of energy received in the first coil to obtain the coupling factor between the first and second coils. The energy transmitter may regulate the transmitted energy in response to the obtained coupling factor.

Figure 57:
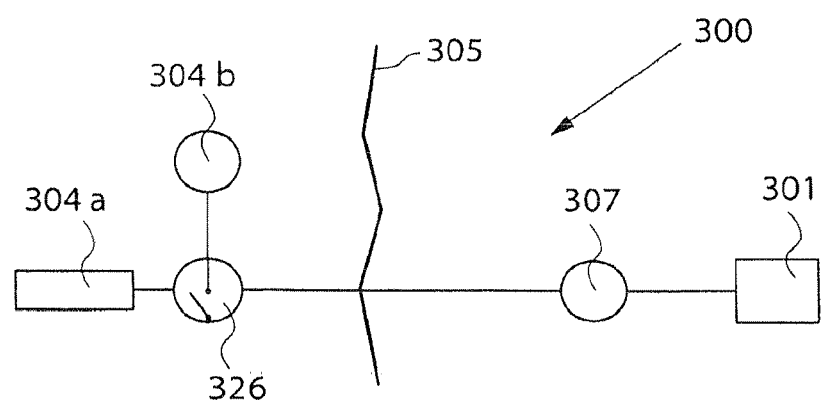
FIG. 57 schematically shows an embodiment of the invention, in which the apparatus is operated with wire bound energy.

With reference to FIG. 57, although wireless transfer of energy for operating the apparatus has been described above to enable non-invasive operation, it will be appreciated that the apparatus can be operated with wire bound energy as well. Such an example is shown in FIG. 57, wherein an external switch 326 is interconnected between the external source of energy 304a and an operation device, such as an electric motor 307 operating the constriction/stimulation unit 301. An external control unit 304b controls the operation of the external switch 326 to effect proper operation of the constriction/stimulation unit 301.

Figure 58:
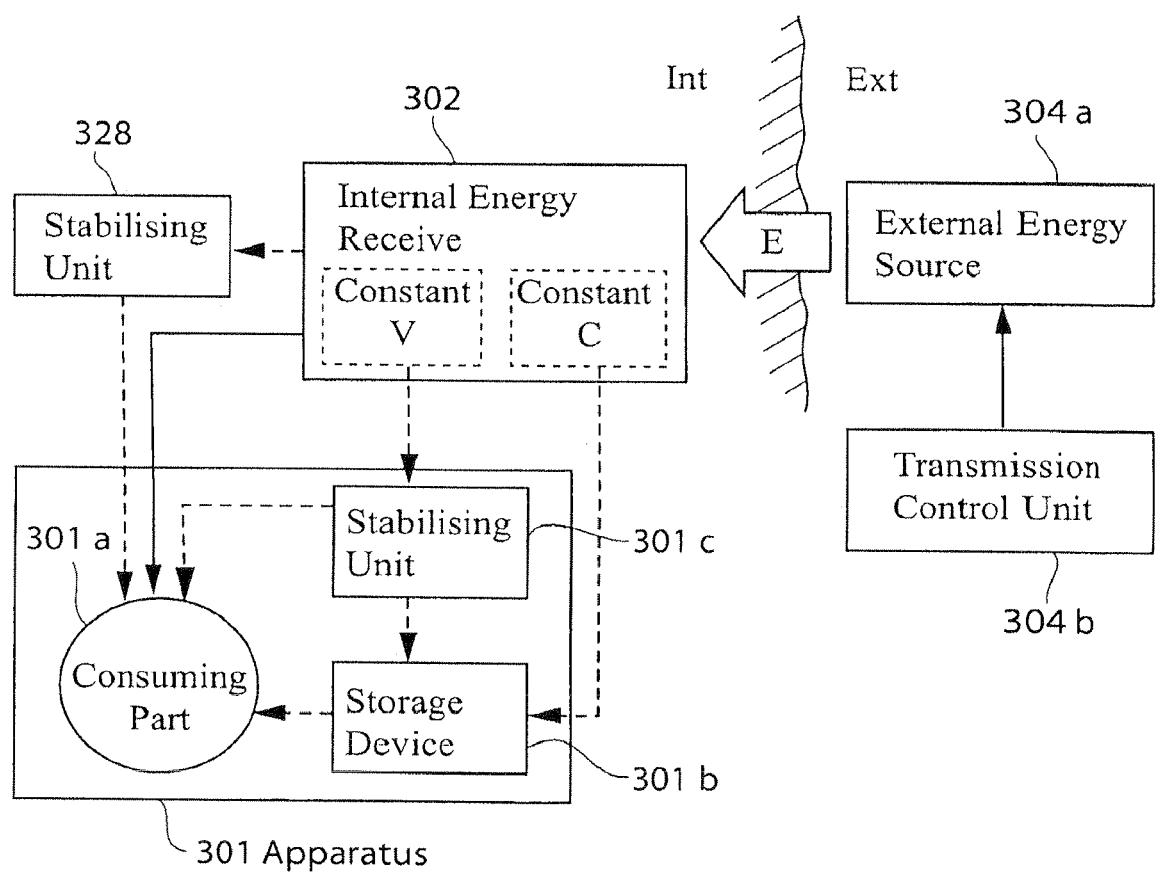
FIG. 58 is a more detailed block diagram of an arrangement for controlling the transmission of wireless energy used for the operation of the constriction/stimulation unit as described above.

FIG. 58 illustrates different embodiments for how received energy can be supplied to and used by the constriction/stimulation unit 301. Similar to the example of FIG. 56, an internal energy receiver 302 receives wireless energy E from an external source of energy 304a which is controlled by a transmission control unit 304b. The internal energy receiver 302 may comprise a constant voltage circuit, indicated as a dashed box "constant V" in FIG. 58, for supplying energy at constant voltage to the constriction/stimulation unit 301. The internal energy receiver 302 may further comprise a constant current circuit, indicated as a dashed box "constant C" in the figure, for supplying energy at constant current to the constriction/stimulation unit 301.

The constriction/stimulation unit 301 comprises an energy consuming part 301a, which may be a motor, pump, restriction device, or any other medical appliance that requires energy for its electrical operation. The constriction/stimulation unit 301 may further comprise an energy storage device 301b for storing energy supplied from the internal energy receiver 302. Thus, the supplied energy may be directly consumed by the energy consuming part 301a, or stored by the energy storage device 301b, or the supplied energy may be partly consumed and partly stored. The constriction/stimulation unit 301 may further comprise an energy stabilizing unit 301c for stabilizing the energy supplied from the internal energy receiver 302. Thus, the energy may be supplied in a fluctuating manner such that it may be necessary to stabilize the energy before consumed or stored.

The energy supplied from the internal energy receiver 302 may further be accumulated and/or stabilized by a separate energy stabilizing unit 328 located outside the constriction/stimulation unit 301, before being consumed and/or stored by the constriction/stimulation unit 301. Alternatively, the energy stabilizing unit 328 may be integrated in the internal energy receiver 302. In either case, the energy stabilizing unit 328 may comprise a constant voltage circuit and/or a constant current circuit.

It should be noted that FIG. 56 and FIG. 58 illustrate some possible but non-limiting implementation options regarding how the various shown functional components and elements can be arranged and connected to each other. However, the skilled person will readily appreciate that many variations and modifications can be made within the scope of the present invention.

Figure 59:
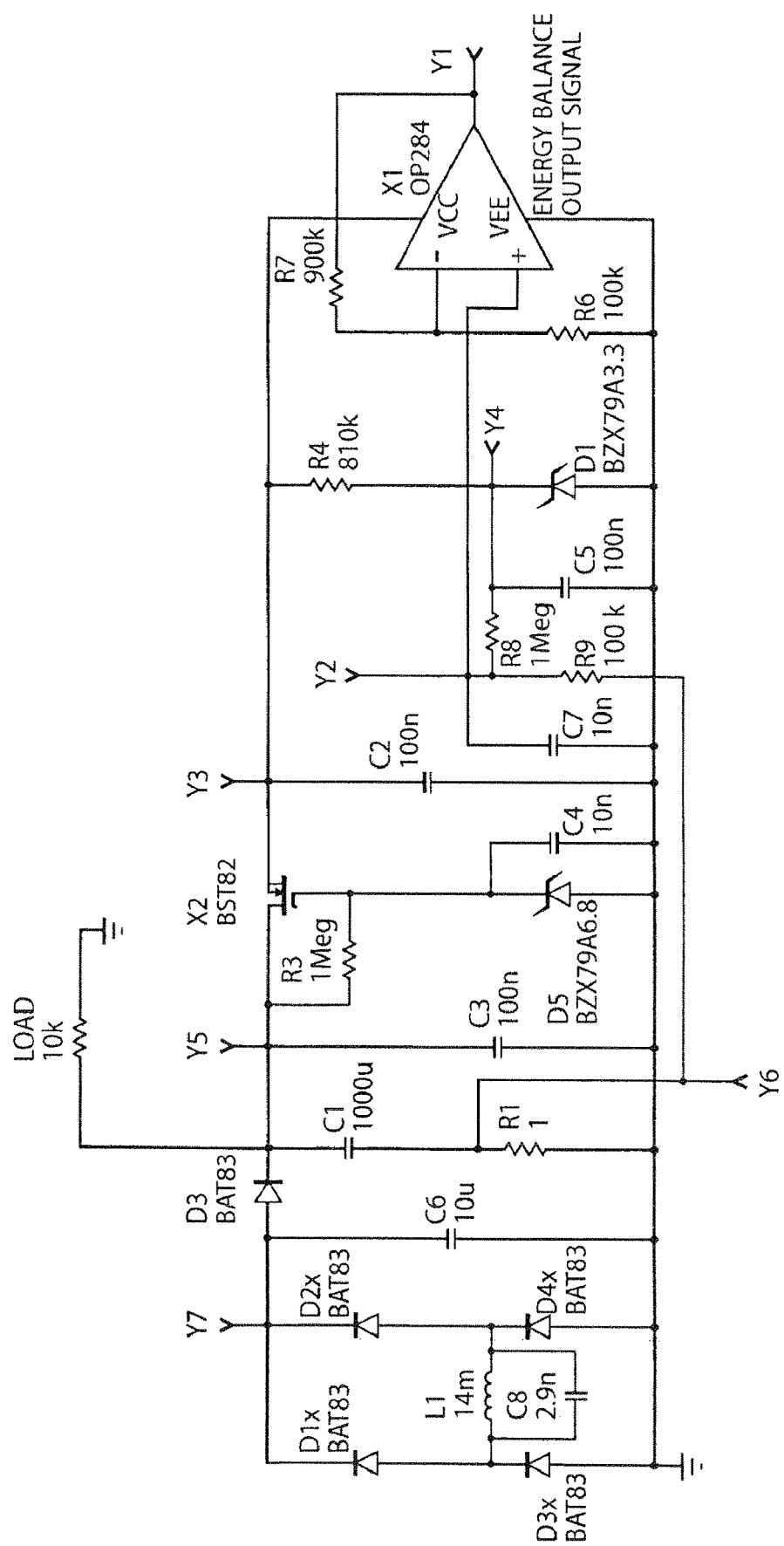
FIG. 59 is a circuit for the arrangement shown in FIG. 19, according to a possible implementation example.

FIG. 59 schematically shows an energy balance measuring circuit of one of the proposed designs of the apparatus for controlling transmission of wireless energy, or energy balance. The circuit has an output signal centered on 2.5V and proportionally related to the energy imbalance. The derivative of this signal shows if the value goes up and down and how fast such a change takes place. If the amount of received energy is lower than the energy used by implanted components of the apparatus, more energy is transferred and thus charged into the source of energy. The output signal from the circuit is typically fed to an A/D converter and converted into a digital format. The digital information can then be sent to the external energy-transmission device allowing it to adjust the level of the transmitted energy.

Another possibility is to have a completely analog system that uses comparators comparing the energy balance level with certain maximum and minimum thresholds sending information to external energy-transmission device if the balance drifts out of the max/min window.

The schematic FIG. 59 shows a circuit implementation for a system that transfers energy to the implanted energy components of the apparatus from outside of the patient's body using inductive energy transfer. An inductive energy transfer system typically uses an external transmitting coil and an internal receiving coil. The receiving coil, L1, is included in the schematic FIG. 59; the transmitting parts of the system are excluded.

The implementation of the general concept of energy balance and the way the information is transmitted to the external energy transmitter can of course be implemented in numerous different ways. The schematic FIG. 20 and the above described method of evaluating and transmitting the information should only be regarded as examples of how to implement the control system.

Circuit Details

In FIG. 59 the symbols Y1, Y2, Y3 and so on symbolize test points within the circuit. The components in the diagram and their respective values are values that work in this particular implementation which of course is only one of an infinite number of possible design solutions.

Energy to power the circuit is received by the energy receiving coil L1. Energy to implanted components is transmitted in this particular case at a frequency of 25 kHz. The energy balance output signal is present at test point Y1.

The embodiments described in connection with FIGS. 56, 58 and 59 identify a general method of the present invention for controlling transmission of wireless energy to implanted energy consuming components of the apparatus. Such a method will be defined in general terms in the following.

A method is thus provided for controlling transmission of wireless energy supplied to implanted energy consuming components of an apparatus as described above. The wireless energy E is transmitted from an external source of energy located outside the patient and is received by an internal energy receiver located inside the patient, the internal energy receiver being connected to the implanted energy consuming components of the apparatus for directly or indirectly supplying received energy thereto. An energy balance is determined between the energy received by the internal energy receiver and the energy used for the operation of the implanted parts of the apparatus. The transmission of wireless energy E from the external source of energy is then controlled based on the determined energy balance.

The wireless energy may be transmitted inductively from a primary coil in the external source of energy to a secondary coil in the internal energy receiver. A change in the energy balance may be detected to control the transmission of wireless energy based on the detected energy balance change. A difference may also be detected between energy received by the internal energy receiver and energy used for the operation of the implanted parts of the apparatus, to control the transmission of wireless energy based on the detected energy difference.

When controlling the energy transmission, the amount of transmitted wireless energy may be decreased if the detected energy balance change implies that the energy balance is increasing, or vice versa. The decrease/increase of energy transmission may further correspond to a detected change rate.

The amount of transmitted wireless energy may further be decreased if the detected energy difference implies that the received energy is greater than the used energy, or vice versa. The decrease/increase of energy transmission may then correspond to the magnitude of the detected energy difference.

As mentioned above, the energy used for the operation of the implanted parts of the apparatus be consumed to operate the implanted parts of the apparatus and/or stored in at least one implanted energy storage device of the apparatus.

When electrical and/or physical parameters of the implanted parts of the apparatus and/or physical parameters of the patient are determined, the energy may be transmitted for consumption and storage according to a transmission rate per time unit which is determined based on said parameters. The total amount of transmitted energy may also be determined based on said parameters.

When a difference is detected between the total amount of energy received by the internal energy receiver and the total amount of consumed and/or stored energy, and the detected difference is related to the integral over time of at least one measured electrical parameter related to said energy balance, the integral may be determined for a monitored voltage and/or current related to the energy balance.

When the derivative is determined over time of a measured electrical parameter related to the amount of consumed and/or stored energy, the derivative may be determined for a monitored voltage and/or current related to the energy balance.

The transmission of wireless energy from the external source of energy may be controlled by applying to the external source of energy electrical pulses from a first electric circuit to transmit the wireless energy, the electrical pulses having leading and trailing edges, varying the lengths of first time intervals between successive leading and trailing edges of the electrical pulses and/or the lengths of second time intervals between successive trailing and leading edges of the electrical pulses, and transmitting wireless energy, the transmitted energy generated from the electrical pulses having a varied power, the varying of the power depending on the lengths of the first and/or second time intervals.

In that case, the frequency of the electrical pulses may be substantially constant when varying the first and/or second time intervals. When applying electrical pulses, the electrical pulses may remain unchanged, except for varying the first and/or second time intervals. The amplitude of the electrical pulses may be substantially constant when varying the first and/or second time intervals. Further, the electrical pulses may be varied by only varying the lengths of first time intervals between successive leading and trailing edges of the electrical pulses.

A train of two or more electrical pulses may be supplied in a row, wherein when applying the train of pulses, the train having a first electrical pulse at the start of the pulse train and having a second electrical pulse at the end of the pulse train, two or more pulse trains may be supplied in a row, wherein the lengths of the second time intervals between successive trailing edge of the second electrical pulse in a first pulse train and leading edge of the first electrical pulse of a second pulse train are varied.

When applying the electrical pulses, the electrical pulses may have a substantially constant current and a substantially constant voltage. The electrical pulses may also have a substantially constant current and a substantially constant voltage. Further, the electrical pulses may also have a substantially constant frequency. The electrical pulses within a pulse train may likewise have a substantially constant frequency.

The circuit formed by the first electric circuit and the external source of energy may have a first characteristic time period or first time constant, and when effectively varying the transmitted energy, such frequency time period may be in the range of the first characteristic time period or time constant or shorter.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method for treating a patient suffering from problems associated with bile and/or gallstones in a patient's biliary duct, the method comprising:
   creating an opening in the abdomen of the patient;
   dissecting an area of at least a portion of the tissue wall of the biliary duct;
   placing a constriction device and a stimulation device on an outer surface of the patient's biliary duct in operative engagement with the biliary duct.

2. The method according to claim 1, further comprising the steps of
   inserting a needle like tube into the abdomen of the patient's body,
   using the needle like tube to fill the abdomen with gas thereby expanding the abdominal cavity,
   placing at least two laparoscopical trocars in the patient's body,
   inserting a camera through one of the trocars into the abdomen,
   inserting a dissecting tool through any of the trocar and dissecting an area of at least one portion of the tissue wall of the biliary duct,
   placing a constriction device and a stimulation device in the dissected area in operative engagement with the biliary duct.

3. The method according to claim 1, wherein the constriction device and stimulation device are comprised in a flow influence device.

4. The method according to claim 1, comprising the additional step of placing an operation device within the body.

5. The method according to claim 4, wherein the step of implanting the at least one operation device further comprises the steps of implanting the operation device at a distance from the stimulation device and/or constriction device.

6. The method according to claim 4, wherein the step of implanting the at least one operation device comprising implanting at least one of: an electric motor, a hydraulic device, a mechanical device, a magnetic device, a piezoelectric element, an eccentric mechanism, and an electromagnetic mechanism.

7. The method according to claim 1, further comprising the additional step of placing an implantable internal energy source within the patient's body.

8. The method according to claim 1, further comprising at least one of the following steps of:
   providing a wireless remote control, and
   implanting at least one switch implantable in the patient, being usable for manually and non-invasively controlling the apparatus.

9. The method according to claim 1, further comprises the step of implanting a motor for operating the apparatus.

10. The method according to claim 1, further comprises the step of implanting a pump for operating the apparatus.

11. The method according to claim 1, wherein the apparatus is included in a system and the method comprising implanting an internal communicator adapted to feed data related to the apparatus or the patient to an external data communicator, and allowing postoperatively the external data communicator to feed data to the internal data communicator.

12. The method according to claim 11, further comprising the steps of implanting a mechanical operation device comprising a motor, comprising a gearbox reducing motor speed.

13. The method according to claim 1, further comprising the step of
   implanting an internal energy receiver, adapted to be energized non-invasively and wirelessly by an energy transmission device from outside the patient's body.

14. The method according to claim 13, sending energy from the internal energy receiver which is to be used by at least one of:
   an implantable internal energy source being chargeable by the energy, and
   at least one implantable energy consuming component of the apparatus.

15. The method according to claim 14, further comprising the step of implanting a sensor and/or a measuring device, allowing to sense or measure at least one of:
   at least one physical parameter of the patient, and
   at least one functional parameter related to the apparatus.

16. The method according to claim 14, further comprises the step of implanting a feedback device allowing to send feedback information from inside the patient's body to the outside of the patient's body, wherein the feedback information being related to at least one of; at least one physical parameter of the patient and at least one functional parameter related to the apparatus.

17. The method according to claim 14, further comprising implanting an implantable internal control unit, usable for automatically controlling the constriction device and/or stimulation device based on at least one of:
   input from at least one sensor adapted to detect at least one of:
   a physical parameter of the patient and a functional parameter of the apparatus, according to preprogrammed data.

18. The method according to claim 1, wherein the stimulation device is configured to stimulate the biliary duct with electrical pulses.

19. The method according to claim 1, wherein the stimulation device is configured to stimulate the biliary duct thermally.

20. The method according to claim 1, wherein the constriction device is configured to constrict the wall portion of the biliary duct, so that the movement of bile and/or gallstones in the biliary duct is stopped.

* * * * *